(12) United States Patent
Old et al.

(10) Patent No.: US 7,179,820 B2
(45) Date of Patent: Feb. 20, 2007

(54) PIPERIDINYL PROSTAGLANDIN E ANALOGS

(75) Inventors: David W. Old, Irvine, CA (US); Danny T. Dinh, Garden Grove, CA (US)

(73) Assignee: Allergan, Inc., Irvine, CA (US)

( * ) Notice: Subject to any disclaimer, the term of this patent is extended or adjusted under 35 U.S.C. 154(b) by 305 days.

(21) Appl. No.: 10/861,957

(22) Filed: Jun. 3, 2004

(65) Prior Publication Data

US 2004/0248854 A1  Dec. 9, 2004

Related U.S. Application Data

(63) Continuation-in-part of application No. 10/456,275, filed on Jun. 6, 2003, now Pat. No. 6,747,037, and a continuation-in-part of application No. 10/763,702, filed on Jan. 22, 2004.

(51) Int. Cl.
*A61K 31/445* (2006.01)
(52) U.S. Cl. .................. 514/327; 546/216
(58) Field of Classification Search .......... 514/277, 514/318, 319, 322, 324, 327; 546/24, 192, 546/193, 196, 202, 205, 210, 212, 213, 214, 546/216
See application file for complete search history.

(56) References Cited

U.S. PATENT DOCUMENTS

| | | | |
|---|---|---|---|
| 3,975,399 A | | 8/1976 | DeFranco et al. |
| 4,113,873 A | | 9/1978 | Himizu et al. |
| 4,115,401 A | | 9/1978 | Nanthavong et al. |
| 4,119,727 A | | 10/1978 | Buendia et al. |
| 4,177,346 A | | 12/1979 | Nelson |
| 4,299,970 A | * | 11/1981 | Cassidy et al. ............ 560/39 |
| 4,320,136 A | | 3/1982 | Scribner |
| 4,994,274 A | | 2/1991 | Chan et al. |
| 5,028,624 A | | 7/1991 | Chan et al. |
| 5,034,413 A | | 7/1991 | Chan et al. |
| 5,385,945 A | | 1/1995 | Garst et al. |
| 5,446,041 A | | 8/1995 | Chan et al. |
| 6,034,093 A | | 3/2000 | Ewing et al. |
| 6,258,844 B1 | | 7/2001 | Garst et al. |

(Continued)

FOREIGN PATENT DOCUMENTS

BE  841165  10/1976

(Continued)

OTHER PUBLICATIONS

Bito, L.Z., *Biological Protection with Prostaglandins*, Cohen, M.M., ed., Boca Raton, Fla, CRC Press Inc., 1985, pp. 231-252.

(Continued)

*Primary Examiner*—Cecilla J. Tsang
*Assistant Examiner*—Raymond Covington
(74) *Attorney, Agent, or Firm*—Brent A. Johnson; Robert J. Baran; Martin A. Voet

(57) ABSTRACT

The present invention provides a method of treating ocular hypertension or glaucoma which comprises administering to an animal having ocular hypertension or glaucoma therapeutically effective amount of a compound represented by the general formula I;

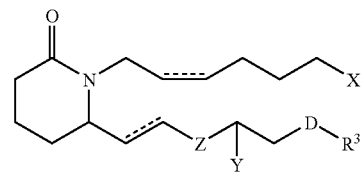

wherein X, Y, Z, D and $R^3$ are as defined in the specification.

Also disclosed are compounds comprising

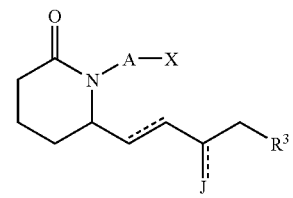

or a pharmaceutically acceptable salt or a prodrug thereof; wherein A, X, J, and $R^3$ are as defined in the specification.

Also disclosed are compounds having an α and an ω chain comprising

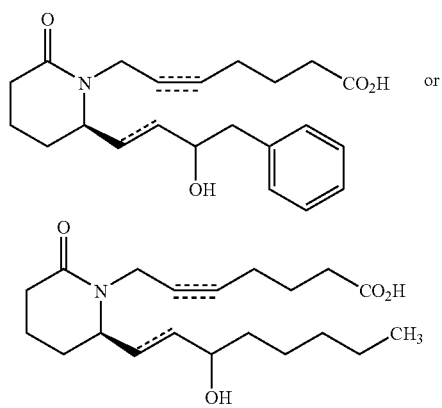

or derivatives thereof,
as defined in the specification
or pharmaceutically acceptable salts or prodrugs thereof.

3 Claims, 24 Drawing Sheets

U.S. PATENT DOCUMENTS

| | | |
|---|---|---|
| 6,291,522 B1 | 9/2001 | Burk |
| 6,303,658 B1 | 10/2001 | Burk |
| 6,307,092 B1 | 10/2001 | Burk et al. |
| 6,310,087 B2 | 10/2001 | Burk |
| 6,359,181 B1 | 3/2002 | Burk et al. |
| 6,376,533 B1 | 4/2002 | Burk et al. |
| 6,380,250 B1 | 4/2002 | Burk |
| 6,380,251 B1 | 4/2002 | Burk |
| 6,395,787 B1 | 5/2002 | Woodward et al. |
| 6,403,649 B1 | 6/2002 | Woodward et al. |
| 6,410,591 B1 | 6/2002 | Burk et al. |
| 6,414,022 B2 | 7/2002 | Burk |
| 6,476,064 B1 | 11/2002 | Old et al. |
| 6,531,504 B2 | 3/2003 | Burk et al. |
| 6,538,018 B1 | 3/2003 | Burk et al. |
| 6,573,294 B1 | 6/2003 | Old et al. |
| 6,586,462 B2 | 7/2003 | Burk et al. |
| 6,602,900 B2 | 8/2003 | Burk |
| 6,670,485 B2 | 12/2003 | Burk et al. |
| 6,680,337 B2 | 1/2004 | Burk |
| 2004/0142969 A1 | 7/2004 | Elworthy |

FOREIGN PATENT DOCUMENTS

| | | |
|---|---|---|
| GB | 1553595 | 10/1979 |
| GB | 1569982 | 6/1980 |
| GB | 1583163 | 1/1981 |
| JP | 5086034 | 4/1993 |
| WO | WO 89/09800 | 10/1989 |
| WO | WO 89/11275 | 11/1989 |
| WO | WO 93/03825 | 3/1993 |
| WO | WO 96/41639 | 12/1996 |
| WO | WO 00/21532 | 4/2000 |
| WO | WO 00/21542 | 4/2000 |
| WO | WO 01/46140 | 6/2001 |
| WO | WO2004/085430 | 7/2004 |

OTHER PUBLICATIONS

Bito, L.Z., *Applied Pharmacology in the Medical Treatment of Glaucomas,* Drance, S.M. and Neufeld, A.H. eds, New York, Grune & Stratton, 1984, pp. 477-505.

Nilsson et al, Invest. *Ophthalmol. Vis. Sci.* (suppl), 284 (1987).

Bito, L.Z., *Arch. Ophthalmol.* 105, 1036 (1987).

Siebold et al, *Prodrug* 5 3 1989.

Huang et al, Synth. Commun., "Preparation of Optically Pure ω-Hydroxymethyl Lactams", 1989, 19, 3485-3496.

Ono, K., et al., "Important role of $EP_4$, a subtype of prostaglandin (PG) E receptor, in osteoclast-like cell formation from mouse bone marrow cells induced by $PGE_2$" J. Endocrinology (1998) 158, R1-R5.

Saijo, S., et al., Heterocyclic prostaglandins IV "Synthesis of 8-Aza-11-deoxyprostaglandin $E_1$ and its related compounds", Yakugaku Zasshi 100 (4) 389-395 (1980).

Suda, M., et al., "Prostaglandin E ReceptorSubtypes in mouse osteoblastic cell line", Endocrinology 1996, vol. 137, No. 5, pp. 1698-1705.

Suzawa, T., et al., "The role of prostaglandin E receptor subtypes (EP1, EP2, EP3 and EP4) in bone resorption: an analysis using specific agonists for the respective EPs", Endocrinology, 2000, vol. 141, No. 4, pp. 1554-1557.

Zoretic, P.A., et al., "Synthesis of (E)-7-[[2-[4-(*m*-trifluoromethylphenoxy)-3α and 3β-hydroxy-1-butenyl]-5-oxo-1-pyrrolidinyl]]heptanoic acids" J. Heterocyclic Chem., 20, 465, (1983).

* cited by examiner

Figure 1

| Structure | Binding Data (IC50 in nM) | | | Functional Data (EC50 in nM) | | | | | | | |
|---|---|---|---|---|---|---|---|---|---|---|---|
| | hEP2 | hEP3D | hEP4 | hFP | hEP1 | hEP2 | hEP3A | hEP4 | hTP | hIP | hDP |
| [structure] | | | | NA | NA | NA | NA | NA | >10000 | NA | NA |
| [structure] | | | | NA | NA | NA | NA | NA | 653 | NA | NA |
| [structure] | | | | NA | NA | NA | NA | NA | 2474 | NA | NA |
| [structure] | | | | NA | NA | NA | NA | 10000 | 88 | NA | NA |

| | | | | | | | | | |
|---|---|---|---|---|---|---|---|---|---|
| 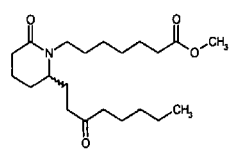 | | | | NA | NA | NA | NA | NA | >10000 | NA | NA |
| 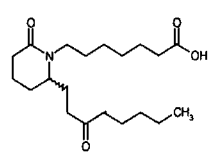 | | | | NA | NA | NA | NA | >10000 | 565 | NA | NA |
| 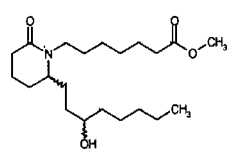 | | | | NA | NA | NA | NA | 1842 | >10000 | NA | NA |
| 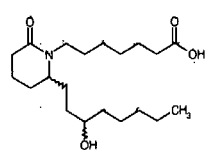 | NA | >10000 | 290 | NA | NA | >10000 | 99 | 449 | NA |

| | | | | | | | | |
|---|---|---|---|---|---|---|---|---|
| 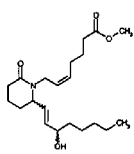 | NA | NA | NA | NA | NA | 815 | >10000 | NA | NA |
| 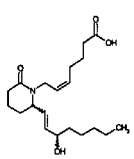 | NA | 440 | NA | >10000 | NA | 46 | 141 | NA | NA |
| 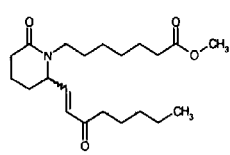 | | | NA | NA | NA | NA | NA | >10000 | NA | NA |
| 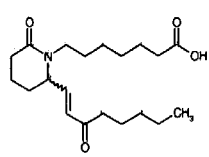 | | | NA | NA | NA | NA | 1290 | 238 | NA | NA |

| | | | | | | | | |
|---|---|---|---|---|---|---|---|---|
| 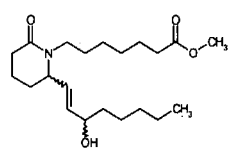 | NA | NA | NA | NA | 243 | NA | NA | NA |
| 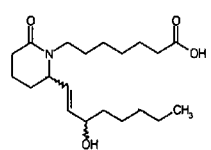 | NA | NA | NA | 10 | 424 | >10000 | NA | |
| 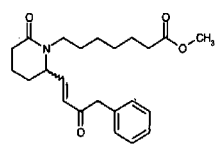 | NA | NA | NA | NA | NA | >10000 | NA | NA |
| 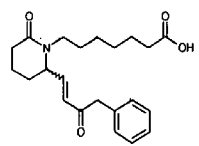 | NA | NA | NA | NA | >10000 | 207 | NA | NA |

| | | | | | | | | | | |
|---|---|---|---|---|---|---|---|---|---|---|
| 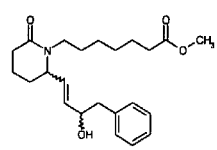 | NA | 2200 | NA | NA | NA | NA | 34 | NA | NA | NA |
| 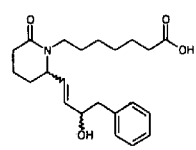 | NA | 65 | NA | NA | NA | NA | 3 | 2126 | NA | NA |
| 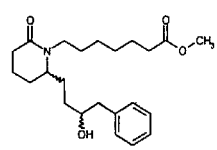 | NA | NA | >10000 | NA | NA | NA | 863 | >10000 | NA | NA |
| 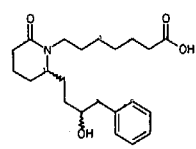 | >10000 | 1400 | NA | NA | NA | NA | 138 | 215 | NA | NA |

| | | | | | | | | |
|---|---|---|---|---|---|---|---|---|
| 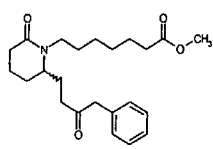 | NA | NA | NA | NA | NA | >10000 | NA | NA |
| 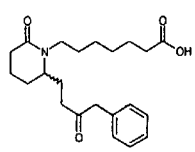 | NA | NA | NA | NA | | 218 | NA | NA |
| 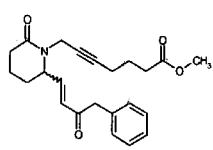 | NA | NA | NA | NA | NA | >10000 | NA | NA |
| 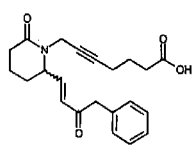 | NA | NA | NA | NA | >10000 | 660 | NA | NA |

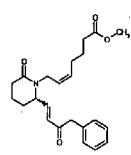
| | | | | | | | | | | |
|---|---|---|---|---|---|---|---|---|---|---|
| | | | NA | NA | NA | NA | NA | 4911 | NA | NA |
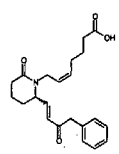
| | | | | | | | | | | |
|---|---|---|---|---|---|---|---|---|---|---|
| | | | NA | NA | NA | NA | >10000 | | NA | NA |
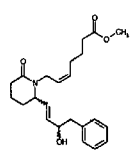
| | | | | | | | | | | |
|---|---|---|---|---|---|---|---|---|---|---|
| NA | NA | 3400 | NA | NA | NA | NA | 464 | >10000 | NA | NA |
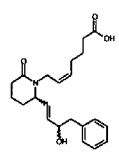
| | | | | | | | | | | |
|---|---|---|---|---|---|---|---|---|---|---|
| NA | NA | 130 | NA | NA | NA | NA | 8 | 597 | NA | NA |

| | | | | | | | | | | |
|---|---|---|---|---|---|---|---|---|---|---|
| 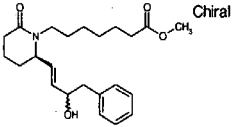 | NA | >10000 | 4600 | NA | NA | NA | NA | 274 | NA | NA | NA |
| 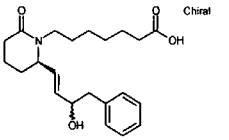 | NA | NA | 6800 | NA | NA | NA | NA | 0.56 | NA | NA | NA |
| 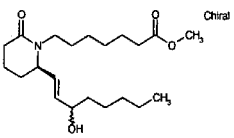 | NA | >10000 | 6500 | NA | NA | NA | NA | 385 | NA | NA | NA |
| 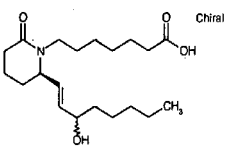 | NA | >10000 | >10000 | NA | NA | NA | >10000 | 10.4 | >10000 | NA | NA |

| | | | | | | | | | | |
|---|---|---|---|---|---|---|---|---|---|---|
| 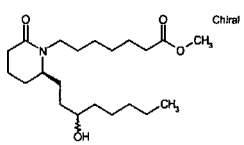 | NA | NA | >10000 | NA | NA | NA | NA | 2893 | NA | NA | NA |
| 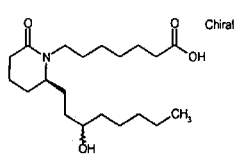 | >10000 | NA | 2500 | NA | NA | NA | NA | 481 | NA | NA | NA |
| 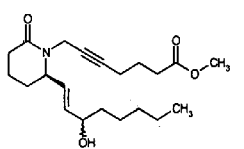 | | | | NA | NA | NA | NA | >10000 | NA | NA | NA |
| 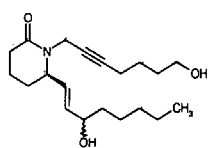 | | | | NA | NA | NA | NA | >10000 | NA | NA | NA |

| | | | | | | | | | | |
|---|---|---|---|---|---|---|---|---|---|---|
| 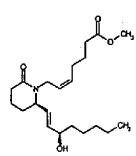 | NA | NA | 6000 | NA | NA | NA | NA | 649 | NA | NA | NA |
| 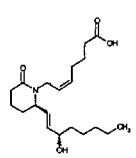 | NA | NA | 270 | NA | NA | NA | >10000 | 16.5 | >10000 | NA | NA |
| 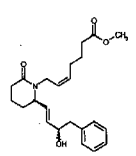 | NA | NA | 4600 | NA | NA | NA | NA | 593 | NA | NA | NA |
| 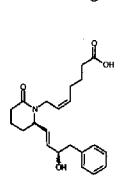 | NA | NA | 150 | NA | NA | NA | NA | 8.5 | NA | NA | NA |

| | | | | | | | | | | | |
|---|---|---|---|---|---|---|---|---|---|---|---|
| 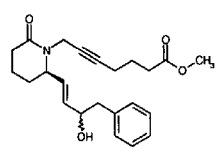 | NA | NA | >10000 | NA | NA | NA | NA | 3119 | NA | NA | NA |
| 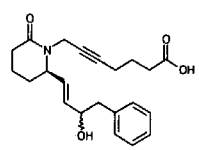 | NA | NA | 1000 | NA | NA | NA | NA | 81 | NA | NA | NA |
| 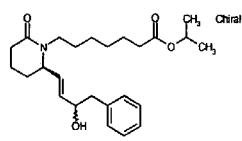 | NA | NA | 2800 | NA | NA | NA | NA | 246 | NA | NA | NA |
| 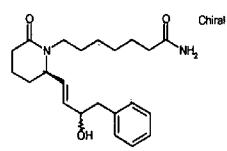 | NA | NA | 55 | NA | NA | NA | NA | 2 | NA | NA | NA |

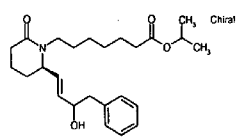 NA NA NA NA 164 NA NA NA
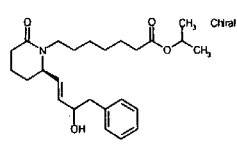 NA NA NA NA 339 NA NA NA
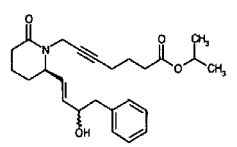 NA NA NA NA >10000 NA NA >10000
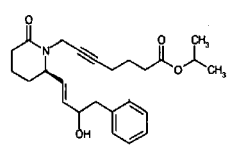 NA NA NA NA >10000 NA NA NA

| | | | | | | | | | | |
|---|---|---|---|---|---|---|---|---|---|---|
| 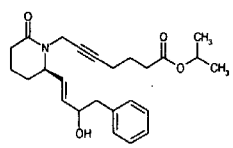 | | | NA | NA | NA | NA | NA | NA | NA | NA |
| 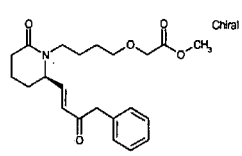 | | | NA | NA | NA | NA | NA | >10000 | NA | NA |
| 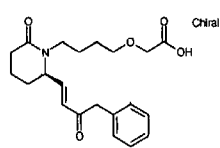 | NA | NA | 3800 | NA | NA | NA | >10000 | 300 | 2260 | NA | NA |
| 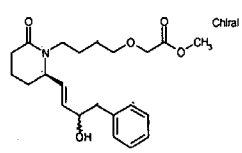 | NA | NA | 4200 | NA | NA | NA | NA | 1104 | NA | NA | NA |

| | | | | | | | | | | | |
|---|---|---|---|---|---|---|---|---|---|---|---|
| 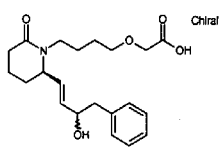 | NA | NA | 2300 | NA | NA | NA | NA | 145 | NA | NA | NA |
| 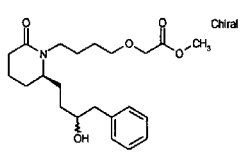 | | | | NA | NA | NA | >10000 | >10000 | NA | NA | NA |
| 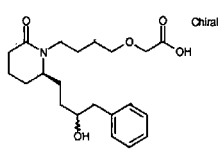 | | | | NA | NA | NA | NA | >10000 | NA | NA | NA |
| 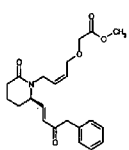 | | | | NA | NA | NA | NA | NA | NA | NA | NA |

| | | | | | | | | |
|---|---|---|---|---|---|---|---|---|
| 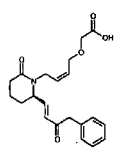 | NA | NA | NA | NA | 2556 | >10000 | NA | NA |
| 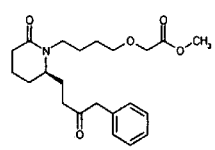 | NA | NA | NA | NA | 7542 | NA | NA | NA |
| 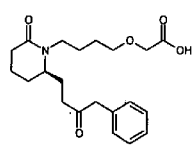 | NA | NA | NA | NA | 1975 | >10000 | NA | NA |
| 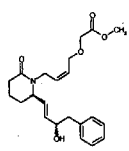 | NA | NA | NA | NA | NA | NA | NA | NA |

| | | | | | | | | |
|---|---|---|---|---|---|---|---|---|
| 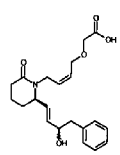 | NA | NA | NA | NA | >10000 | NA | NA | NA |
| 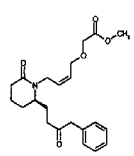 | NA | NA | NA | NA | NA | NA | NA | NA |
| 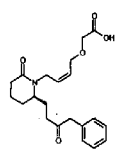 | NA | NA | NA | NA | >10000 | >10000 | NA | NA |
| 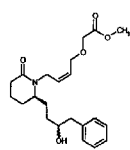 | NA | NA | NA | NA | NA | NA | NA | NA |

| | | | | | | | |
|---|---|---|---|---|---|---|---|
| 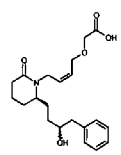 | NA | NA | NA | NA | >10000 | NA | NA | NA |
| 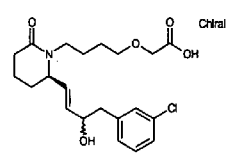 | NA | >10000 | >10000 | NA | 1.4 | 661 | NA | NA |
| 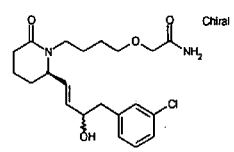 | NA | NA | NA | NA | 10 | >10000 | NA | NA |
| 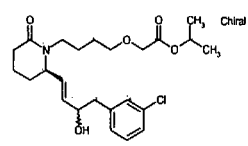 | NA | NA | NA | NA | 58 | NA | NA | NA |

| | | | | | | | | |
|---|---|---|---|---|---|---|---|---|
| 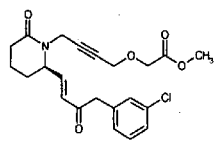 | NA | NA | NA | NA | NA | 1672 | NA | NA |
| 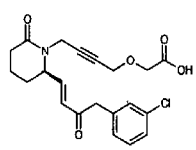 | NA | NA | NA | NA | 96 | 184 | NA | NA |
| 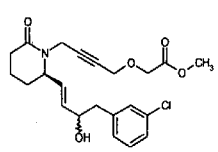 | NA | NA | NA | NA | 1868 | NA | NA | NA |
| 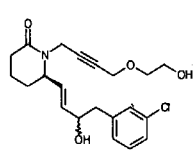 | NA | NA | NA | NA | 4553 | NA | NA | NA |

| | | | | | | | | |
|---|---|---|---|---|---|---|---|---|
| 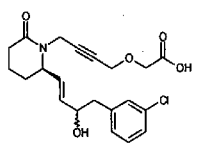 | NA | NA | NA | NA | 147 | 2916 | NA | NA |
| 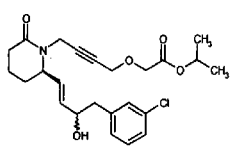 | NA | NA | NA | NA | >10000 | NA | NA | NA |
| 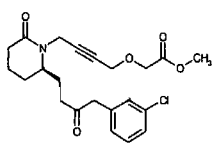 | NA | NA | NA | NA | NA | >10000 | NA | NA |
| 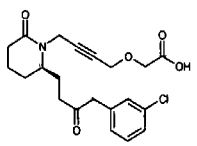 | NA | NA | NA | NA | 531 | 728 | NA | NA |

| | | | | | | | |
|---|---|---|---|---|---|---|---|
| 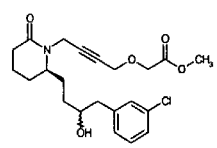 | NA | NA | NA | NA | 22523 | NA | NA | NA |
| 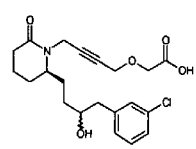 | NA | NA | NA | NA | 640 | 2672 | NA | NA |
| 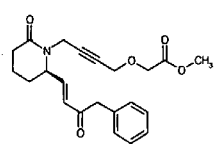 | NA | NA | NA | NA | NA | NA | NA | NA |
| 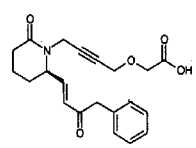 | NA | NA | NA | NA | 3147 | 3256 | NA | NA |

| | | | | | | | | |
|---|---|---|---|---|---|---|---|---|
| 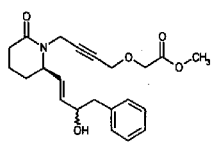 | NA | NA | NA | NA | >10000 | NA | NA | NA |
| 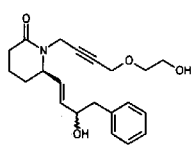 | NA | NA | NA | NA | NA | NA | NA | NA |
| 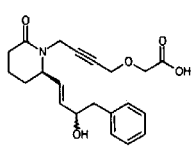 | NA | NA | NA | NA | 2709 | NA | NA | NA |
| 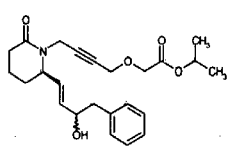 | NA | NA | NA | NA | NA | NA | NA | NA |

| | | | | | | | | |
|---|---|---|---|---|---|---|---|---|
| 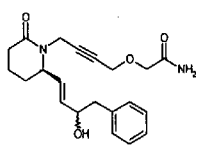 | NA | NA | NA | NA | >10000 | NA | NA | NA |
| 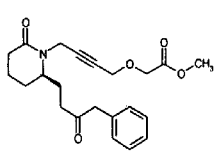 | NA | NA | NA | NA | NA | NA | NA | NA |
| 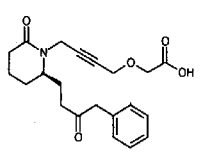 | NA | NA | NA | NA | NA | >10000 | NA | NA |
| 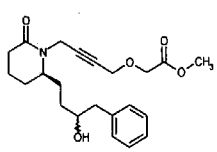 | NA | NA | NA | NA | NA | NA | NA | NA |

| | | | | | | | | |
|---|---|---|---|---|---|---|---|---|
| 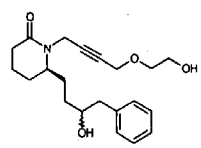 | NA | NA | NA | NA | 108 | NA | NA | NA |
| 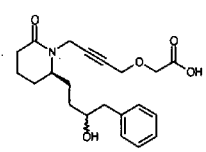 | NA | NA | NA | NA | >10000 | NA | NA | NA |
| 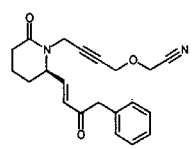 | NA | NA | NA | NA | NA | NA | NA | NA |
| 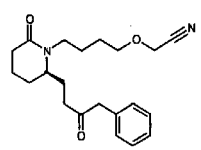 | NA | NA | NA | NA | NA | NA | NA | NA |

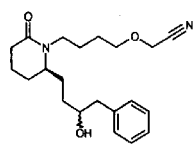
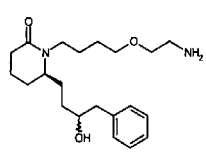
| | | | | | | | |
|---|---|---|---|---|---|---|---|
| NA | NA | NA | NA | NA | NA | NA | NA |
| NA | NA | NA | NA | NA | NA | NA | NA |

PIPERIDINYL PROSTAGLANDIN E ANALOGS

CROSS-REFERENCE TO RELATED APPLICATIONS

This application is a continuation-in-part of U.S. patent application Ser. No. 10/456,275, filed on Jun. 6, 2003, now U.S. Pat. No. 6,747,037 incorporated herein by reference, and claims priority thereto.

This application is also a continuation-in-part of U.S. patent application Ser. No. 10/763,702, filed on Jan. 22, 2004, incorporated herein by reference, and claims priority thereto.

FIELD OF THE INVENTION

The present invention relates to piperidinyl prostaglandin E analogs useful as therapeutic agents, e.g. ocular hypotensives that are particularly suited for the management of glaucoma.

BACKGROUND OF THE INVENTION

Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

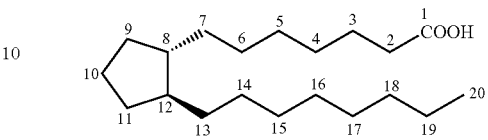

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by $\alpha$ or $\beta$ [e.g. prostaglandin $F_{2\alpha}$ ($PGF_{2\beta}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. Biological Protection with Prostaglandins, Cohen, M. M., ed., Boca Raton, Fla, CRC Press Inc., 1985, pp. 231–252; and Bito, L. Z., Applied Pharmacology in the Medical Treatment of Glaucomas Drance, S. M. and Neufeld, A. H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et. al., Invest. Ophthalmol. Vis. Sci. (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., Arch. Ophthalmol. 105, 1036 (1987), and Siebold et. al., Prodrug 5 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 596,430 (filed 10 Oct. 1990, now U.S. Pat. No. 5,446,041), relates to certain 11-acyl-prostaglandins, such as 11-pivaloyl, 11-acetyl, 11-isobutyryl, 11-valeryl, and 11'-isovaleryl $PGF_{2\alpha}$. Intraocular pressure reducing 15-acyl prostaglandins are disclosed in the co-pending application U.S. Ser. No. 175,476 (filed 29 Dec. 1993). Similarly, 11,15–9,15 and 9,11-diesters of prostaglandins, for example 11,15-dipivaloyl $PGF_{2\alpha}$ are known to have ocular hypotensive activity. See the co-pending patent applications U.S. Ser. No. 385,645 (filed 7 Jul. 1989, now U.S. Pat. No. 4,994,274), Ser. No. 584,370 (filed 18 Sep. 1990, now U.S. Pat. No. 5,028,624) and Ser. No. 585,284 (filed 18 Sep. 1990, now U.S. Pat. No. 5,034,413). The disclosures of all of these patent applications are hereby expressly incorporated by reference.

SUMMARY OF THE INVENTION

The present invention concerns piperidinyl prostaglandin E analogues which are useful in a method of treating ocular hypertension which comprises administering to a mammal having ocular hypertension a therapeutically effective amount of a compound of formula I

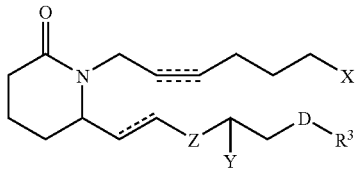

wherein hatched lines represent the α configuration, a triangle represents the β configuration, a wavy line represents either the α configuration or the α configuration and a dotted line represents the presence or absence of a double bond;

D represents a covalent bond or $CH_2$, O, S or NH;

X is $CO_2R$, $CONR_2$, $CH_2OR$, $P(O)(OR)_2$, $CONRSO_2R$, $SO_2NR_2$ or

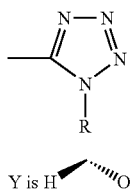

Y is 

Z is $CH_2$ or a covalent bond;

R is H or $R^2$;

$R^1$ is H, $R^2$, phenyl, or $COR^2$;

$R^2$ is $C_1$–$C_5$ lower alkyl or alkenyl and $R^3$ is selected from the group consisting of $R^2$, phenyl, thienyl, furanyl, pyridyl, benzothienyl, benzofuranyl, naphthyl, or substituted derivatives thereof, wherein the substituents maybe selected from the group consisting of $C_1$–$C_5$ alkyl, halogen, $CF_3$, CN, $NO_2$, $NR_2$, $CO_2R$ and OR.

Also disclosed are compounds comprising

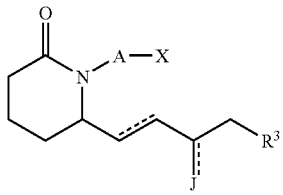

or a pharmaceutically acceptable salt or a prodrug thereof;

wherein a dotted line represents the presence or absence of a double bond;

A is —$(CH_2)_6$—, cis —$CH_2CH$=$CH$—$(CH_2)_3$—, or —$CH_2CH$≡$CH$—$(CH_2)_3$—, wherein 1 or 2 carbon atoms may be substituted with S or O;

X is $CO_2R$, $CONR_2$, $CH_2OR$, $P(O)(OR)_2$, $CONRSO_2R$ $SO_2NR_2$ or

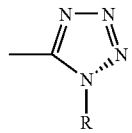

J is =O or —OH;

R is H or $R^2$;

$R^2$ is $C_1$–$C_5$ lower alkyl or alkenyl and $R^3$ is selected from the group consisting of $R^2$, phenyl, thienyl, furanyl, pyridyl, benzothienyl, benzofuranyl, naphthyl or substituted derivatives thereof, wherein the substituents maybe selected from the group consisting of $C_1$–$C_5$ alkyl, halogen, $CF_3$, CN, $NO_2$, $NR_2$, $CO_2R$ and OR.

Also disclosed are compounds having an α and an ω chain comprising

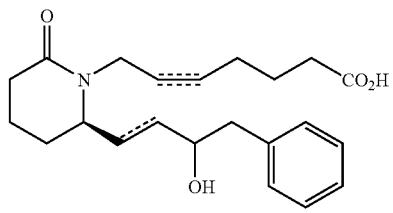

or derivatives thereof, wherein a dotted line indicates the presence or absence of a bond, a triangle represents the β configuration, and wherein said derivative has a structure as shown above except that from 1 to 2 alterations are made to the α chain and/or the ω chain, an alteration consisting of a. adding, removing, or substituting a non-hydrogen atom, b. converting an alcohol to a carbonyl, c. converting a $CO_2H$ to a moiety selected from the group consisting of $CONMe_2$, CONHMe, CONHEt, CON($OCH_3$)$CH_3$, $CONH_2$, $CON(CH_2CH_2OH)_2$, CONH($CH_2CH_2OH$), $CH_2OH$, $P(O)(OH)_2$, $CONHSO_2CH_3$, $SO_2NH_2$, $SO_2N(CH_3)_2$, $SO_2NH(CH_3)$,

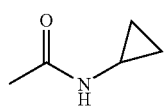 , and 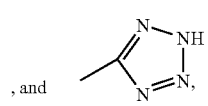

d. converting a phenyl moiety to a pyridinyl, furyl, or thienyl moiety, or e. adding a substituent comprising from 1 to 3 non-hydrogen atoms to an aromatic or a heteroaromatic ring;

or pharmaceutically acceptable salts or prodrugs thereof.

Also disclosed are compounds having an α and an ω chain comprising

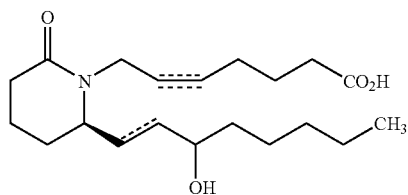

or derivatives thereof, wherein a dotted line indicates the presence or absence of a bond, a triangle represents the β configuration, and wherein said derivative has a structure as shown above except that from 1 to 2 alterations are made to the α chain and/or the ω chain, an alteration consisting of
a. adding, removed, or substituting a non-hydrogen atom,
b. converting an alcohol to a carbonyl, or
f. converting a $CO_2H$ to a moiety selected from the group consisting of $CONMe_2$, CONHMe, CONHEt, CON($OCH_3$)$CH_3$, $CONH_2$, $CON(CH_2CH_2OH)_2$, $CONH(CH_2CH_2OH)$, $CH_2OH$, $P(O)(OH)_2$, $CONHSO_2CH_3$, $SO_2NH_2$, $SO_2N(CH_3)_2$, $SO_2NH(CH_3)$,

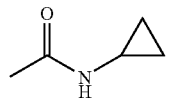, and 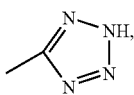

or pharmaceutically acceptable salts or prodrugs thereof.

In a still further aspect, the present invention relates to a pharmaceutical product, comprising
a container adapted to dispense its contents in a metered form; and
an ophthalmic solution therein, as hereinabove defined.

Finally, certain of the compounds represented by the above formulae, disclosed below and utilized in the method of the present invention are novel and unobvious.

BRIEF DESCRIPTION OF THE DRAWINGS

FIG. 1 is a Table showing the in vitro assay results for compounds prepared as disclosed herein.

DETAILED DESCRIPTION OF THE INVENTION

The present invention relates to the use of piperidinyl prostaglandin E therapeutic agents, e.g. as analogs as ocular hypotensives. The compounds used in accordance with the present invention are encompassed by the following structural formula I:

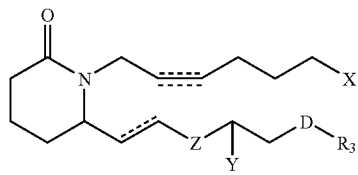

The preferred group of the compounds of the present invention includes compounds that have the following structural formula II.

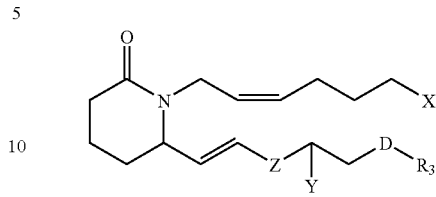

In the above formulae, the substituents and symbols are as hereinabove defined.

In the above formulae:

Preferably Y is

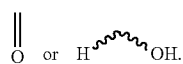

Preferably D represents a covalent bond or is $CH_2$; more preferably D is $CH_2$ and $R^3$ is n-propyl or D is a covalent bond and $R^3$ is phenyl.

Preferably Z represents a covalent bond.

Preferably R is H or $C_1$–$C_5$ lower alkyl.

Preferably $R^1$ is H.

Preferably $R^3$ is selected from the group consisting of phenyl and n-propyl.

Preferably X is $CO_2R$ and more preferably R is selected from the group consisting of H and methyl.

In relation to the identity of A disclosed in the chemical structures presented herein, in the broadest sense, A is —$(CH_2)_6$—, cis —$CH_2CH$=$CH$—$(CH_2)_3$—, or —$CH_2C$≡$CH$—$(CH_2)_3$—, wherein 1 or 2 carbon atoms may be substituted with S or O. In other words, A may be —$(CH_2)_6$—, cis —$CH_2CH$=$CH$—$(CH_2)_3$—, —$CH_2C$≡$CH$—$(CH_2)_3$—, or A may be a group which is related to one of these two moieties in that any carbon is substituted with S or O. For example, while not intending to limit the scope of the invention in any way, A may be an S substituted moiety such as one of the following or the like.

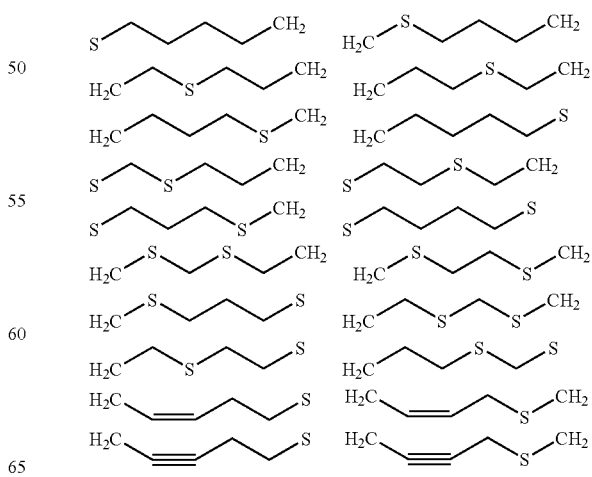

Alternatively, while not intending to limit the scope of the invention in any way, A may be an O substituted moiety such as one of the following or the like.

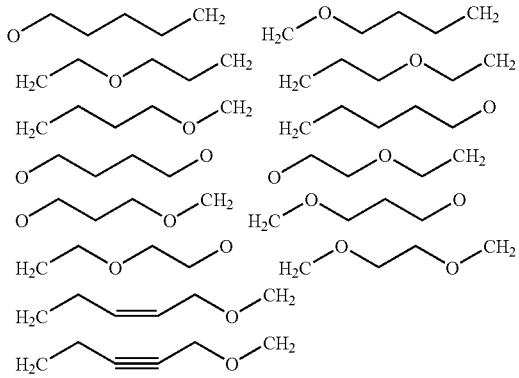

In other embodiments, A is —(CH$_2$)$_6$—, cis —CH$_2$CH=CH—(CH$_2$)$_3$—, or —CH$_2$CH≡CH—(CH$_2$)$_3$— having no heteroatom substitution.

Some compounds comprise

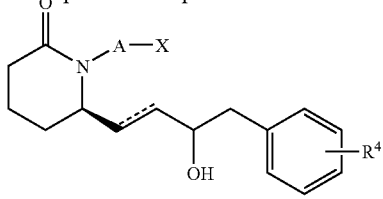

or a pharmaceutically acceptable salt or a prodrug thereof, wherein a triangle represents the β configuration, and R$^4$ is selected from the group consisting of H, C$_1$–C$_5$ alkyl, halogen, CF$_3$, CN, NO$_2$, NR$_2$, CO$_2$R and OR.

Other compounds comprise

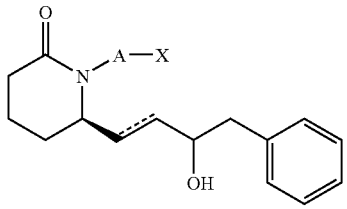

or a pharmaceutically acceptable salt or a prodrug thereof.

Other compounds comprise

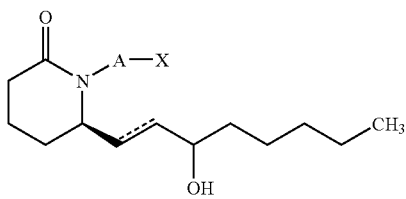

or a pharmaceutically acceptable salt or a prodrug thereof.

Other compounds comprise

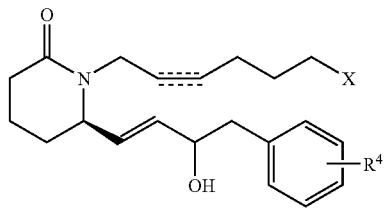

or a pharmaceutically acceptable salt or a prodrug thereof.

Other compounds comprise

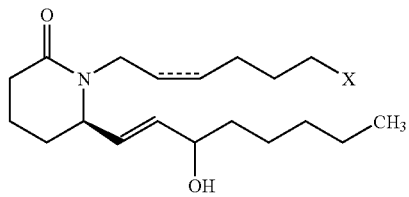

or a pharmaceutically acceptable salt or a prodrug thereof.

In all cases herein, a triangle represents the β configuration.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. While not intending to be limiting, an ester may an alkyl ester, an aryl ester, or a heteroaryl ester. The term alkyl has the meaning generally understood by those skilled in the art and refers to linear, branched, or cyclic alkyl moieties. C$_{1-6}$ alkyl esters are particularly useful, where alkyl part of the ester has from 1 to 6 carbon atoms and includes, but is not limited to, methyl, ethyl, propyl, isopropyl, n-butyl, sec-butyl, isobutyl, t-butyl, pentyl isomers, hexyl isomers, cyclopropyl, cyclobutyl, cyclopentyl, cyclohexyl, and combinations thereof having from 1–6 carbon atoms, etc.

The above compounds of the present invention may be prepared by methods that are known in the art or according to the working examples below. The compounds, below, are especially preferred representative, of the compounds of the present invention.

7-[2-oxo-6-((E)-3-oxo-oct-1-enyl)-piperidin-1-yl]-hept-5-ynoic acid methyl ester
7-[2-oxo-6-((E)-3-oxo-oct-1-enyl)-piperidin-1-yl]-hept-5-ynoic acid
(Z)-7-[2-oxo-6-((E)-3-oxo-oct-1-enyl)-piperidin-1-yl]-hept-5-enoic acid methyl ester
(Z)-7-[2-oxo-6-((E)-3-oxo-oct-1-enyl)-piperidin-1-yl]-hept-5-enoic acid
7-[2-oxo-6-(3-oxo-octyl)-piperidin-1-yl]-heptanoic acid methyl ester
7-[2-oxo-6-(3-oxo-octyl)-piperidin-1-yl]-heptanoic acid
7-[2-(3-hydroxy-octyl)-6-oxo-piperidin-1-yl]-heptanoic acid methyl ester
7-[2-(3-hydroxy-octyl)-6-oxo-piperidin-1-yl]-heptanoic acid
(Z)-7-[2-((E)-3-hydroxy-oct-1-enyl)-6-oxo-piperidin-1-yl]-hept-5-enoic acid methyl ester
(Z)-7-[2-((E)-3-hydroxy-oct-1-enyl)-6-oxo-piperidin-1-yl]-hept-5-enoic acid
7-[2-oxo-6-((E)-3-oxo-oct-1-enyl)-piperidin-1-yl]-heptanoic acid methyl ester
7-[2-oxo-6-((E)-3-oxo-oct-1-enyl)-piperidin-1-yl]-heptanoic acid
7-[2-((E)-3-hydroxy-oct-1-enyl)-6-oxo-piperidin-1-yl]-heptanoic acid methyl ester
7-[2-((E)-3-hydroxy-oct-1-enyl)-6-oxo-piperidin-1-yl]-heptanoic acid
7-[2-oxo-6-((E)-3-oxo-4-phenyl-but-1-enyl)-piperidin-1-yl]-heptanoic acid methyl ester
7-[2-oxo-6-((E)-3-oxo-4-phenyl-but-1-enyl)-piperidin-1-yl]-heptanoic acid
7-[2-((E)-3-hydroxy-4-phenyl-but-1-enyl)-6-oxo-piperidin-1-yl]-heptanoic acid methyl ester
7-[2-((E)-3-hydroxy-4-phenyl-but-1-enyl)-6-oxo-piperidin-1-yl]-heptanoic acid
7-[2-(3-hydroxy-4-phenyl-butyl)-6-oxo-piperidin-1-yl]-heptanoic acid methyl ester
7-[2-(3-hydroxy-4-phenyl-butyl)-6-oxo-piperidin-1-yl]-heptanoic acid
7-[2-oxo-6-(3-oxo-4-phenyl-butyl)-piperidin-1-yl]-heptanoic acid methyl ester
7-[2-oxo-6-(3-oxo-4-phenyl-butyl)-piperidin-1-yl]-heptanoic acid
7-[2-oxo-6-((E)-3-oxo-4-phenyl-but-1-enyl)-piperidin-1-yl]-hept-5-ynoic acid methyl ester
7-[2-oxo-6-((E)-3-oxo-4-phenyl-but-1-enyl)-piperidin-1-yl]-hept-5-ynoic acid
(Z)-7-[2-oxo-6-((E)-3-oxo-4-phenyl-but-1-enyl)-piperidin-1-yl]-hept-5-enoic acid methyl ester
(Z)-7-[2-oxo-6-((E)-3-oxo-4-phenyl-but-1-enyl)-piperidin-1-yl]-hept-5-enoic acid
(Z)-7-[2-((E)-3-hydroxy-4-phenyl-but-1-enyl)-6-oxo-piperidin-1-yl]-hept-5-enoic acid methyl ester
(Z)-7-[2-((E)-3-hydroxy-4-phenyl-but-1-enyl)-6-oxo-piperidin-1-yl]-hept-5-enoic acid
7-[(R)-2-((E)-3-Hydroxy-4-phenyl-but-1-enyl)-6-oxo-piperidin-1-yl]-heptanoic acid methyl ester
7-[(R)-2-((E)-3-Hydroxy-4-phenyl-but-1-enyl)-6-oxo-piperidin-1-yl]-heptanoic acid
7-[(R)-2-((E)-3-Hydroxy-oct-1-enyl)-6-oxo-piperidin-1-yl]-heptanoic acid methyl ester
7-[(R)-2-((E)-3-Hydroxy-oct-1-enyl)-6-oxo-piperidin-1-yl]-heptanoic acid
7-[(R)-2-(3-Hydroxy-octyl)-6-oxo-piperidin-1-yl]-heptanoic acid methyl ester
7-[(R)-2-(3-Hydroxy-octyl)-6-oxo-piperidin-1-yl]-heptanoic acid
7-[(R)-2-((E)-3-Hydroxy-oct-1-enyl)-6-oxo-piperidin-1-yl]-hept-5-ynoic acid methyl ester
(R)-1-(7-hydroxy-hept-2-ynyl)-6-((E)-3-hydroxy-oct-1-enyl)-piperidin-2-one
(Z)-7-[(R)-2-((E)-3-Hydroxy-oct-1-enyl)-6-oxo-piperidin-1-yl]-hept-5-enoic acid methyl ester
(Z)-7-[(R)-2-((E)-3-Hydroxy-oct-1-enyl)-6-oxo-piperidin-1-yl]-hept-5-enoic acid
(Z)-7-[(R)-2-((E)-3-Hydroxy-4-phenyl-but-1-enyl)-6-oxo-piperidin-1-yl]-hept-5-enoic acid methyl ester
(Z)-7-[(R)-2-((E)-3-Hydroxy-4-phenyl-but-1-enyl)-6-oxo-piperidin-1-yl]-hept-5-enoic acid
7-[(R)-2-((E)-3-Hydroxy-4-phenyl-but-1-enyl)-6-oxo-piperidin-1-yl]-hept-5-ynoic acid methyl ester
7-[(R)-2-((E)-3-Hydroxy-4-phenyl-but-1-enyl)-6-oxo-piperidin-1-yl]-hept-5-ynoic acid
7-[(R)-2-((E)-3-Hydroxy-4-phenyl-but-1-enyl)-6-oxo-piperidin-1-yl]-heptanoic acid isopropyl ester
7-[(R)-2-((E)-3-Hydroxy-4-phenyl-but-1-enyl)-6-oxo-piperidin-1-yl]-heptanoic acid amide
7-[(R)-2-((E)-3-Hydroxy-4-phenyl-but-1-enyl)-6-oxo-piperidin-1-yl]-heptanoic acid isopropyl ester (faster eluting diastereomer by HPLC)
7-[(R)-2-((E)-3-Hydroxy-4-phenyl-but-1-enyl)-6-oxo-piperidin-1-yl]-heptanoic acid isopropyl ester (slower eluting diastereomer by HPLC).

One embodiment comprises derivatives of

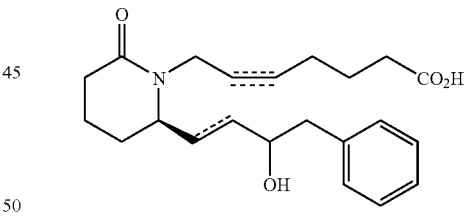

or a derivative thereof, wherein a dotted line indicates the presence or absence of a bond, and wherein said derivative has a structure as shown above except that from 1 to 2 alterations are made to the α chain and/or the ω chain, an alteration consisting of a. adding, removing, or substituting a non-hydrogen atom,
b. converting an alcohol to a carbonyl,
g. converting a CO$_2$H to a moiety selected from the group consisting of CONMe$_2$, CONHMe, CONHEt, CON(OCH$_3$)CH$_3$, CONH$_2$, CON(CH$_2$CH$_2$OH)$_2$, CONH(CH$_2$CH$_2$OH), CH$_2$OH, P(O)(OH)$_2$, CONHSO$_2$CH$_3$, SO$_2$NH$_2$, SO$_2$N(CH$_3$)$_2$, SO$_2$NH(CH$_3$),

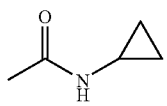 , and 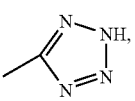

c. converting a phenyl moiety to a pyridinyl, furyl, or thienyl moiety, or d. adding a substituent comprising from 1 to 3 non-hydrogen atoms to an aromatic or a heteroaromatic ring;

Another embodiment comprises derivatives of

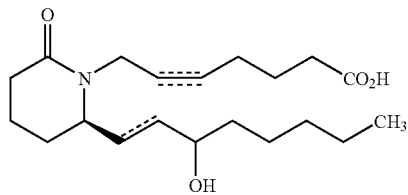

or a derivative thereof, wherein a dotted line indicates the presence or absence of a bond, and wherein said derivative has a structure as shown above except that from 1 to 2 alterations are made to the α chain and/or the ω chain, an alteration consisting of a. adding, removed, or substituting a non-hydrogen atom, b. converting an alcohol to a carbonyl, or h. converting a $CO_2H$ to a moiety selected from the group consisting of $CONMe_2$, CONHMe, CONHEt, CON($OCH_3$)$CH_3$, $CONH_2$, $CON(CH_2CH_2OH)_2$, CONH($CH_2CH_2OH$), $CH_2OH$, $P(O)(OH)_2$, $CONHSO_2CH_3$, $SO_2NH_2$, $SO_2N(CH_3)_2$, $SO_2NH(CH_3)$,

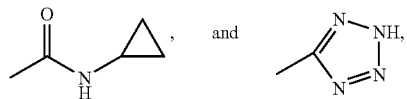

or a pharmaceutically acceptable salt or a prodrug thereof.

The actual compounds depicted in these structures as well as their derivatives as defined herein are contemplated in these embodiments.

Thus, the following compounds are contemplated, as well as their derivatives, which will be described in detail hereafter.

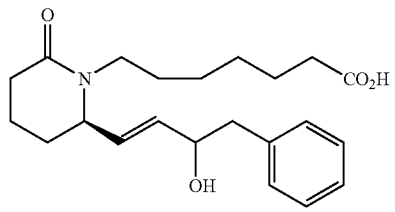

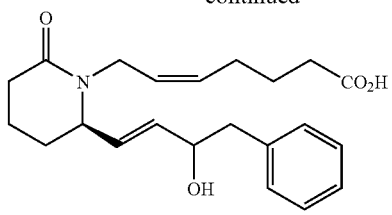

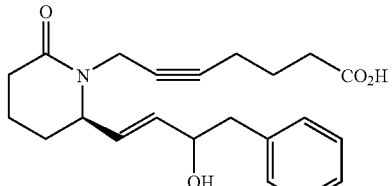

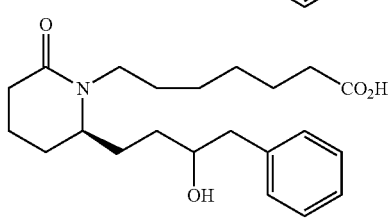

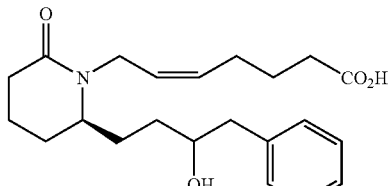

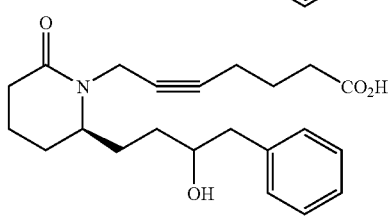

Salts, and prodrugs of the compounds depicted in the structures as well as salts and prodrugs of the derivatives are also contemplated.

The following compounds are also contemplated, as well as their derivatives, which will be described in detail hereafter.

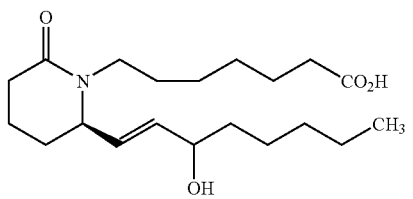

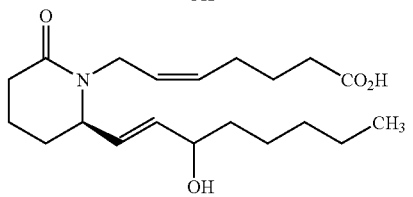

-continued

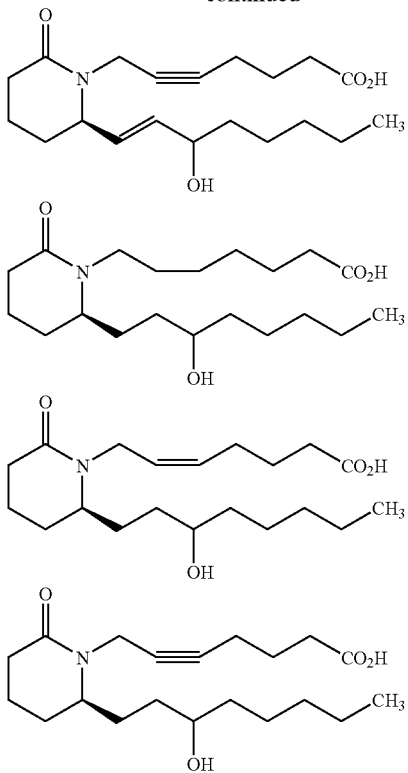

Salts, and prodrugs of the compounds depicted in the structures as well as salts and prodrugs of the derivatives are also contemplated.

In making reference to a derivative and alterations to the structure shown above, it should be emphasized that making alterations and forming derivatives is strictly a mental exercise used to define a set of chemical compounds, and has nothing to do with whether said alteration can actually be carried out in the laboratory, or whether a derivative can be prepared by an alteration described. However, whether the derivative can be prepared via any designated alteration or not, the differences between the derivatives and the aforementioned structure are such that a person of ordinary skill in the art could prepare the derivatives disclosed herein using routine methods known in the art without undue experimentation.

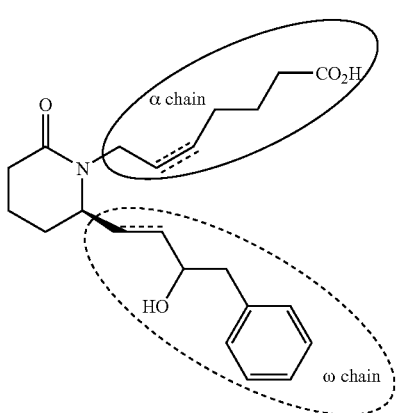

-continued

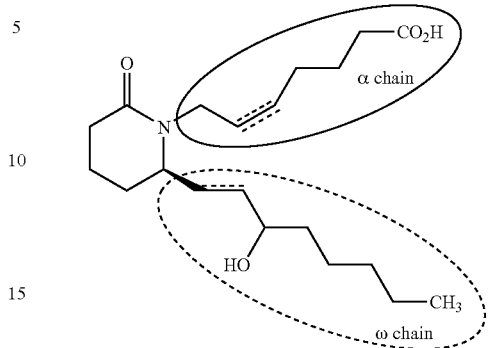

The α chain is the group in the solid circle in the labeled structures above. The ω chain is the group in the dashed circle in the labeled structures above. Thus, in these embodiments said derivative may be different from the formulae above at the α chain, while no alteration is made to the ω chain, as for example, in the structures shown below.

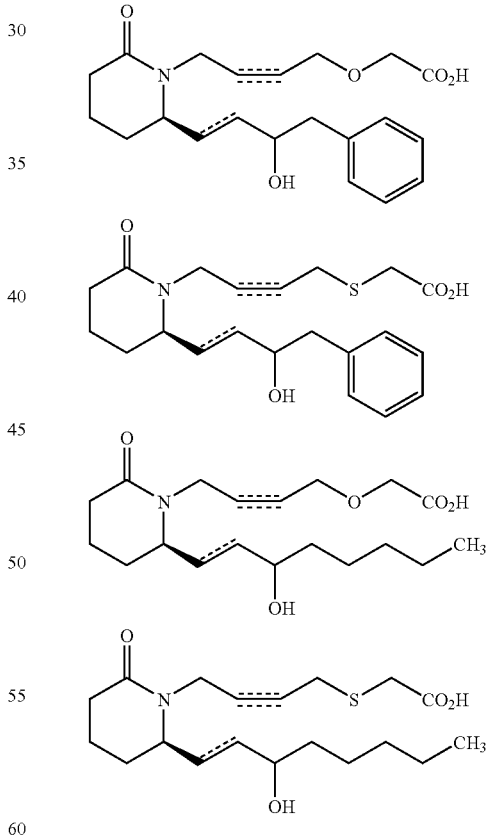

Pharmaceutically acceptable salts and prodrugs of these compounds are also contemplated.

The derivatives may also be different from the formulae above in the ω chain, while no alteration is made to the α chain, as shown in the examples below.

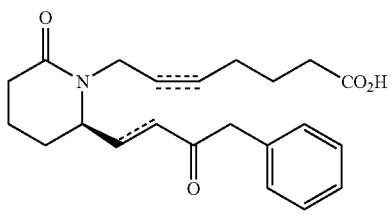

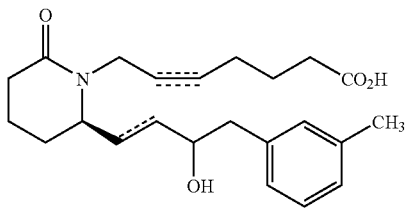

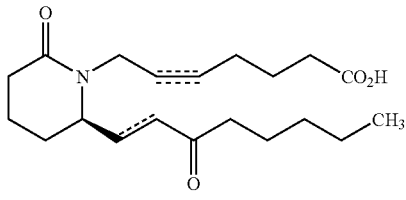

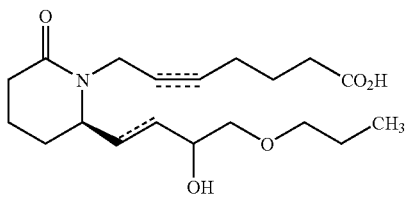

Pharmaceutically acceptable salts and prodrugs of these compounds are also contemplated.

Alternatively, the derivatives may be different in both the α and ω chains, as shown in the examples below.

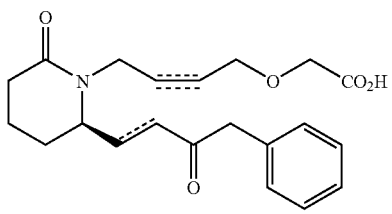

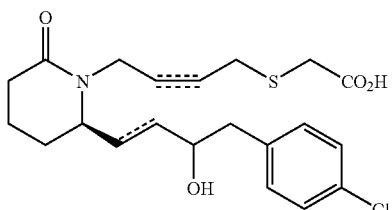

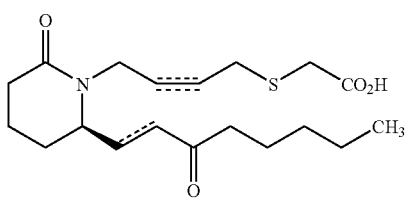

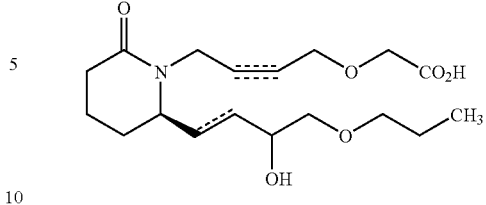

Pharmaceutically acceptable salts and prodrugs of these compounds are also contemplated.

Changes to the structure can take several forms, if a non-hydrogen atom is added, the structure is changed by adding the atom, and any required hydrogen atoms, but leaving the remaining non-hydrogen atoms unchanged, such as in the examples shown below, with the added atoms in bold type.

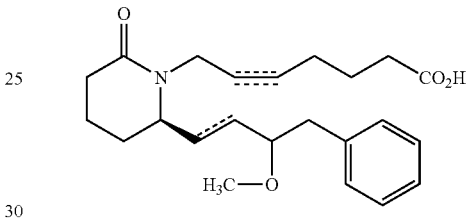

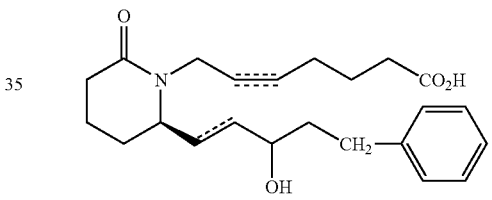

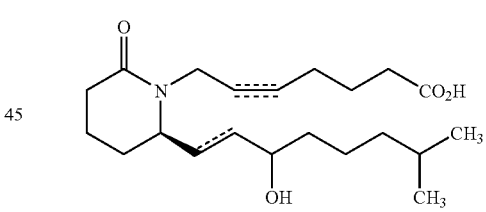

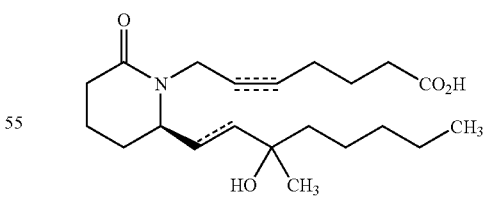

Pharmaceutically acceptable salts and prodrugs of these compounds are also contemplated.

While adding a methyl group or a methylene group to the molecule is a useful alteration in many situations, it may also be useful to add other non-hydrogen atoms such as sulfur or oxygen, such as in the examples below.

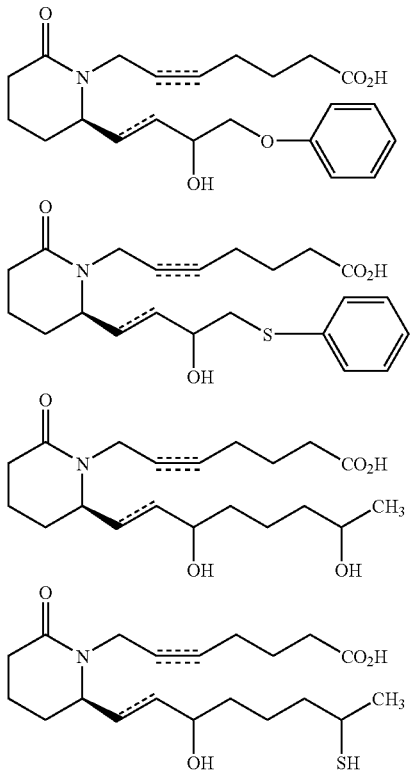

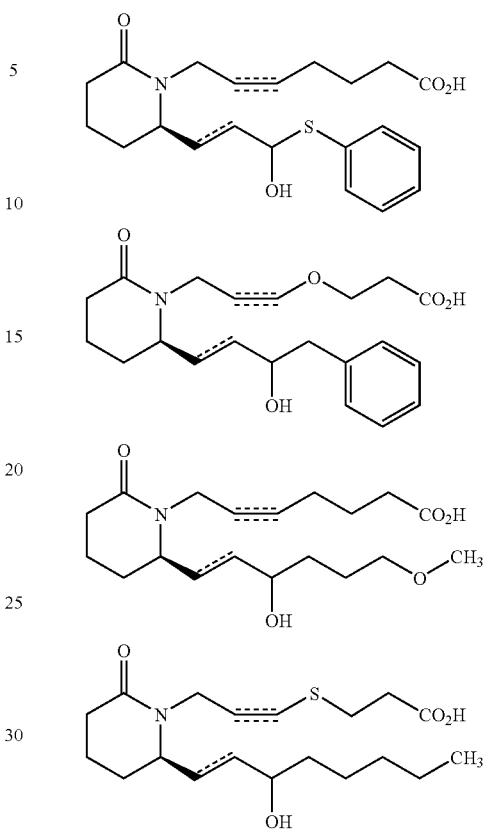

Pharmaceutically acceptable salts and prodrugs of these compounds are also contemplated.

If a non-hydrogen atom is removed, the structure is changed by removing the atom, and any required hydrogen atoms, but leaving the remaining non-hydrogen atoms unchanged, such as in the examples shown below, with the previous location of the missing atoms indicated by arrows.

Pharmaceutically acceptable salts and prodrugs of these compounds are also contemplated.

Another possible alteration is the conversion of an alcohol to a carbonyl, such as in the examples below.

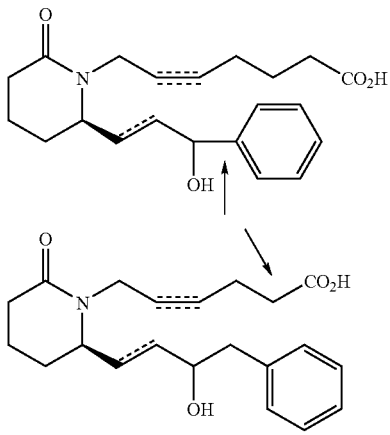

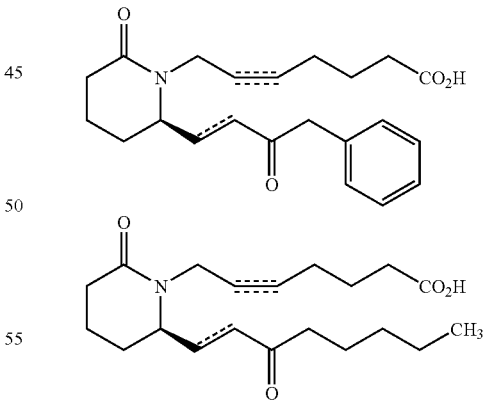

Pharmaceutically acceptable salts and prodrugs of these compounds are also contemplated.

If a non-hydrogen atom is substituted, the non-hydrogen atom is replaced by a different non-hydrogen atom, with any necessary adjustment made to the number hydrogen atoms, such as in the examples shown below, with the substituted atoms in bold type.

Pharmaceutically acceptable salts and prodrugs of these compounds are also contemplated.

Another alteration includes converting a $CO_2H$ to a moiety selected from the group consisting of $CONMe_2$, $CONHMe$, $CONHEt$, $CON(OCH_3)CH_3$, $CONH_2$, $CON(CH_2CH_2OH)_2$, $CONH(CH_2CH_2OH)$, $CH_2OH$, $P(O)(OH)_2$, $CONHSO_2CH_3$, $SO_2NH_2$, $SO_2N(CH_3)_2$, $SO_2NH(CH_3)$,

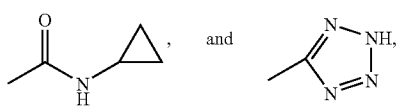
such as in the examples below.
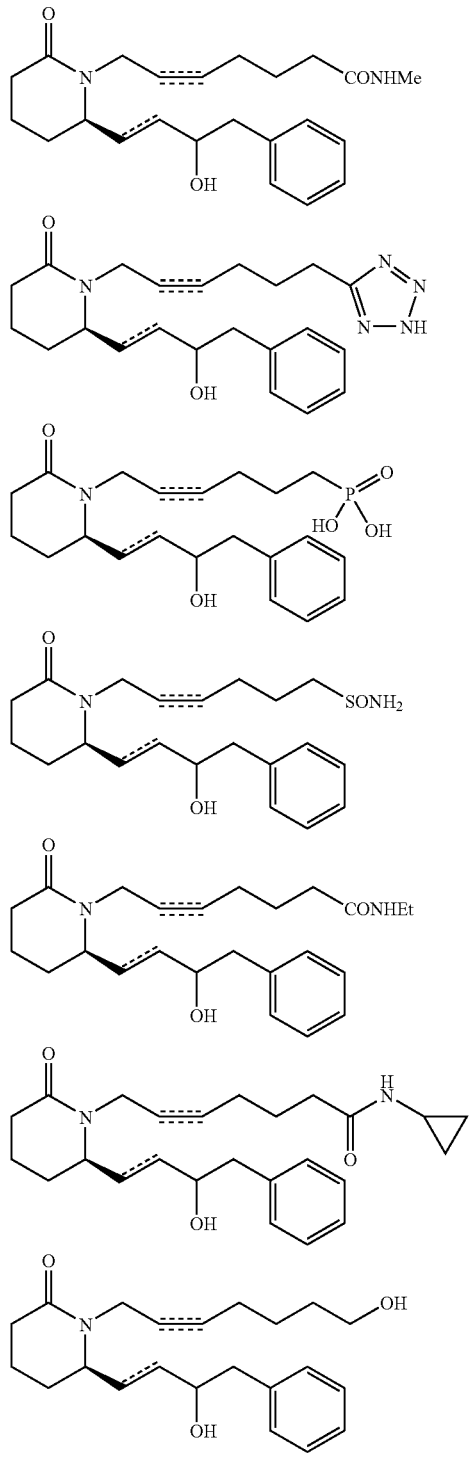
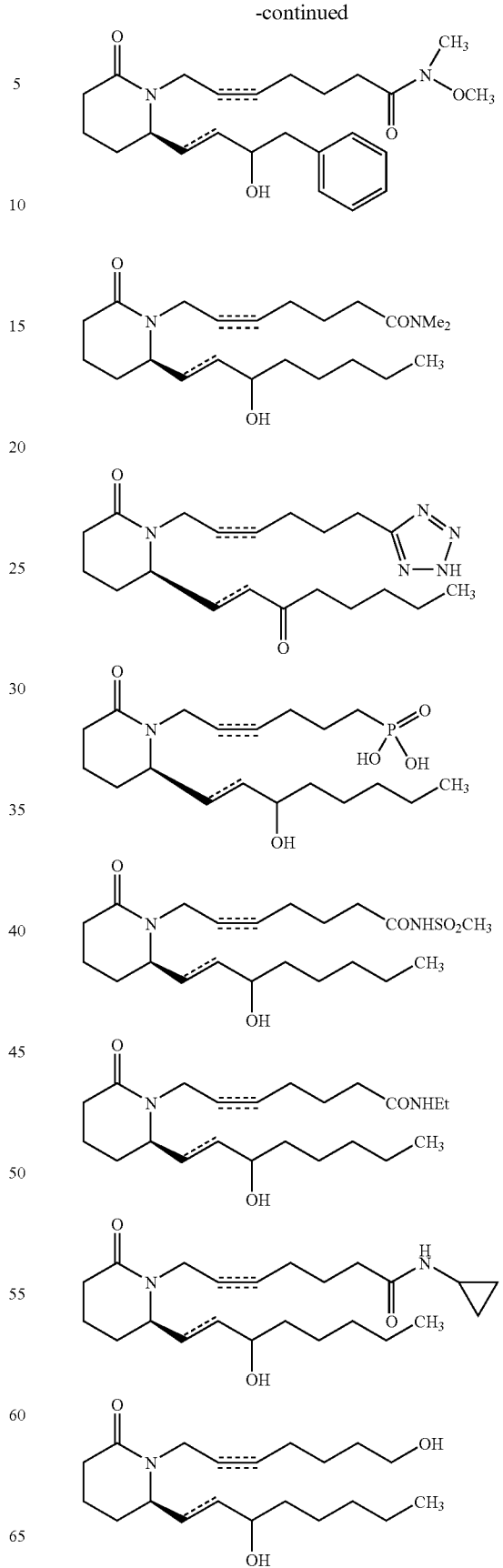

-continued

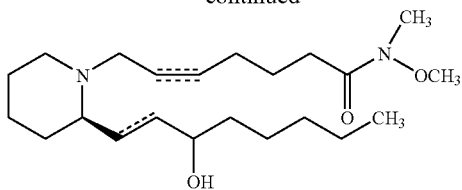

Pharmaceutically acceptable salts and prodrugs of these compounds are also contemplated.

The tetrazole group,

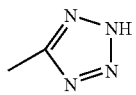

has two tautomeric forms, which can rapidly interconvert in aqueous or biological media, and are thus equivalent to one another. The tautomer of the tetrazole shown above is shown below.

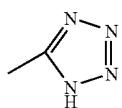

For the purposes disclosed herein, all tautomeric forms should be considered equivalent in every way. If the tetrazole has a substituent or some other symmetry breaking feature, more than two tautomeric forms may exist. These are also considered to be equivalent to one another.

Another alteration consists of converting a phenyl moiety to a pyridinyl, furyl, or thienyl moiety, such as in the examples below.

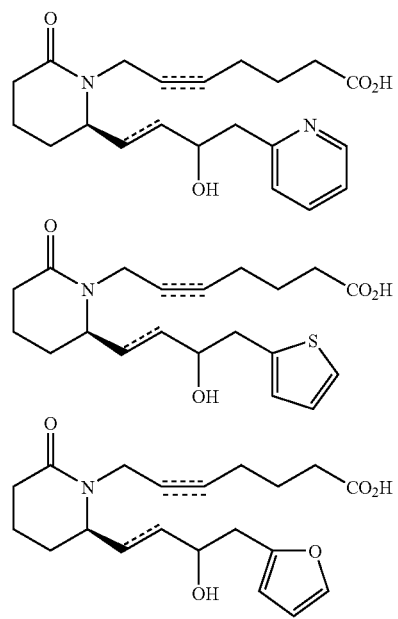

Pharmaceutically acceptable salts and prodrugs of these compounds are also contemplated.

Another alteration consists of adding a substituent comprising from 1 to 3 non-hydrogen atoms to an aromatic or a heteroaromatic ring, as in the examples below.

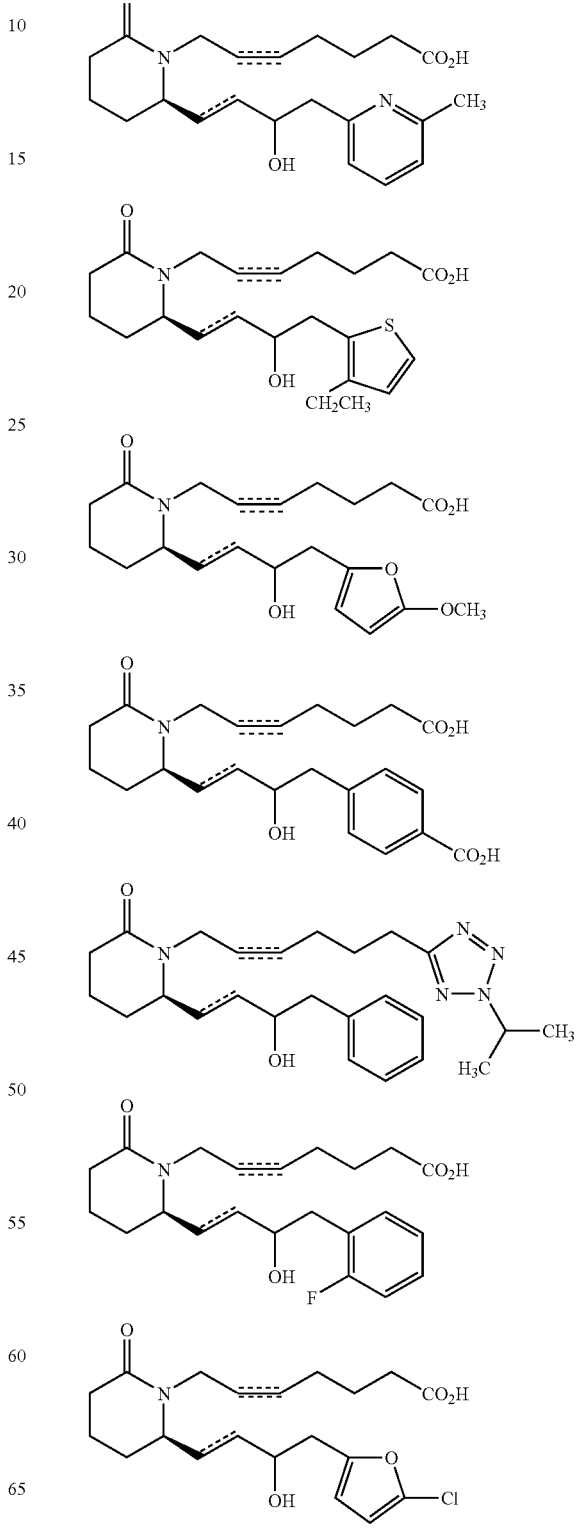

-continued

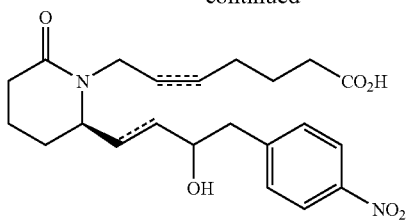

Pharmaceutically acceptable salts and prodrugs of these compounds are also contemplated.

If a derivative could reasonably be construed to consist of a different number of alterations, the derivative is considered to have the lowest reasonable number of alterations. For example, the compound shown below, having the modified portion of the molecule in bold, could be reasonably construed to have 1 or 2 alterations relative to the defined structure.

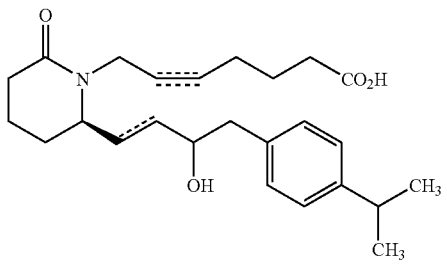

By one line of reasoning, the first alteration would be to add an ethyl substituent to the phenyl ring. The second alteration would be to add a carbon atom, with its accompanying hydrogen atoms to the ethyl substituent. By a second line of reasoning, the derivative would be obtained by simply adding an isopropyl group to the phenyl ring. In accordance with the rule established above, the compound above is defined as having 1 alteration. Thus, an additional alteration could be made to the structure to obtain the compounds such as the examples shown below.

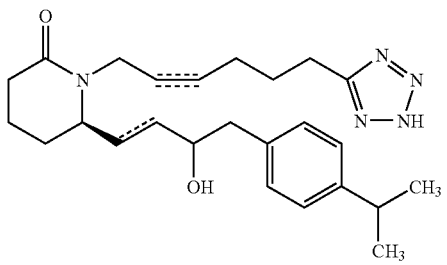

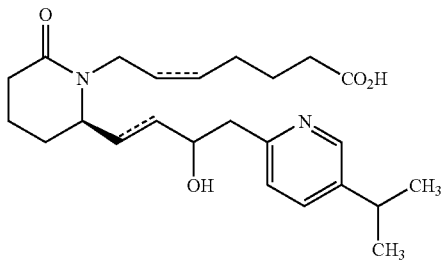

Pharmaceutically acceptable salts and prodrugs of these compounds are also contemplated.

Some alterations are considered to render particularly useful compounds. While not intending to limit the scope of the invention in any way, in certain compounds, an oxygen atom or a sulfur atom is substituted for a carbon atom, such as in the examples below. In particular, it is useful for this alteration to occur in the α chain, as in the case in 5 of the 6 examples shown below.

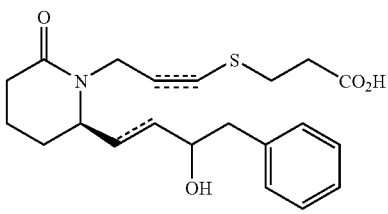

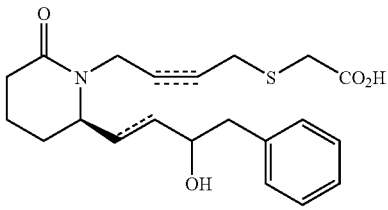

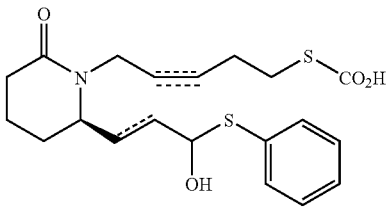

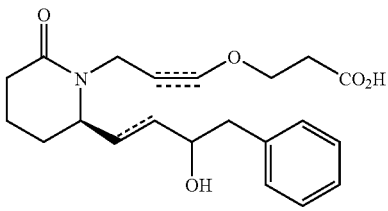

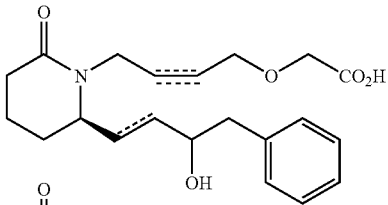

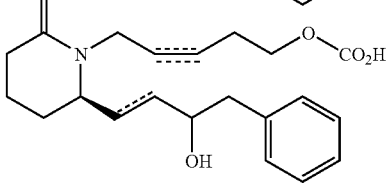

Pharmaceutically acceptable salts and prodrugs of these compounds are also contemplated.

The addition of $CH_2$, O, or S to the c chain is also considered to yield particular useful compounds such as the ones below.

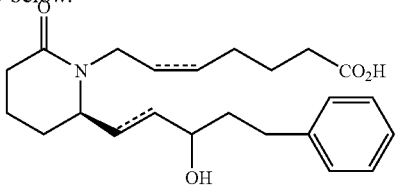

-continued

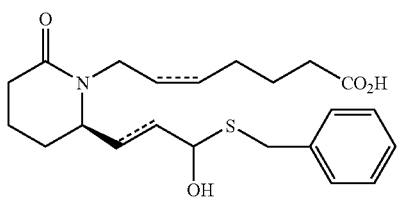

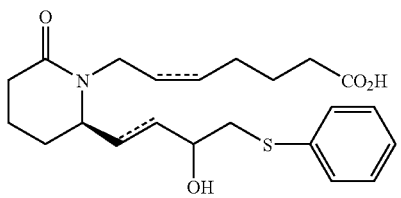

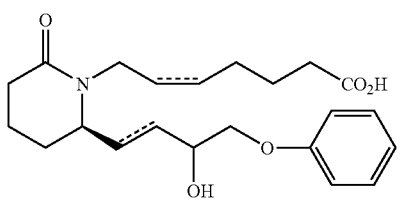

Pharmaceutically acceptable salts and prodrugs of these compounds are also contemplated.

While not intending to limit the scope of the invention in any way, particularly useful compounds are obtained when certain alterations are made twice. Alterations that are useful when made twice are the substitution of a carbon atom with a sulfur atom or an oxygen atom and the addition of a substituent to a phenyl ring.

Examples of compounds obtained by two substitutions of a carbon atom with a sulfur atom or an oxygen atom are shown below.

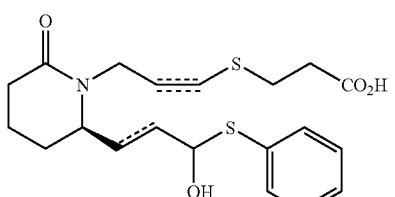

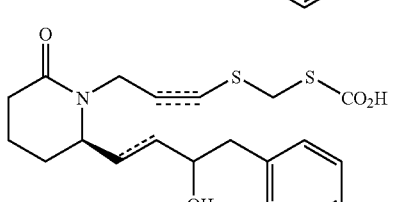

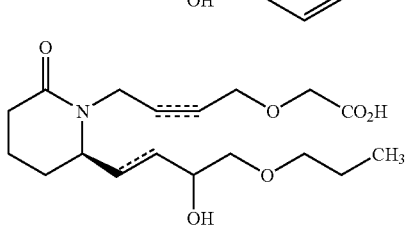

-continued

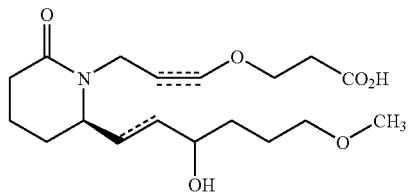

Pharmaceutically acceptable salts and prodrugs of these compounds are also contemplated.

Examples of compound obtained by two additions of a substituent to a phenyl ring are shown below.

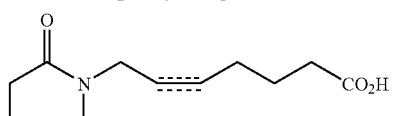

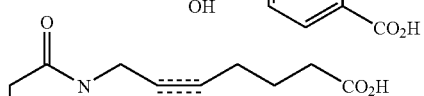

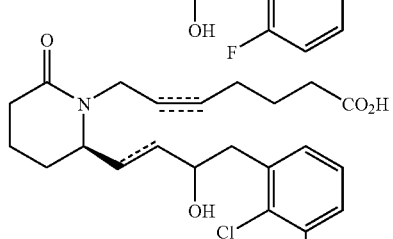

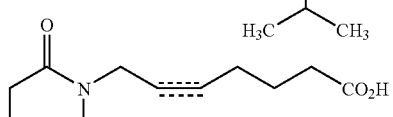

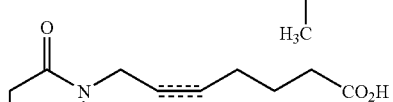

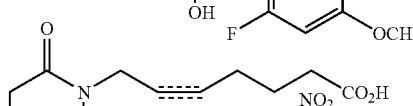

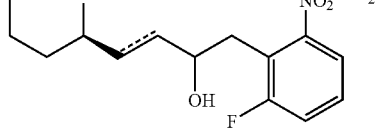

Pharmaceutically acceptable salts and prodrugs of these compounds are also contemplated.

While not intending to limit the scope of the invention in any way, certain combinations of alterations also render particularly useful compounds. In particular, the combination of substitution of carbon with sulfur or oxygen with an alteration to the phenyl ring gives particularly useful compounds. For example, substitution of a carbon atom with sulfur or oxygen and the addition of a substituent to a phenyl ring yields particularly useful compounds such as the ones shown below.

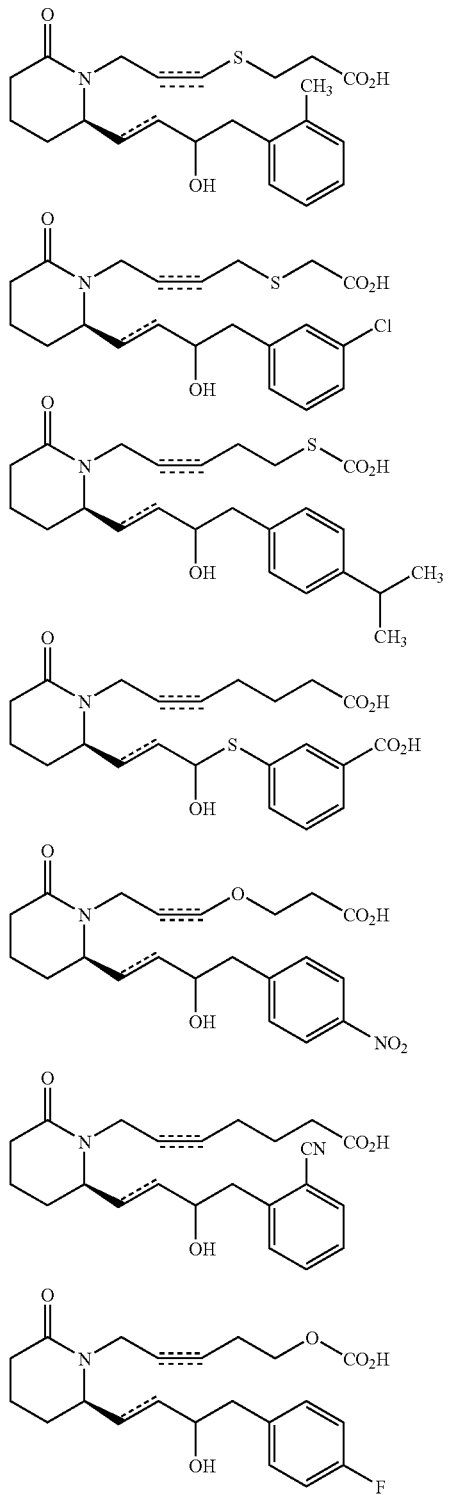

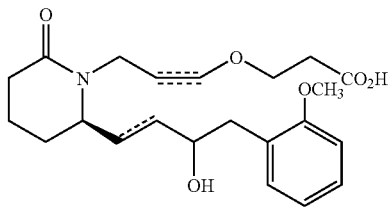

Pharmaceutically acceptable salts and prodrugs of these compounds are also contemplated.

Another combination which yields useful compounds is the substitution of phenyl with pyridinyl, furyl, or thienyl and the substitution of a carbon atom with sulfur or oxygen such as in the examples below.

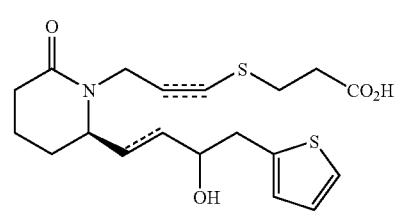

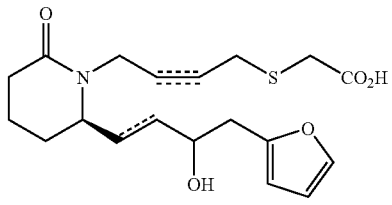

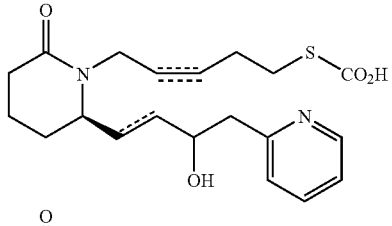

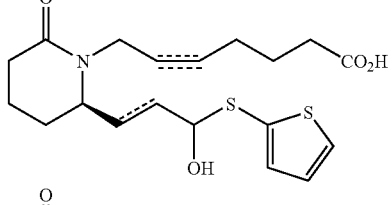

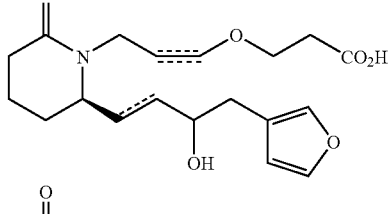

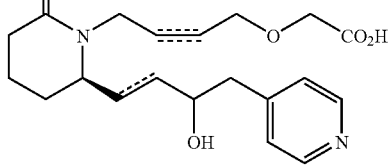

-continued

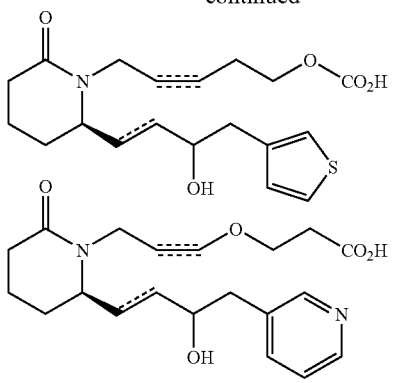

Pharmaceutically acceptable salts and prodrugs of these compounds are also contemplated.

Another combination which yields useful compounds is the substitution of phenyl with pyridinyl, furyl, or thienyl and the addition of a substituent to the heteroaryl ring such as in the examples below.

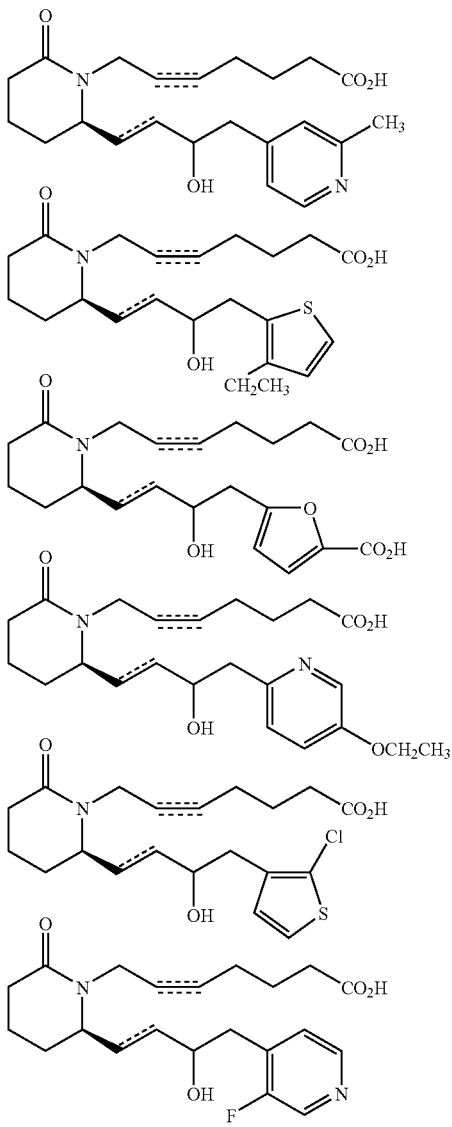

-continued

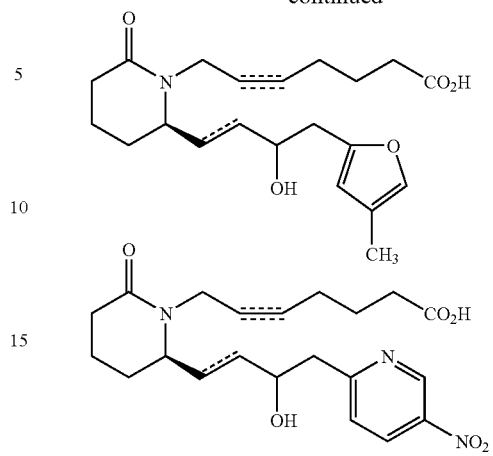

Pharmaceutically acceptable salts and prodrugs of these compounds are also contemplated.

Pharmaceutical compositions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

This invention is further illustrated by the following non-limiting Examples.

EXAMPLE 1

7-[2-Oxo-6-((E)-3-oxo-oct-1-enyl)-piperidin-1-yl]-hept-5-ynoic Acid Methyl Ester Step 1. 6-(tert-Butyl-dimethyl-silanyloxymethyl)-piperidin-2-one Imidazole (1.16 g, 17.0 mmol) and tert-butyldimethylsilyl chloride (1.18 g, 7.85 mmol) were added sequentially to a solution of racemic 6-hydroxymethyl-piperidin-2-one (prepared from racemic α-aminoadipic acid according to Huang, et al., *Synth. Commun.* 1989, 19, 3485–3496, 921 mg, 7.14 mmol) in DMF (10 mL) at 0° C. The reaction mixture was allowed to warm to rt and was stirred at rt for 17 h. Benzene and EtOAc (3:7, 200 mL) was added and the solution was washed with brine (3×50 mL). The organic phase was dried ($Na_2SO_4$), filtered and concentrated in vacuo. Purification of the residue by flash column chromatography on silica gel ($CH_2Cl_2 \rightarrow 3\%$ MeOH/$CH_2Cl_2$, gradient) afforded 1.53 g (88%) of 6-(tert-butyl-dimethyl-silanyloxymethyl)-piperidin-2-one as a white solid.

Step 2. 7-[2-tert-Butyl-dimethyl-silanyloxymethyl)-6-oxo-piperidin-1-yl]-hept-5-ynoic Acid Methyl Ester Sodium hydride (60% dispersion in oil, 219 mg, 5.27 mmol) was added to a solution of 6-(tert-butyl-dimethyl-silanyloxymethyl)-piperidin-2-one (1.27 g, 5.21 mmol) in DMF (10 mL) at rt. After 1 h, methyl 7-iodohept-5-ynoate (1.52 g, 5.73 mmol) in DMF (2 mL) was added via cannula. After 18 h at rt, the reaction was quenched by the addition of aqueous HCl (0.5 M, 15 mL) and the mixture was extracted with EtOAc (3×30 mL). The combined organic phase was washed with brine (3×20 mL), dried ($Na_2SO_4$), filtered and concentrated in vacuo. Purification of the residue by flash column chromatography on silica gel ($CH_2Cl_2 \rightarrow 40\%$ EtOAc/$CH_2Cl_2$, gradient) afforded 1.04 g (53%) of 7-[2-tert-butyl-dimethyl-silanyloxymethyl)-6-oxo-piperidin-1-yl]-hept-5-ynoic acid methyl ester.

Step 3. 7-(2-Hydroxymethyl-6-oxo-piperidin-1-yl)-hept-5-ynoic Acid Methyl Ester

Hydrogen fluoride-pyridine (2.5 mL) was added to a solution of 7-[2-tert-Butyl-dimethyl-silanyloxymethyl)-6-oxo-piperidin-1-yl]-hept-5-ynoic acid methyl ester (1.07 g, 2.80 mmol) in acetonitrile (5.0 mL) in a plastic scintillation vial. After 3.5 h at rt, the reaction was quenched with saturated aqueous $NaHCO_3$ (70 mL) and the mixture was extracted with EtOAc (3×50 mL). The combined organic phase was washed with brine (50 mL), dried ($Na_2SO_4$), filtered and concentrated in vacuo. Purification of the residue by flash column chromatography on silica gel ($CH_2Cl_2 \rightarrow 3\%$ MeOH/$CH_2Cl_2$, gradient) afforded 724 mg (97%) of 7-(2-hydroxymethyl-6-oxo-piperidin-1-yl)-hept-5-ynoic acid methyl ester.

Step 4. 7-(2-Formyl-6-oxo-piperidin-1-yl)-hept-5-ynoic Acid Methyl Ester 1-(3-(Dimethylaminopropyl)-3-ethylcarbodiimide hydrochloride (EDCI, 530 mg, 2.76 mmol) and DMSO (0.26 mL, 3.68 mmol) were added sequentially to a solution of 7-(2-hydroxymethyl-6-oxo-piperidin-1-yl)-hept-5-ynoic acid methyl ester (246 mg, 0.92 mmol) in benzene (7.0 mL) at rt. The mixture was cooled to 0° C. and pyridinium trifluoroacetate (196 mg, 1.01 mmol) was added. The reaction was allowed to warm to rt and then was stirred at rt for 2.5 h. The solution was decanted from the oily residue and the residue was washed with benzene (3×5 mL). The combined benzene phases were concentrated in vacuo to afford crude 7-(2-formyl-6-oxo-piperidin-1-yl)-hept-5-ynoic acid methyl ester that was used without further purification.

Step 5. 7-[2-Oxo-6-((E)-3-oxo-oct-1-enyl)-piperidin-1-yl]-hept-5-ynoic Acid Methyl Ester Sodium hydride (60% dispersion in oil, 37 mg, 0.91 mmol) was added to a solution of dimethyl 2-oxoheptylphosphonate (217 mg, 0.83 mmol) in THF (4 mL) at 0° C. After 10 min at 0° C., the solution was allowed to warm to rt. After 50 min at rt, the solution was recooled to 0° C. and 7-(2-formyl-6-oxo-piperidin-1-yl)-hept-5-ynoic acid methyl ester (crude from previous reaction, ~0.92 mmol) in THF (2 mL) was added via cannula. The reaction was allowed to warm to rt. After 18 h at rt, the reaction was quenched with acetic acid and water (1:1, 15 mL) and extracted with EtOAc (3×40 mL). The combined organic phase was washed with brine (50 mL), dried ($Na_2SO_4$), filtered and concentrated in vacuo. Purification of the residue by flash column chromatography on silica gel (10% →50% EtOAc/$CH_2Cl_2$, gradient) afforded 175 mg (58%) of the title compound.

EXAMPLE 2

7-[2-Oxo-6-((E)-3-oxo-oct-1-enyl)-piperidin-1-yl]-hept-5-ynoic Acid

Rabbit liver esterase (134 units/mg, 3 mg) was added to a solution of 7-[2-oxo-6-((E)-3-oxo-oct-1-enyl)-piperidin-1-yl]-hept-5-ynoic acid methyl ester (18 mg, 0.45 mmol) in acetonitrile (0.3 mL) and pH 7.2 phosphate buffer (3.0 mL). After 18.5 h, acetonitrile (10 mL) was added and the reaction mixture was concentrated to dryness in vacuo. Purification of the residue by flash column chromatography on silica gel ($CH_2Cl_2 \rightarrow 3\%$ $MeOH/CH_2Cl_2$, gradient) afforded 17 mg (97%) of the title compound.

EXAMPLE 3

(Z)-7-[2-Oxo-6-((E)-3-oxo-oct-1-enyl)-piperidin-1-yl]-hept-5-enoic Acid Methyl Ester A 50 mL round bottom flask was charged with nickel (II) chloride (273 mg, 2.10 mmol) and sodium borohydride (40 mg, 1.05 mmol), then 95% ethanol (2.0 mL) was added. The mixture immediately turned black. After 15 min at rt, ethylene diamine (0.23 mL, 3.36 mmol) was added. After another 15 min at rt, 7-[2-oxo-6-((E)-3-oxo-oct-1-enyl)-piperidin-1-yl]-hept-5-ynoic acid methyl ester (152 mg, 0.42 mmol) in 95% ethanol (2.0 mL) was added via cannula. A hydrogen atmosphere was established by evacuating and refilling with hydrogen (3×) and the reaction mixture was stirred under a balloon of hydrogen for 19 h. The reaction mixture was filtered through celite, washing with ethanol, and the filtrate was concentrated in vacuo. Purification of the resulting residue by flash column chromatography ($10 \rightarrow 50\%$ $EtOAc/CH_2Cl_2$, gradient) afforded 65 mg (43%) of the title compound.

EXAMPLE 4

(Z)-7-[2-Oxo-6-((E)-3-oxo-oct-1-enyl)-piperidin-1-yl]-hept-5-enoic Acid

In accordance with the procedure of example 2, (Z)-7-[2-oxo-6-((E)-3-oxo-oct-1-enyl)-piperidin-1-yl]-hept-5-enoic acid methyl ester (9 mg, 0.025 mmol) was converted into 5 mg (56%) of the title compound.

EXAMPLE 5

7-[2-Oxo-6-(3-oxo-octyl)-piperidin-1-yl]-heptanoic Acid Methyl Ester

Palladium on carbon (10 wt. %, 5 mg) was added to a solution of (Z)-7-[2-oxo-6-((E)-3-oxo-oct-1-enyl)-piperidin-1-yl]-hept-5-enoic acid methyl ester (40 mg, 0.11 mmol) in MeOH (3.0 mL). A hydrogen atmosphere was established by evacuating and refilling with hydrogen (3×) and the reaction mixture was stirred under a balloon of hydrogen for 19 h. The reaction mixture was filtered through celite, washing with MeOH, and the filtrate was concentrated in vacuo to afford 38 mg (94%) of the title compound.

EXAMPLE 6

7-[2-Oxo-6-(3-oxo-octyl)-piperidin-1-yl]-heptanoic Acid

In accordance with the procedure of example 2, 7-[2-oxo-6-(3-oxo-octyl)-piperidin-1-yl]-heptanoic acid methyl ester (14 mg, 0.038 mmol) was converted into 13 mg (97%) of the title compound.

EXAMPLE 7

7-[2-(3-Hydroxy-octyl)-6-oxo-piperidin-1-yl]-heptanoic Acid Methyl Ester

Sodium borohydride (24 mg, 0.63 mmol), followed by MeOH (2 drops), was added to a solution of 7-[2-oxo-6-(3-oxo-octyl)-piperidin-1-yl]-heptanoic acid methyl ester (23 mg, 0.063 mmol) in $CH_2Cl_2$ (1.0 mL) at 0° C. The mixture was allowed to warm to rt. After 4 h at rt, the reaction was quenched with HCl (1.0M aqueous) and extracted with EtOAc (3×10 mL). The combined organic phase was washed with saturated aqueous $NaHCO_3$ (15 mL) and brine (15 mL) then dried ($Na_2SO_4$), filtered and concentrated in vacuo. Purification of the residue by flash column chromatography on silica gel ($CH_2Cl_2 \rightarrow 3\%$ $MeOH/CH_2Cl_2$, gradient) afforded 14 mg (61%) of the title compound.

EXAMPLE 8

7-[2-(3-Hydroxy-octyl)-6-oxo-piperidin-1-yl]-heptanoic Acid

In accordance with the procedure of example 2, 7-[2-(3-hydroxy-octyl)-6-oxo-piperidin-1-yl]-heptanoic acid methyl ester (11.5 mg, 0.031 mmol) was converted into 6 mg (53%) of the title compound.

EXAMPLE 9

(Z)-7-[2-((E)-3-Hydroxy-oct-1-enyl)-6-oxo-piperidin-1-yl]-hept-5-enoic Acid Methyl Ester In accordance with the procedure of example 7, (Z)-7-[2-oxo-6-((E)-3-oxo-oct-1-enyl)-piperidin-1-yl]-hept-5-enoic acid methyl ester (32 mg, 0.087 mmol) was converted into 25 mg (78%) of the title compound.

EXAMPLE 10

(Z)-7-[2-((E)-3-Hydroxy-oct-1-enyl)-6-oxo-piperidin-1-yl]-hept-5-enoic Acid

In accordance with the procedure of example 2, (Z)-7-[2-((E)-3-hydroxy-oct-1-enyl)-6-oxo-piperidin-1-yl]-hept-5-enoic acid methyl ester (10 mg, 0.028 mmol) was converted into 5 mg (52%) of the title compound.

EXAMPLE 11

7-[2-Oxo-6-((E)-3-oxo-oct-1-enyl)-piperidin-1-yl]-heptanoic Acid Methyl Ester Step 1.
7-(2-Hydroxymethyl-6-oxo-piperidin-1-yl)-heptanoic Acid Methyl Ester Palladium on carbon (10 wt. %, 20 mg) was added to a solution of 7-(2-hydroxymethyl-6-oxo-piperidin-1-yl)-hept-5-ynoic acid methyl ester (180 mg, 0.67 mmol) in MeOH (6.0 mL). A hydrogen atmosphere was established by evacuating and refilling with hydrogen (3×) and the reaction mixture was stirred under a balloon of hydrogen for 23 h.

The reaction mixture was filtered through celite, washing with MeOH, and the filtrate was concentrated in vacuo to afford 184 mg (quant.) of 7-(2-hydroxymethyl-6-oxo-piperidin-1-yl)-heptanoic acid methyl ester.

Step 2. 7-(2-Formyl-6-oxo-piperidin-1-yl)-heptanoic Acid Methyl Ester

EDCI (212 mg, 1.10 mmol) and DMSO (0.10 mL, 1.48 mmol) were added sequentially to a solution of 7-(2-hydroxymethyl-6-oxo-piperidin-1-yl)-heptanoic acid methyl ester (100 mg, 0.37 mmol) in benzene (4.0 mL) at rt. The mixture was cooled to 0° C. and pyridinium trifluoroacetate (79 mg, 0.41 mmol) was added. The reaction was allowed to warm to rt and then was stirred at rt for 3.5 h. The solution was decanted from the oily residue and the residue was washed with benzene (3×3 mL). The combined benzene phases were concentrated in vacuo to afford crude 7-(2-formyl-6-oxo-piperidin-1-yl)-heptanoic acid methyl ester that was used without further purification.

Step 3. 7-[2-Oxo-6-((E)-3-oxo-oct-1-enyl)-piperidin-1-yl]-heptanoic Acid Methyl Ester Sodium hydride (60% dispersion in oil, 15 mg, 0.37 mmol) was added to a solution of dimethyl 2-oxoheptylphosphonate (87 mg, 0.33 mmol) in THF (2 mL) at 0° C. After 10 min at 0° C., the solution was allowed to warm to rt. After 1 h at rt, the solution was recooled to 0° C. and 7-(2-formyl-6-oxo-piperidin-1-yl)-heptanoic acid methyl ester (crude from previous reaction, ~0.37 mmol) in THF (2 mL) was added via cannula. The reaction was allowed to warm to rt. After 17 h at rt, the reaction was quenched with acetic acid (50% aqueous, 20 mL) and extracted with EtOAc (3×20 mL). The combined organic phase was washed with saturated aqueous $NaHCO_3$ (20 mL) and brine (20 mL), dried ($Na_2SO_4$), filtered and concentrated in vacuo. Purification of the residue by flash column chromatography on silica gel ($CH_2Cl_2 \rightarrow 2\%$ MeOH/$CH_2Cl_2$, gradient) afforded 128 mg (95%) of the title compound.

EXAMPLE 12

7-[2-Oxo-6-((E)-3-oxo-oct-1-enyl)-piperidin-1-yl]-heptanoic Acid

In accordance with the procedure of example 2, 7-[2-oxo-6-((E)-3-oxo-oct-1-enyl)-piperidin-1-yl]-heptanoic acid methyl ester (17 mg, 0.048 mmol) was converted into 2 mg (12%) of the title compound after flash column chromatography on silica gel ($CH_2Cl_2 \rightarrow 2\%$ MeOH/$CH_2Cl_2$, gradient) and preparative thin layer chromatography (silica, 5% MeOH/$CH_2Cl_2$).

EXAMPLE 13

7-[2-((E)-3-Hydroxy-oct-1-enyl)-6-oxo-piperidin-1-yl]-heptanoic Acid Methyl Ester Sodium borohydride (42 mg, 1.10 mmol), followed by MeOH (0.38 mL), was added to a solution of 7-[2-oxo-6-((E)-3-oxo-oct-1-enyl)-piperidin-1-yl]-heptanoic acid methyl ester (40 mg, 0.11 mmol) in $CH_2Cl_2$ (1.13 mL) at 0° C. The mixture was allowed to warm to rt. After 3 h at rt, the reaction was quenched with aqueous HCl (1.0M) and extracted with EtOAc (3×10 mL). The combined organic phase was washed with brine (20 mL) then dried ($Na_2SO_4$), filtered and concentrated in vacuo to afford 40 mg (99%) of the title compound.

EXAMPLE 14

7-[2-((E)-3-Hydroxy-oct-1-enyl)-6-oxo-piperidin-1-yl]-heptanoic Acid

In accordance with the procedure of example 2, 7-[2-((E)-3-Hydroxy-oct-1-enyl)-6-oxo-piperidin-1-yl]-heptanoic acid methyl ester (18 mg, 0.049 mmol) was converted into 6 mg (35%) of the title compound.

EXAMPLE 15

7-[2-Oxo-6-((E)-3-oxo-4-phenyl-but-1-enyl)-piperidin-1-yl]-heptanoic Acid Methyl Ester Sodium hydride (60% dispersion in oil, 12 mg, 0.32 mmol) was added to a solution of dimethyl 2-oxo-3-phenylpropylphosphonate (70 mg, 0.29 mmol) in THF (1.5 mL) at 0° C. After 10 min at 0° C., the solution was allowed to warm to rt. After 50 min at rt, the solution was recooled to 0° C. and 7-(2-formyl-6-oxo-piperidin-1-yl)-heptanoic acid methyl ester (crude, prepared in accordance with example 11, step 2, ~0.32 mmol) in THF (1.5 mL) was added via cannula. The reaction was allowed to warm to rt. After 18 h at rt, the reaction was quenched with acetic acid (50% aqueous, 20 mL) and extracted with EtOAc (3×20 mL). The combined organic phase was washed with saturated aqueous $NaHCO_3$ (30 mL) and brine (30 mL), dried ($Na_2SO_4$), filtered and concentrated in vacuo. Purification of the residue by flash column chromatography on silica gel ($CH_2Cl_2 \rightarrow 2\%$ MeOH/$CH_2Cl_2$, gradient) afforded 66 mg (59%) of the title compound.

EXAMPLE 16

7-[2-Oxo-6-((E)-3-oxo-4-phenyl-but-1-enyl)-piperidin-1-yl]-heptanoic Acid

In accordance with the procedure of example 2, 7-[2-oxo-6-((E)-3-oxo-4-phenyl-but-1-enyl)-piperidin-1-yl]-heptanoic acid methyl ester (7 mg, 0.018 mmol) was converted into 2 mg (30%) of the title compound.

EXAMPLE 17

7-[2-((E)-3-Hydroxy-4-phenyl-but-1-enyl)-6-oxo-piperidin-1-yl]-heptanoic Acid Methyl Ester Sodium borohydride (36 mg, 0.96 mmol), followed by MeOH (0.25 mL), was added to a solution of 7-[2-oxo-6-((E)-3-oxo-4-phenyl-but-1-enyl)-piperidin-1-yl]-heptanoic acid methyl ester (37 mg, 0.096 mmol) in $CH_2Cl_2$ (0.75 mL) at 0° C. The mixture was allowed to warm to rt. After 1.5 h at rt, the reaction was quenched with HCl (1.0M aqueous) and extracted with EtOAc (3×10 mL). The combined organic phase was washed with saturated aqueous $NaHCO_3$ (20 mL) and brine (20 mL) then dried ($Na_2SO_4$), filtered and concentrated in vacuo. Purification of the residue by flash column chromatography on silica gel ($CH_2Cl_2 \rightarrow 3\%$ MeOH/$CH_2Cl_2$, gradient) afforded 32 mg (86%) of the title compound.

EXAMPLE 18

7-[2-((E)-3-Hydroxy-4-phenyl-but-1-enyl)-6-oxo-piperidin-1-yl]-heptanoic Acid

In accordance with the procedure of example 2, 7-[2-((E)-3-hydroxy-4-phenyl-but-1-enyl)-6-oxo-piperidin-1-yl]-heptanoic acid methyl ester (10 mg, 0.026 mmol) was converted into 6.6 mg (68%) of the title compound.

EXAMPLE 19

7-[2-(3-Hydroxy-4-phenyl-butyl)-6-oxo-piperidin-1-yl]-heptanoic Acid Methyl Ester Palladium on carbon (10 wt. %, 5 mg) was added to a solution of 7-[2-((E)-3-hydroxy-4-phenyl-but-1-enyl)-6-oxo-piperidin-1-yl]-heptanoic acid methyl ester (20 mg, 0.052 mmol) in MeOH (2.0 mL). A hydrogen atmosphere was established by evacuating and refilling with hydrogen (3×) and the reaction mixture was stirred under a balloon of hydrogen for 22 h. The reaction mixture was filtered through celite, washing with MeOH, and the filtrate was concentrated in vacuo to afford 13 mg (65%) of the title compound.

EXAMPLE 20

7-[2-(3-Hydroxy-4-phenyl-butyl)-6-oxo-piperidin-1-yl]-heptanoic Acid

In accordance with the procedure of example 2, 7-[2-(3-hydroxy-4-phenyl-butyl)-6-oxo-piperidin-1-yl]-heptanoic acid methyl ester (11 mg, 0.029 mmol) was converted into 3.5 mg (32%) of the title compound.

EXAMPLE 21

7-[2-Oxo-6-(3-oxo-4-phenyl-butyl)-piperidin-1-yl]-heptanoic Acid Methyl Ester

In accordance with the procedure of example 19, 7-[2-oxo-6-((E)-3-oxo-4-phenyl-but-1-enyl)-piperidin-1-yl]-heptanoic acid methyl ester (20 mg, 0.052 mmol) was converted into 15 mg (75%) of the title compound.

EXAMPLE 22

7-[2-Oxo-6-(3-oxo-4-phenyl-butyl)-piperidin-1-yl]-heptanoic Acid

In accordance with the procedure of example 2, 7-[2-oxo-6-(3-oxo-4-phenyl-butyl)-piperidin-1-yl]-heptanoic acid methyl ester (12 mg, 0.031 mmol) was converted into 2.8 mg (24%) of the title compound.

EXAMPLE 23

7-[2-Oxo-6-((E)-3-oxo-4-phenyl-but-1-enyl)-piperidin-1-yl]-hept-5-ynoic Acid Methyl Ester Sodium hydride (60% dispersion in oil, 23 mg, 0.58 mmol) was added to a solution of dimethyl 2-oxo-3-phenylpropylphosphonate (171 mg, 0.64 mmol) in THF (2.0 mL) at 0° C. After 10 min at 0° C., the solution was allowed to warm to rt. After 50 min at rt, the solution was recooled to 0° C. and 7-(2-formyl-6-oxo-piperidin-1-yl)-hept-5-ynoic acid methyl ester (crude, prepared in accordance with example 1, step 4, ~0.64 mmol) in THF (2.0 mL) was added via cannula. The reaction was allowed to warm to rt. After 18 h at rt, the reaction was quenched with acetic acid (50% aqueous, 20 mL) and extracted with EtOAc (3×20 mL). The combined organic phase was washed with saturated aqueous NaHCO$_3$ (30 mL) and brine (30 mL), dried (Na$_2$SO$_4$), filtered and concentrated in vacuo. Purification of the residue by flash column chromatography on silica gel twice (1$^{st}$ CH$_2$Cl$_2$→2% MeOH/CH$_2$Cl$_2$, gradient and 2$^{nd}$ CH$_2$Cl$_2$→30% EtOAc/CH$_2$Cl$_2$, gradient) afforded 51 mg (21%) of the title compound.

EXAMPLE 24

7-[2-Oxo-6-((E)-3-oxo-4-phenyl-but-1-enyl)-piperidin-1-yl]-hept-5-ynoic Acid

In accordance with the procedure of example 2, 7-[2-Oxo-6-((E)-3-oxo-4-phenyl-but-1-enyl)-piperidin-1-yl]-hept-5-ynoic acid methyl ester (9 mg, 0.024 mmol) was converted into 1.4 mg (16%) of the title compound.

EXAMPLE 25

(Z)-7-[2-Oxo-6-((E)-3-oxo-4-phenyl-but-1-enyl)-piperidin-1-yl]-hept-5-enoic Acid Methyl Ester A round bottom flask was charged with nickel (II) chloride (68 mg, 0.52 mmol) and sodium borohydride (9.9 mg, 0.26 mmol), then 95% ethanol (1.0 mL) was added. The mixture immediately turned black. After 15 min at rt, ethylene diamine (56 □L, 0.84 mmol) was added. After another 15 min at rt, 7-[2-oxo-6-((E)-3-oxo-4-phenyl-but-1-enyl)-piperidin-1-yl]-hept-5-ynoic acid methyl ester (40 mg, 0.10 mmol) in 95% ethanol (1.0 mL) was added via cannula. A hydrogen atmosphere was established by evacuating and refilling with hydrogen (3×) and the reaction mixture was stirred under a balloon of hydrogen for 18 h. The reaction mixture was filtered through celite, washing with ethanol, and the filtrate was concentrated in vacuo. Purification of the resulting residue by flash column chromatography (CH$_2$Cl$_2$→30% EtOAc/CH$_2$Cl$_2$, gradient) afforded 28 mg (70%) of the title compound.

EXAMPLE 26

(Z)-7-[2-Oxo-6-((E)-3-oxo-4-phenyl-but-1-enyl)-piperidin-1-yl]-hept-5-enoic Acid In accordance with the procedure of example 2, (Z)-7-[2-oxo-6-((E)-3-oxo-4-phenyl-but-1-enyl)-piperidin-1-yl]-hept-5-enoic acid methyl ester (9.2 mg, 0.024 mmol) was converted into 8 mg (90%) of the title compound.

EXAMPLE 27

(Z)-7-[2-((E)-3-Hydroxy-4-phenyl-but-1-enyl)-6-oxo-piperidin-1-yl]-hept-5-enoic Acid Methyl Ester Sodium borohydride (16 mg, 0.42 mmol), followed by MeOH (0.25 mL), was added to a solution of (Z)-7-[2-oxo-6-((E)-3-oxo-4-phenyl-but-1-enyl)-piperidin-1-yl]-hept-5- enoic acid methyl ester (16 mg, 0.042 mmol) in $CH_2Cl_2$ (0.75 mL) at 0° C. The mixture was allowed to warm to rt. After 2.5 h at rt, the reaction was quenched with aqueous HCl (1.0 M) and extracted with EtOAc (3×15 mL). The combined organic phase was washed with saturated aqueous $NaHCO_3$ (15 mL) and brine (15 mL) then dried ($Na_2SO_4$), filtered and concentrated in vacuo. Purification of the residue by flash column chromatography on silica gel ($CH_2Cl_2 \rightarrow 50\%$ EtOAc/$CH_2Cl_2$, gradient) afforded 10 mg (62%) of the title compound.

EXAMPLE 28

(Z)-7-[2-((E)-3-Hydroxy-4-phenyl-but-1-enyl)-6-oxo-piperidin-1-yl]-hept-5-enoic Acid In accordance with the procedure of example 2, (Z)-7-[2-((E)-3-hydroxy-4-phenyl-but-1-enyl)-6-oxo-piperidin-1-yl]-hept-5-enoic acid methyl ester (8.5 mg, 0.022 mmol) was converted into 2.4 mg (29%) of the title compound.

EXAMPLE 29

7-[(R)-2-((E)-3-Hydroxy-4-phenyl-but-1-enyl)-6-oxo-piperidin-1-yl]-heptanoic Acid Methyl Ester Step 1. (R)-6-(tert-Butyldimethylsilanyloxymethyl)-piperidin-2-one Imidazole (773 mg, 11.4 mmol) and tert-butyldimethylsilyl chloride (787 mg, 5.22 mmol) were added sequentially to a solution of (R)-6-hydroxymethyl-piperidin-2-one (prepared from D-α-aminoadipic acid according to Huang, et al., *Synth. Commun.* 1989, 19, 3485–3496, 613 mg, 4.75 mmol) in DMF (8 mL) at 0° C. The reaction mixture was allowed to warm to rt and was stirred at rt for 20 h. Benzene and EtOAc (3:7, 200 mL) was added and the solution was washed with brine (3×50 mL). The organic phase was dried ($Na_2SO_4$), filtered and concentrated in vacuo. Purification of the residue by flash column chromatography on silica gel ($CH_2Cl_2 \rightarrow 3\%$ MeOH/$CH_2Cl_2$, gradient) afforded 1.13 g (98%) of (R)-6-(tert-butyldimethylsilanyloxymethyl)-piperidin-2-one as a white solid.

Step 2. 7-[(R)-2-tert-Butyldimethylsilanyloxymethyl)-6-oxo-piperidin-1-yl]-hept-5-ynoic Acid Methyl Ester Sodium hydride (60% dispersion in oil, 195 mg, 4.87 mmol) was added to a solution of (R)-6-(tert-butyldimethylsilanyloxymethyl)-piperidin-2-one (1.13 g, 4.64 mmol) in DMF (8 mL) at rt. After 1 h, methyl 7-iodohept-5-ynoate (1.35 g, 5.07 mmol) in DMF (2 mL) was added via cannula. After 18 h at rt, the reaction was quenched by the addition of aqueous HCl (0.5 M, 25 mL) and the mixture was extracted with EtOAc (3×50 mL). The combined organic phase was washed with saturated aqueous $NaHCO_3$ (50 mL) and brine (3×50 mL), dried ($Na_2SO_4$), filtered and concentrated in vacuo. Purification of the residue by flash column chromatography on silica gel ($CH_2Cl_2 \rightarrow 50\%$ EtOAc/$CH_2Cl_2$, gradient) afforded 713 mg (40%) of 7-[(R)-2-tert-butyldimethylsilanyloxymethyl)-6-oxo-piperidin-1-yl]-hept-5-ynoic acid methyl ester.

Step 3. 7-((R)-2-Hydroxymethyl-6-oxo-piperidin-1-yl)-hept-5-ynoic Acid Methyl Ester Hydrogen fluoride-pyridine (2 mL) was added to a solution of 7-[(R)-2-tert-butyldimethylsilanyloxymethyl)-6-oxo-piperidin-1-yl]-hept-5-ynoic acid methyl ester (705 g, 1.85 mmol) in acetonitrile (4.0 mL) in a plastic scintillation vial. After 3.5 h at rt, the reaction was quenched with saturated aqueous $NaHCO_3$ (50 mL) and the mixture was extracted with EtOAc (3×30 mL). The combined organic phase was washed with brine (50 mL), dried ($MgSO_4$), filtered and concentrated in vacuo. Purification of the residue by flash column chromatography on silica gel ($CH_2Cl_2 \rightarrow 3\%$ MeOH/$CH_2Cl_2$, gradient) afforded 347 mg (70%) of 7-((R)-2-hydroxymethyl-6-oxo-piperidin-1-yl)-hept-5-ynoic acid methyl ester.

Step 4. 7-((R)-2-Hydroxymethyl-6-oxo-piperidin-1-yl)-heptanoic Acid Methyl Ester Palladium on carbon (10 wt. %, 10 mg) was added to a solution of 7-((R)-2-hydroxymethyl-6-oxo-piperidin-1-yl)-hept-5-ynoic acid methyl ester (110 mg, 0.41 mmol) in MeOH (3.0 mL). A hydrogen atmosphere was established by evacuating and refilling with hydrogen (3×) and the reaction mixture was stirred under a balloon of hydrogen for 22 h. The reaction mixture was filtered through celite, washing with MeOH, and the filtrate was concentrated in vacuo to afford 110 mg (99%) of 7-((R)-2-hydroxymethyl-6-oxo-piperidin-1-yl)-heptanoic acid methyl ester.

Step 5. 7-((R)-2-Formyl-6-oxo-piperidin-1-yl)-heptanoic Acid Methyl Ester

EDCI (119 mg, 0.62 mmol) and DMSO (59 μL, 0.83 mmol) were added sequentially to a solution of 7-((R)-2-hydroxymethyl-6-oxo-piperidin-1-yl)-heptanoic acid methyl ester (56 mg, 0.21 mmol) in benzene (2.0 mL) at rt. The mixture was cooled to 0° C. and pyridinium trifluoroacetate (44 mg, 0.23 mmol) was added. The reaction was allowed to warm to rt and then was stirred at rt for 3 h. The solution was decanted from the oily residue and the residue was washed with benzene (3×2 mL). The combined benzene phases were concentrated in vacuo to afford crude 7-((R)-2-formyl-6-oxo-piperidin-1-yl)-heptanoic acid methyl ester that was used without further purification.

Step 6. 7-[(R)-2-Oxo-6-((E)-3-oxo-4-phenyl-but-1-enyl)-piperidin-1-yl]-heptanoic Acid Methyl Ester Sodium hydride (60% dispersion in oil, 8.2 mg, 0.21 mmol) was added to a solution of dimethyl 2-oxo-3-phenylpropylphosphonate (45 mg, 0.19 mmol) in THF (1.0 mL) at 0° C. After 10 min at 0° C., the solution was allowed to warm to rt. After 1 h at rt, the solution was recooled to 0° C. and 7-((R)-2-formyl-6-oxo-piperidin-1-yl)-heptanoic acid methyl ester (crude from previous reaction, ~0.21 mmol) in THF (1.0 mL) was added via cannula. The reaction was allowed to warm to rt. After 18 h at rt, the reaction was quenched with acetic acid (50% aqueous, 10 mL) and extracted with EtOAc (3×15 mL). The combined organic phase was washed with saturated aqueous $NaHCO_3$ (20 mL) and brine (20 mL), dried ($Na_2SO_4$), filtered and concentrated in vacuo. Purification of the residue by flash column chromatography on silica gel ($CH_2Cl_2 \rightarrow 2\%$ MeOH/$CH_2Cl_2$, gradient) afforded 36.5 mg (51%) of 7-[(R)-2-oxo-6-((E)-3-oxo-4-phenyl-but-1-enyl)-piperidin-1-yl]-heptanoic acid methyl ester.

Step 7. 7-[(R)-2-((E)-3-Hydroxy-4-phenyl-but-1-enyl)-6-oxo-piperidin-1-yl]-heptanoic Acid Methyl Ester Sodium borohydride (35 mg, 0.93 mmol), followed by MeOH (0.25 mL), was added to a solution of 7-[(R)-2-oxo-6-((E)-3-oxo-4-phenyl-but-1-enyl)-piperidin-1-yl]-heptanoic acid methyl ester (36 mg, 0.093 mmol) in $CH_2Cl_2$ (0.75 mL) at 0° C. The mixture was allowed to warm to rt. After 3 h at rt, the reaction was quenched with aqueous HCl (0.5 M, 5 mL) and extracted with EtOAc (3×10 mL). The combined organic phase was washed with saturated aqueous $NaHCO_3$ (10 mL) and brine (10 mL) then dried ($Na_2SO_4$), filtered and concentrated in vacuo. Purification of the residue by preparative thin layer chromatography (silica, 5% MeOH/$CH_2Cl_2$) afforded 20 mg (55%) of the title compound.

EXAMPLE 30

7-[(R)-2-((E)-3-Hydroxy-4-phenyl-but-1-enyl)-6-oxo-piperidin-1-yl]-heptanoic Acid Rabbit liver esterase (134 units/mg, 1 mg) was added to a solution of 7-[(R)-2-((E)-3-hydroxy-4-phenyl-but-1-enyl)-6-oxo-piperidin-1-yl]-heptanoic acid methyl ester (15 mg, 0.39 mmol) in acetonitrile (0.2 mL) and pH 7.2 phosphate buffer (3.0 mL). After 16.5 h, acetonitrile (5 mL) was added and the reaction mixture was concentrated to dryness in vacuo. Purification of the residue by flash column chromatography on silica gel ($CH_2Cl_2 \rightarrow 2\%$ MeOH/$CH_2Cl_2$, gradient) afforded 8.7 mg (60%) of the title compound.

EXAMPLE 31

7-[(R)-2-((E)-3-Hydroxy-oct-1-enyl)-6-oxo-piperidin-1-yl]-heptanoic Acid Methyl Ester Step 1. 7-[(R)-2-Oxo-6-((E)-3-oxo-oct-1-enyl)-piperidin-1-yl]-heptanoic Acid Sodium hydride (60% dispersion in oil, 7.2 mg, 0.18 mmol) was added to a solution of dimethyl 2-oxoheptylphosphonate (47 mg, 0.19 mmol) in THF (1 mL) at 0° C. After 10 min at 0° C., the solution was allowed to warm to rt. After 1 h at rt, the solution was recooled to 0° C. and 7-((R)-2-formyl-6-oxo-piperidin-1-yl)-heptanoic acid methyl ester (crude, prepared in accordance with Example 29, step 5, ~0.20 mmol) in THF (1 mL) was added via cannula. The reaction was allowed to warm to rt. After 17 h at rt, the reaction was quenched with aqueous acetic acid (50%, 5 mL) and extracted with EtOAc (3×10 mL). The combined organic phase was washed with saturated aqueous $NaHCO_3$ (10 mL) and brine (10 mL) then dried ($Na_2SO_4$), filtered and concentrated in vacuo. Purification of the residue by flash column chromatography on silica gel ($CH_2Cl_2 \rightarrow 2\%$ MeOH/$CH_2Cl_2$, gradient) afforded 59 mg (90%) of 7-[(R)-2-oxo-6-((E)-3-oxo-oct-1-enyl)-piperidin-1-yl]-heptanoic acid methyl ester.

Step 2. 7-[(R)-2-((E)-3-Hydroxy-oct-1-enyl)-6-oxo-piperidin-1-yl]-heptanoic Acid Methyl Ester Sodium borohydride (28 mg, 0.74 mmol), followed by MeOH (0.25 mL), was added to a solution of 7-[(R)-2-oxo-6-((E)-3-oxo-oct-1-enyl)-piperidin-1-yl]-heptanoic acid methyl ester (55 mg, 0.15 mmol) in $CH_2Cl_2$ (0.75 mL) at 0° C. The mixture was allowed to warm to rt. After 1 h at rt, the reaction was quenched with aqueous HCl (1.0 M, 2 mL) and extracted with EtOAc (3×10 mL). The combined organic phase was washed with brine (10 mL) then dried ($Na_2SO_4$), filtered and concentrated in vacuo to afford 55 mg (99%) of the title compound.

EXAMPLE 32

7-[(R)-2-((E)-3-Hydroxy-oct-1-enyl)-6-oxo-piperidin-1-yl]-heptanoic Acid

In accordance with the procedure of example 2, 7-[(R)-2-((E)-3-hydroxy-oct-1-enyl)-6-oxo-piperidin-1-yl]-heptanoic acid methyl ester (23 mg, 0.063 mmol) was converted into 10 mg (45%) of the title compound.

EXAMPLE 33

7-[(R)-2-(3-Hydroxy-octyl)-6-oxo-piperidin-1-yl]-heptanoic Acid Methyl Ester Palladium on carbon (10 wt. %, 7 mg) was added to a solution of 7-[(R)-2-((E)-3-hydroxy-oct-1-enyl)-6-oxo-piperidin-1-yl]-heptanoic acid methyl ester (33 mg, 0.90 mmol) in MeOH (3.0 mL). A hydrogen atmosphere was established by evacuating and refilling with hydrogen (3×) and the reaction mixture was stirred under a balloon of hydrogen for 18.5 h. The reaction mixture was filtered through celite, washing with MeOH, and the filtrate was concentrated in vacuo to afford 28 mg (84%) of the title compound.

EXAMPLE 34

7-[(R)-2-(3-Hydroxy-octyl)-6-oxo-piperidin-1-yl]-heptanoic Acid

In accordance with the procedure of example 2, 7-[(R)-2-(3-hydroxy-octyl)-6-oxo-piperidin-1-yl]-heptanoic acid methyl ester (24 mg, 0.065 mmol) was converted into 22 mg. (95%) of the title compound.

EXAMPLE 35 AND EXAMPLE 36

7-[(R)-2-((E)-3-Hydroxy-oct-1-enyl)-6-oxo-piperidin-1-yl]-hept-5-ynoic Acid Methyl Ester and (R)-1-(7-Hydroxy-hept-2-ynyl)-6-((E)-3-hydroxy-oct-1-enyl)-piperidin-2-one

Step 1. 7-((R)-2-Formyl-6-oxo-piperidin-1-yl)-hept-5-ynoic Acid Methyl Ester EDCI (127 mg, 0.66 mmol) and DMSO (62 µL, 0.87 mmol) were added sequentially to a solution of 7-((R)-2-hydroxymethyl-6-oxo-piperidin-1-yl)-hept-5-ynoic acid methyl ester (prepared in accordance with Example 29, step 3, 59 mg, 0.22 mmol) in benzene (2.0 mL) at rt. The mixture was cooled to 0° C. and pyridinium trifluoroacetate (47 mg, 0.24 mmol) was added. The reaction was allowed to warm to rt and then was stirred at rt for 2 h. The solution was decanted from the oily residue and the residue was washed with benzene (3×2 mL). The combined benzene phases were concentrated in vacuo to afford crude 7-((R)-2-formyl-6-oxo-piperidin-1-yl)-hept-5-ynoic acid methyl ester that was used without further purification.

Step 2. 7-[(R)-2-Oxo-6-((E)-3-oxo-oct-1-enyl)-piperidin-1-yl]-hept-5-ynoic Acid Methyl Ester Sodium hydride (60% dispersion in oil, 8.8 mg, 0.22 mmol) was added to a solution of dimethyl 2-oxoheptylphosphonate (52 mg, 0.23 mmol) in THF (1 mL) at 0° C. After 10 min at 0° C., the solution was allowed to warm to rt. After 1 h at rt, the solution was recooled to 0° C. and 7-((R)-2-formyl-6-oxo-piperidin-1-yl)-hept-5-ynoic acid methyl ester (crude from previous reaction, ~0.22 mmol) in THF (1 mL) was added via cannula. The reaction was allowed to warm to rt. After 18.5 h at rt, the reaction was quenched with aqueous acetic acid (50%, 5 mL) and extracted with EtOAc (3×10 mL). The combined organic phase was washed with saturated aqueous $NaHCO_3$ (10 mL) and brine (10 mL) then dried ($Na_2SO_4$), filtered and concentrated in vacuo. Purification of the residue by flash column chromatography on silica gel ($CH_2Cl_2 \rightarrow 2\%$ $MeOH/CH_2Cl_2$, gradient) afforded 68 mg (85%) of 7-[(R)-2-oxo-6-((E)-3-oxo-oct-1-enyl)-piperidin-1-yl]-hept-5-ynoic acid methyl ester.

Step 3. 7-[(R)-2-((E)-3-Hydroxy-oct-1-enyl)-6-oxo-piperidin-1-yl]-hept-5-ynoic Acid Methyl Ester and (R)-1-(7-Hydroxy-hept-2-ynyl)-6-((E)-3-hydroxy-oct-1-enyl)-piperidin-2-one Sodium borohydride (35 mg, 0.93 mmol), followed by MeOH (0.25 mL), was added to a solution of 7-[(R)-2-oxo-6-((E)-3-oxo-oct-1-enyl)-piperidin-1-yl]-hept-5-ynoic acid methyl ester (68 mg, 0.19 mmol) in $CH_2Cl_2$ (1.0 mL) at 0° C. The mixture was allowed to warm to rt. After 1 h at rt, the reaction was quenched with aqueous HCl (1.0 M, 3 mL) and extracted with EtOAc (3×10 mL). The combined organic phase was washed with brine (20 mL) then dried ($Na_2SO_4$), filtered and concentrated in vacuo. Purification of the residue by flash column chromatography on silica gel ($CH_2Cl_2 \rightarrow 3\%$ $MeOH/CH_2Cl_2$, gradient) afforded 26 mg (38%) of 7-[(R)-2-((E)-3-hydroxy-oct-1-enyl)-6-oxo-piperidin-1-yl]-hept-5-ynoic acid methyl ester and 5.3 mg (8%) of (R)-1-(7-hydroxy-hept-2-ynyl)-6-((E)-3-hydroxy-oct-1-enyl)-piperidin-2-one.

EXAMPLE 37

(Z)-7-[(R)-2-((E)-3-Hydroxy-oct-1-enyl)-6-oxo-piperidin-1-yl]-hept-5-enoic Acid Methyl Ester Palladium on carbon (10 wt. %, 3 mg) was added to a solution of solution of 7-[(R)-2-((E)-3-hydroxy-oct-1-enyl)-6-oxo-piperidin-1-yl]-hept-5-ynoic acid methyl ester (13.5 mg, 0.037 mmol) in MeOH (2.0 mL). A hydrogen atmosphere was established by evacuating and refilling with hydrogen (3×) and the reaction mixture was stirred under a balloon of hydrogen for 23 h. The reaction mixture was filtered through celite, washing with ethanol, and the filtrate was concentrated in vacuo to afford 13.2 mg (97%) of the title compound.

EXAMPLE 38

(Z)-7-[(R)-2-((E)-3-Hydroxy-oct-1-enyl)-6-oxo-piperidin-1-yl]-hept-5-enoic Acid

In accordance with the procedure of example 2, (Z)-7-[(R)-2-((E)-3-hydroxy-oct-1-enyl)-6-oxo-piperidin-1-yl]-hept-5-enoic acid methyl ester (10.5 mg, 0.029 mmol) was converted into 1.3 mg (13%) of the title compound.

EXAMPLE 39

(Z)-7-[(R)-2-((E)-3-Hydroxy-4-phenyl-but-1-enyl)-6-oxo-piperidin-1-yl]-hept-5-enoic Acid Methyl Ester Step 1. 7-((R)-2-Hydroxymethyl-6-oxo-piperidin-1-yl)-hept-5-enoic Acid Methyl ester 95% Ethanol (0.5 mL) was added to a mixture of nickel (II) chloride (105 mg, 0.81 mmol) and sodium borohydride (15 mg, 0.40 mmol). The mixture immediately turned black. After 15 min at rt, ethylene diamine (86 μL, 1.29 mmol) was added. After 15 min at rt, a solution of 7-((R)-2-hydroxymethyl-6-oxo-piperidin-1-yl)-hept-5-ynoic acid methyl ester (from Example 1, step 3, 43.3 mg, 0.16 mmol) in 95% ethanol (1.0 mL) was added via cannula. A hydrogen atmosphere was established by evacuating and refilling with hydrogen (3×) and the reaction mixture was stirred under a balloon of hydrogen for 19 h. The reaction mixture was filtered through celite, washing with ethanol, and the filtrate was concentrated in vacuo. Purification of the residue by flash column chromatography on silica gel ($CH_2Cl_2 \rightarrow 3\%$ $MeOH/CH_2Cl_2$, gradient) afforded 16.7 mg (38%) of 7-((R)-2-hydroxymethyl-6-oxo-piperidin-1-yl)-hept-5-enoic acid methyl ester.

Step 2. 7-((R)-2-Formyl-6-oxo-piperidin-1-yl)-hept-5-enoic acid methyl ester EDCI (36 mg, 0.19 mmol) and DMSO (18 μL, 0.25 mmol) were added sequentially to a solution of 7-((R)-2-hydroxymethyl-6-oxo-piperidin-1-yl)-hept-5-enoic acid methyl ester (16.7 mg, 0.062 mmol) in benzene (1.0 mL) at rt. The mixture was cooled to 0° C. and pyridinium trifluoroacetate (13.2 mg, 0.068 mmol) was added. The reaction was allowed to warm to rt and then was stirred at rt for 2.5 h. The solution was decanted from the oily residue and the residue was washed with benzene (3×1 mL). The combined benzene phases were concentrated in vacuo to afford crude 7-((R)-2-formyl-6-oxo-piperidin-1-yl)-hept-5-enoic acid methyl ester that was used without further purification.

Step 3. 7-[(R)-2-Oxo-6-((E)-3-oxo-4-phenyl-but-1-enyl)-piperidin-1-yl]-hept-5-enoic Acid Methyl Ester Sodium hydride (60% dispersion in oil, 2.5 mg, 0.063 mmol) was added to a solution of dimethyl 2-oxo-3-phenylpropylphosphonate (14 mg, 0.058 mmol) in THF (0.3 mL) at 0° C. After 1 h at 0° C. rt, 7-((R)-2-formyl-6-oxo-piperidin-1-yl)-hept-5-enoic acid methyl ester (crude from previous reaction, ~0.062 mmol) in THF (0.7 mL) was added via cannula. The reaction was allowed to warm to rt.

After 18 h at rt, the reaction was quenched with acetic acid (50% aqueous, 5 mL) and extracted with EtOAc (3×5 mL). The combined organic phase was washed brine (10 mL), dried ($Na_2SO_4$), filtered and concentrated in vacuo. Purification of the residue by flash column chromatography on silica gel ($CH_2Cl_2 \rightarrow 25\%$ EtOAc/$CH_2Cl_2$, gradient) afforded 10 mg (42%) of 7-[(R)-2-oxo-6-((E)-3-oxo-4-phenyl-but-1-enyl)-piperidin-1-yl]-hept-5-enoic acid methyl ester.

Step 4. 7-[(R)-2-((E)-3-Hydroxy-4-phenyl-but-1-enyl)-6-oxo-piperidin-1-yl]-hept-5-enoic Acid Methyl Ester Sodium borohydride (2.0 mg, 0.053 mmol), followed by MeOH (0.1 mL), was added to a solution of 7-[(R)-2-oxo-6-((E)-3-oxo-4-phenyl-but-1-enyl)-piperidin-1-yl]-hept-5-enoic acid methyl ester (10 mg, 0.026 mmol) in $CH_2Cl_2$ (0.5 mL) at 0° C. The mixture was allowed to warm to rt. After 10 min at rt, the reaction was quenched with aqueous HCl (1.0 M, 1 mL) and extracted with EtOAc (3×5 mL). The combined organic phase was washed with brine (10 mL) then dried ($Na_2SO_4$), filtered and concentrated in vacuo. Purification of the residue by flash column chromatography on silica gel ($CH_2Cl_2 \rightarrow 2\%$ MeOH/$CH_2Cl_2$, gradient) afforded 9.9 mg (98%) of the title compound.

EXAMPLE 40

(Z)-7-[(R)-2-((E)-3-Hydroxy-4-phenyl-but-1-enyl)-6-oxo-piperidin-1-yl]-hept-5-enoic Acid In accordance with the procedure of example 2, (Z)-7-[(R)-2-((E)-3-hydroxy-4-phenyl-but-1-enyl)-6-oxo-piperidin-1-yl]-hept-5-enoic acid methyl ester (6.9 mg, 0.018 mmol) was converted into 2.0 mg (30%) of the title compound.

EXAMPLE 41

7-[(R)-2-((E)-3-Hydroxy-4-phenyl-but-1-enyl)-6-oxo-piperidin-1-yl]-hept-5-ynoic Acid Methyl Ester Step 1. 7-[(R)-2-Oxo-6-((E)-3-oxo-4-phenyl-but-1-enyl)-piperidin-1-yl]-hept-5-ynoic Acid Methyl Ester Sodium hydride (60% dispersion in oil, 3.8 mg, 0.095 mmol) was added to a solution of dimethyl 2-oxo-3-phenylpropylphosphonate (21 mg, 0.087 mmol) in THF (0.5 mL) at 0° C. After 1 h at 0° C. rt, 7-((R)-2-formyl-6-oxo-piperidin-1-yl)-hept-5-ynoic acid methyl ester (prepared in accordance with example 7, step 1, crude, ~0.095 mmol) in THF (0.5 mL) was added via cannula. The reaction was allowed to warm to rt. After 17.5 h at rt, the reaction was quenched with acetic acid (50% aqueous, 5 mL) and extracted with EtOAc (3×5 mL). The combined organic phase was washed brine (10 mL), dried ($Na_2SO_4$), filtered and concentrated in vacuo. Purification of the residue by flash column chromatography on silica gel ($CH_2Cl_2 \rightarrow 30\%$ EtOAc/$CH_2Cl_2$, gradient) afforded 14 mg (42%) of 7-[(R)-2-oxo-6-((E)-3-oxo-4-phenyl-but-1-enyl)-piperidin-1-yl]-hept-5-ynoic acid methyl ester.

Step 2. 7-[(R)-2-((E)-3-Hydroxy-4-phenyl-but-1-enyl)-6-oxo-piperidin-1-yl]-hept-5-ynoic Acid Methyl Ester Sodium borohydride (2 mg, 0.053 mmol), followed by MeOH (0.1 mL), was added to a solution of 7-[(R)-2-oxo-6-((E)-3-oxo-4-phenyl-but-1-enyl)-piperidin-1-yl]-hept-5-ynoic acid methyl ester (14 mg, 0.037 mmol) in $CH_2Cl_2$ (0.5 mL) at 0° C. The mixture was allowed to warm to rt. After 30 min at rt, the reaction was quenched with aqueous HCl (1.0 M, 1 mL) and extracted with EtOAc (3×5 mL). The combined organic phase was washed with brine (10 mL) then dried ($Na_2SO_4$), filtered and concentrated in vacuo. Purification of the residue by flash column chromatography on silica gel ($CH_2Cl_2 \rightarrow 2\%$ MeOH/$CH_2Cl_2$, gradient) afforded 11 mg (78%) of the title compound.

EXAMPLE 42

7-[(R)-2-((E)-3-Hydroxy-4-phenyl-but-1-enyl)-6-oxo-piperidin-1-yl]-hept-5-ynoic Acid In accordance with the procedure of example 2, 7-[(R)-2-((E)-3-hydroxy-4-phenyl-but-1-enyl)-6-oxo-piperidin-1-yl]-hept-5-ynoic acid methyl ester (8.7 mg, 0.023 mmol) was converted into 4.1 mg (49%) of the title compound.

EXAMPLE 43

7-[(R)-2-((E)-3-Hydroxy-4-phenyl-but-1-enyl)-6-oxo-piperidin-1-yl]-heptanoic Acid Isopropyl Ester A mixture of 7-[(R)-2-((E)-3-hydroxy-4-phenyl-but-1-enyl)-6-oxo-piperidin-1-yl]-heptanoic acid (9.7 mg, 0.026 mmol), 1-isopropyl-3-p-tolyltriazene (5 mg, 0.028 mmol) and acetone (0.5 mL) was stirred at rt for 18 h. The reaction was quenched with saturated aqueous $NH_4Cl$ (2 mL) and extracted with $CH_2Cl_2$ (3×3 mL). The combined organic phase was dried ($Na_2SO_4$), filtered and concentrated in vacuo. Purification of the residue by flash column chromatography on silica gel (50% $CH_2Cl_2$/Hexane$\rightarrow CH_2Cl_2 \rightarrow 2\%$ MeOH/$CH_2Cl_2$, gradient) afforded 5.1 mg (47%) of the title compound.

EXAMPLE 44

7-[(R)-2-((E)-3-Hydroxy-4-phenyl-but-1-enyl)-6-oxo-piperidin-1-yl]-heptanoic Acid Amide Triethylamine (9 μL, 0.065 mmol) was added to a solution of 7-[(R)-2-((E)-3-hydroxy-4-phenyl-but-1-enyl)-6-oxo-piperidin-1-yl]-heptanoic acid (11.3 mg, 0.030 mmol) in $CH_2Cl_2$ (0.3 mL) at rt. After cooling to 0° C., ethyl chloroformate (3.2 μL, 0.033 mmol) was added. After 1 h at 0° C., a solution of ammonia (0.5 M in 1,4-dioxane, 0.3 mL, 0.15 mmol) was added and the reaction mixture was allowed to warm to rt. After 18 h at rt, the reaction mixture was diluted with EtOAc (10 mL) and washed with aqueous HCl (0.5 M, 3 mL), saturated aqueous $NaHCO_3$ (5 mL) and brine (5 mL) then dried ($Na_2SO_4$), filtered and concentrated in vacuo. Purification of the residue by flash column chromatography on silica gel ($CH_2Cl_2 \rightarrow 3\%$ MeOH/$CH_2Cl_2$, gradient) afforded 3.5 mg (31%) of the title compound.

EXAMPLE 45 AND EXAMPLE 46

7-[(R)-2-((E)-3-Hydroxy-4-phenyl-but-1-enyl)-6-oxo-piperidin-1-yl]-heptanoic Acid Isopropyl Ester (Faster Eluting Diastereomer by HPLC) and 7-[(R)-2-((E)-3-Hydroxy-4-phenyl-but-1-enyl)-6-oxo-piperidin-1-yl]-heptanoic Acid Isopropyl Ester (Slower Eluting Diastereomer by HPLC)

The two diastereomers of example 15 (47 mg, 0.11 mmol) dissolved in 20% EtOAc/Hexane (1.75 mL) were separated in three batches (0.5 mL, 0.5 mL and 0.75 mL) on a Waters 600 HPLC instrument employing a Waters 2996 PDA detector and a Whatman Partisil® 10 column having dimensions of 9.4×500 mm. Using EtOAc as the eluent and a flow rate of 8 mL/min, the first diastereomer (7.8 mg total isolated) eluted at 18 min, and the second diastereomer (9 mg total isolated) eluted at 22 min.

EXAMPLE 47

7-[(R)-2-((E)-3-Hydroxy-4-phenyl-but-1-enyl)-6-oxo-piperidin-1-yl]-hept-5-ynoic Acid Isopropyl Ester 1,8-Diazabicyclo[5.4.0]undec-7-ene (15 µL, 0.10 mmol) was added to a solution of 7-[(R)-2-((E)-3-hydroxy-4-phenyl-but-1-enyl)-6-oxo-piperidin-1-yl]-hept-5-ynoic acid (25 mg, 0.068 mmol) in acetone (0.68 mL) at rt. After 5 min, 2-iodopropane (34 µL, 0.34 mmol) was added. After 18 h at rt, the reaction mixture was diluted with EtOAc (25 mL) and washed with aqueous HCl (0.5 M, 10 mL), saturated aqueous NaHCO$_3$ (10 mL) and brine (10 mL) then dried (Na$_2$SO$_4$), filtered and concentrated in vacuo. Purification of the residue by flash column chromatography on silica gel (CH$_2$Cl$_2$→5% MeOH/CH$_2$Cl$_2$, gradient) afforded 13 mg (47%) of the title compound.

EXAMPLE 48 AND EXAMPLE 49

7-[(R)-2-((E)-3-Hydroxy-4-phenyl-but-1-enyl)-6-oxo-piperidin-1-yl]-hept-5-ynoic Acid Isopropyl Ester (Faster Eluting Diastereomer by HPLC) and 7-[(R)-2-((E)-3-Hydroxy-4-phenyl-but-1-enyl)-6-oxo-piperidin-1-yl]-hept-5-ynoic Acid Isopropyl Ester (slower eluting diastereomer by HPLC)

The two diastereomers of example 19 (11 mg, 0.027 mmol) dissolved in EtOAc (0.75 mL) were separated on a Waters 600 HPLC instrument employing a Waters 2996 PDA detector and a Whatman Partisil® 10 column having dimensions of 22×500 mm. Using EtOAc as the eluent and a flow rate of 10 mL/min, the first diastereomer (3 mg) eluted at 40 min, and the second diastereomer (3 mg) eluted at 44 min.

EXAMPLE 50

{4-[(R)-2-Oxo-6-((E)-3-oxo-4-phenyl-but-1-enyl)-piperidin-1-yl]-butoxy}-acetic Acid Methyl Ester (FIG. 1)

Step 1.
(R)-6-(1-Ethoxyethoxymethyl)-piperidin-2-one

Ethyl vinyl ether (1.68 mL, 17.5 mmol) and trifluoroacetic acid (0.1 mL) were added sequentially to a solution of (R)-6-hydroxymethylpiperidin-2-one (prepared from D-α-aminoadipic acid according to Huang, et al., *Synth. Commun.* 1989, 19, 3485–3496, 1.62 g, 12.5 mmol) in CHCl$_3$ (10 mL) at rt. The reaction mixture was stirred at rt for 18 h, then saturated aqueous NaHCO$_3$ (100 mL) was added and the mixture was extracted with CH$_2$Cl$_2$ (3×75 mL). The combined organic phase was dried (Na$_2$SO$_4$), filtered and concentrated in vacuo. Purification of the residue by flash column chromatography on silica gel (CH$_2$Cl$_2$→4% MeOH/CH$_2$Cl$_2$, gradient) afforded 2.03 g (80%) of (R)-6-(1-ethoxyethoxymethyl)-piperidin-2-one.

Step 2. {(Z)-4-[(R)-2-(1-Ethoxyethoxymethyl)-6-oxo-piperidin-1-yl]-but-2-enyloxy}-acetic Acid Ethyl Ester Sodium hydride (60% dispersion in oil, 402 mg, 10.0 mmol) was added to a solution of (R)-6-(1-ethoxyethoxymethyl)-piperidin-2-one (2.02 g, 10.0 mmol) in DMF (15 mL) at 0° C. After 1 h, a solution of potassium iodide (1.66 g, 10.0 mmol) and ((Z)-4-chloro-but-2-enyloxy)-acetic acid ethyl ester (prepared according to PCT 2003/007941, 3.09 g, 16.0 mmol) in DMF (10 mL) was added via cannula. The reaction was allowed to warm to rt. After 18 h at rt, the reaction was quenched by the addition of saturated aqueous NaHCO$_3$ (100 mL) and the mixture was extracted with EtOAc (3×100 mL). The combined organic phase was washed with brine (3×100 mL), dried (Na$_2$SO$_4$), filtered and concentrated in vacuo. Purification of the residue by flash column chromatography on silica gel (10% EtOAc/CH$_2$Cl$_2$→60% EtOAc/CH$_2$Cl$_2$, gradient) afforded 1.10 g (31%) of {(Z)-4-[(R)-2-(1-ethoxyethoxymethyl)-6-oxo-piperidin-1-yl]-but-2-enyloxy}-acetic acid ethyl ester.

Step 3. [(Z)-4-((R)-2-Hydroxymethyl-6-oxo-piperidin-1-yl)-but-2-enyloxy]-acetic Acid Methyl Ester p-Toluenesulfonic acid hydrate (620 mg, 3.26 mmol) was added to a solution of {(Z)-4-[(R)-2-(1-ethoxyethoxymethyl)-6-oxo-piperidin-1-yl]-but-2-enyloxy}-acetic acid ethyl ester (1.10 g, 3.08 mmol) in MeOH (10 mL). After 17 h at rt, the reaction was quenched with saturated aqueous NaHCO$_3$ (20 mL) and the mixture was extracted with CH$_2$Cl$_2$ (3×30 mL). The combined organic phase was dried (Na$_2$SO$_4$), filtered and concentrated in vacuo. Purification of the residue by flash column chromatography on silica gel (40% EtOAc/CH$_2$Cl$_2$→60% EtOAc/CH$_2$Cl$_2$, gradient, then 7% MeOH/CH$_2$Cl$_2$) afforded 538 mg (64%) of [(Z)-4-((R)-2-hydroxymethyl-6-oxo-piperidin-1-yl)-but-2-enyloxy]-acetic acid methyl ester.

Step 4. [4-((R)-2-Hydroxymethyl-6-oxo-piperidin-1-yl)-butoxy]-acetic Acid Methyl Ester Palladium on carbon (10 wt. %, 25 mg) was added to a solution of [(Z)-4-((R)-2-hydroxymethyl-6-oxo-piperidin-1-yl)-but-2-enyloxy]-acetic acid methyl ester (318 mg, 1.17 mmol) in MeOH (5.0 mL). A hydrogen atmosphere was established by evacuating and refilling with hydrogen (3×) and the reaction mixture was stirred under a balloon of hydrogen for 2.25 h. The reaction mixture was filtered through celite, washing with MeOH, and the filtrate was concentrated in vacuo. Purification of the residue by flash column chromatography on silica gel (30% EtOAc/CH$_2$Cl$_2$→50% EtOAc/CH$_2$Cl$_2$, gradient, then 2% MeOH/CH$_2$Cl$_2$→5% MeOH/CH$_2$Cl$_2$) afforded 285 mg (89%) of [4-((R)-2-hydroxymethyl-6-oxo-piperidin-1-yl)-butoxy]-acetic acid methyl ester.

Step 5. [4-((R)-2-Formyl-6-oxo-piperidin-1-yl)-butoxy]-acetic Acid Methyl Ester A solution of oxalyl chloride (0.15 mL, 1.76 mmol) in $CH_2Cl_2$ (1.0 mL) was added to a solution of DMSO (0.16 mL, 2.25 mmol) in $CH_2Cl_2$ (1.0 mL) at −78° C. After 15 min at −78° C., a solution of [4-((R)-2-hydroxymethyl-6-oxo-piperidin-1-yl)-butoxy]-acetic acid methyl ester (240 mg, 0.88 mmol) in $CH_2Cl_2$ (1.5 mL) was added via cannula. After 20 min at −78° C., triethylamine (0.37 mL, 2.65 mmol) was added. After 20 min at −78° C., the mixture was allowed to warm to 0° C. After 30 min at 0° C., the reaction was allowed to warm to rt. After 45 min at rt, saturated aqueous $NaHCO_3$ (15 mL) was added and the mixture was extracted with $CH_2Cl_2$ (3×15 mL). The combined organic phase was dried ($Na_2SO_4$), filtered and concentrated in vacuo. Purification of the residue by flash column chromatography on silica gel (40% →70% EtOAc/$CH_2Cl_2$, gradient) afforded 96 mg (40%) of [4-((R)-2-formyl-6-oxo-piperidin-1-yl)-butoxy]-acetic acid methyl ester.

Step 6. {4-[(R)-2-Oxo-6-((E)-3-oxo-4-phenyl-but-1-enyl)-piperidin-1-yl]-butoxy}-acetic Acid Methyl Ester Sodium hydride (60% dispersion in oil, 14 mg, 0.35 mmol) was added to a solution of dimethyl 2-oxo-3-phenylpropylphosphonate (83 mg, 0.34 mmol) in THF (1.0 mL) at 0° C. After 1 h at 0° C., [4-((R)-2-formyl-6-oxo-piperidin-1-yl)-butoxy]-acetic acid methyl ester (94 mg, 0.35 mmol) in THF (1 mL) was added via cannula. The reaction was allowed to warm to rt. After 22 h at rt, the reaction was quenched with saturated aqueous $NH_4Cl$ (10 mL) and extracted with EtOAc (3×15 mL). The combined organic phase was washed with brine (20 mL), dried ($Na_2SO_4$), filtered and concentrated in vacuo. Purification of the residue by flash column chromatography on silica gel (30% →50% EtOAc/$CH_2Cl_2$, gradient) afforded 42 mg (31%) of the title compound.

EXAMPLE 51

{4-[(R)-2-Oxo-6-((E)-3-oxo-4-phenyl-but-1-enyl)-piperidin-1-yl]-butoxy}-acetic Acid In accordance with the procedure of example 2, {4-[(R)-2-oxo-6-((E)-3-oxo-4-phenyl-but-1-enyl)-piperidin-1-yl]-butoxy}-acetic acid methyl ester (10 mg, 0.026 mmol) was converted into 7.7 mg (80%) of the title compound.

EXAMPLE 52

{4-[(R)-2-((E)-3-Hydroxy-4-phenyl-but-1-enyl)-6-oxo-piperidin-1-yl]-butoxy}-acetic Acid Methyl Ester Sodium borohydride (4 mg, 0.11 mmol), followed by MeOH (0.25 mL), was added to a solution of {4-[(R)-2-oxo-6-((E)-3-oxo-4-phenyl-but-1-enyl)-piperidin-1-yl]-butoxy}-acetic acid methyl ester (28 mg, 0.072 mmol) in $CH_2Cl_2$ (0.75 mL) at 0° C. The mixture was allowed to warm to rt. After 40 min at rt, the reaction was quenched with aqueous HCl (0.5 M) and extracted with EtOAc (3×7 mL). The combined organic phase was dried ($Na_2SO_4$), filtered and concentrated in vacuo to afford 22 mg (78%) of the title compound.

EXAMPLE 53

{4-[(R)-2-((E)-3-Hydroxy-4-phenyl-but-1-enyl)-6-oxo-piperidin-1-yl]-butoxy}-acetic Acid In accordance with the procedure of example 2, {4-[(R)-2-((E)-3-hydroxy-4-phenyl-but-1-enyl)-6-oxo-piperidin-1-yl]-butoxy}-acetic acid methyl ester (12.6 mg, 0.032 mmol) was converted into 10.5 mg (86%) of the title compound.

EXAMPLE 54

{4-[(R)-2-(3-Hydroxy-4-phenyl-butyl)-6-oxo-piperidin-1-yl]-butoxy}-acetic Acid Methyl Ester Palladium on carbon (10 wt. %, 3 mg) was added to a solution of {4-[(R)-2-((E)-3-hydroxy-4-phenyl-but-1-enyl)-6-oxo-piperidin-1-yl]-butoxy}-acetic acid methyl ester (9.5 mg, 0.024 mmol) in MeOH (2.0 mL). A hydrogen atmosphere was established by evacuating and refilling with hydrogen (3×) and the reaction mixture was stirred under a balloon of hydrogen for 4 h. The reaction mixture was filtered through celite, washing with MeOH, and the filtrate was concentrated in vacuo to afford 8.2 mg (86%) of the title compound.

EXAMPLE 55

{4-[(R)-2-(3-Hydroxy-4-phenyl-butyl)-6-oxo-piperidin-1-yl]-butoxy}-acetic Acid

In accordance with the procedure of example 2, {4-[(R)-2-(3-hydroxy-4-phenyl-butyl)-6-oxo-piperidin-1-yl]-butoxy}-acetic acid methyl ester (7.2 mg, 0.018 mmol) was converted into 6.9 mg (99%) of the title compound.

EXAMPLE 56

{(Z)-4-[(R)-2-Oxo-6-((E)-3-oxo-4-phenyl-but-1-enyl)-piperidin-1-yl]-but-2-enyloxy}-acetic Acid Methyl Ester (FIG. 2)

Step 1. [(Z)$_4$-((R)-2-Formyl-6-oxo-piperidin-1-yl)-but-2-enyloxy]-acetic Acid Methyl Ester Trifluoroacetic anhydride (0.24 mL, 1.70 mmol) was added to a solution of DMSO (0.14 mL, 1.97 mmol) in $CH_2Cl_2$ (2 mL) at −78° C. After 15 min at −78° C., a solution of [(Z)-4-((R)-2-hydroxymethyl-6-oxo-piperidin-1-yl)-but-2-enyloxy]acetic acid methyl ester (from example 1, step 3, 220 mg, 0.81 mmol) in $CH_2Cl_2$ (1.5 mL) was added via cannula. After 20 min at −78° C., triethylamine (0.33 mL, 2.37 mmol) was added and the reaction mixture was allowed to warm to rt. After 1 h at rt, the reaction was quenched with saturated aqueous $NH_4Cl$ (15 mL) and the mixture was extracted with $CH_2Cl_2$ (3×15 mL). The combined organic phase was dried ($Na_2SO_4$), filtered and concentrated in vacuo. Purification of the residue by flash column chromatography on silica gel (10% →50% EtOAc/$CH_2Cl_2$, gradient) afforded 150 mg (69%) of [(Z)-4-((R)-2-formyl-6-oxo-piperidin-1-yl)-but-2-enyloxy]-acetic acid methyl ester.

Step 2. {(Z)-4-[(R)-2-Oxo-6-((E)-3-oxo-4-phenyl-but-1-enyl)-piperidin-1-yl]-but-2-enyloxy}-acetic Acid Methyl Ester Sodium hydride (60% dispersion in oil, 22 mg, 0.55 mmol) was added to a solution of dimethyl 2-oxo-3-phenylpropylphosphonate (135 mg, 0.56 mmol) in THF (1.0 mL) at 0° C. After 1 h at 0° C., [(Z)-4-((R)-2-formyl-6-oxo-piperidin-1-yl)-but-2-enyloxy]-acetic acid methyl ester (150 mg, 0.56 mmol) in THF (1 mL) was added via cannula. The reaction was allowed to warm to rt. After 16.5 h at rt, the reaction was quenched with saturated aqueous NH$_4$Cl (15 mL) and extracted with EtOAc (3×15 mL). The combined organic phase was washed with brine (20 mL), dried (Na$_2$SO$_4$), filtered and concentrated in vacuo. Purification of the residue by flash column chromatography on silica gel (30% →60% EtOAc/CH$_2$Cl$_2$, gradient) afforded 91 mg (42%) of the title compound.

EXAMPLE 57

{(Z)-4-[(R)-2-Oxo-6-((E)-3-oxo-4-phenyl-but-1-enyl)-piperidin-1-yl]-but-2-enyloxy}-acetic Acid In accordance with the procedure of example 2, {(Z)-4-[(R)-2-oxo-6-((E)-3-oxo-4-phenyl-but-1-enyl)-piperidin-1-yl]-but-2-enyloxy}-acetic acid methyl ester (6.3 mg, 0.016 mmol) was converted into 1.9 mg (31%) of the title compound.

EXAMPLE 58

{4-[(R)-2-Oxo-6-(3-oxo-4-phenyl-butyl)-piperidin-1-yl]-butoxy}-acetic Acid Methyl Ester Palladium on carbon (10 wt. %, 2 mg) was added to a solution of {(Z)-4-[(R)-2-oxo-6-((E)-3-oxo-4-phenyl-but-1-enyl)-piperidin-1-yl]-but-2-enyloxy}-acetic acid methyl ester (9.7 mg, 0.025 mmol) in MeOH (1.5 mL). A hydrogen atmosphere was established by evacuating and refilling with hydrogen (3×) and the reaction mixture was stirred under a balloon of hydrogen for 19 h. The reaction mixture was filtered through celite, washing with MeOH, and the filtrate was concentrated in vacuo to afford 8.3 mg (85%) of the title compound.

EXAMPLE 59

{4-[(R)-2-Oxo-6-(3-oxo-4-phenyl-butyl)-piperidin-1-yl]-butoxy}-acetic Acid

In accordance with the procedure of example 2, 4-[(R)-2-oxo-6-(3-oxo-4-phenyl-butyl)-piperidin-1-yl]-butoxy}-acetic acid methyl ester (6.9 mg, 0.018 mmol) was converted into 6.2 mg (93%) of the title compound.

EXAMPLE 60

{(Z)-4-[(R)-2-((E)-3-Hydroxy-4-phenyl-but-1-enyl)-6-oxo-piperidin-1-yl]-but-2-enyloxy}-acetic Acid Methyl Ester Sodium borohydride (4 mg, 0.11 mmol), followed by MeOH (0.25 mL), was added to a solution of {(Z)-4-[(R)-2-oxo-6-((E)-3-oxo-4-phenyl-but-1-enyl)-piperidin-1-yl]-but-2-enyloxy}-acetic acid methyl ester (28 mg, 0.073 mmol) in CH$_2$Cl$_2$ (0.75 mL) at 0° C. The mixture was allowed to warm to rt. After 1 h at rt, the reaction was quenched with aqueous HCl (0.5 M) and extracted with EtOAc (3×10 mL). The combined organic phase was dried (Na$_2$SO$_4$), filtered and concentrated in vacuo to afford 22 mg (78%) of the title compound.

EXAMPLE 61

{(Z)-4-[(R)-2-((E)-3-Hydroxy-4-phenyl-but-1-enyl)-6-oxo-piperidin-1-yl]-but-2-enyloxy}-acetic Acid In accordance with the procedure of example 2, {(Z)-4-[(R)-2-((E)-3-hydroxy-4-phenyl-but-1-enyl)-6-oxo-piperidin-1-yl]-but-2-enyloxy}-acetic acid methyl ester (17.7 mg, 0.046 mmol) was converted into 17 mg (99%) of the title compound.

EXAMPLE 62

{(Z)-4-[(R)-2-Oxo-6-(3-oxo-4-phenyl-butyl)-piperidin-1-yl]-but-2-enyloxy}-acetic Acid Methyl Ester A solution of {(Z)-4-[(R)-2-oxo-6-((E)-3-oxo-4-phenyl-but-1-enyl)-piperidin-1-yl]-but-2-enyloxy}-acetic acid methyl ester (24.6 mg, 0.064 mmol) in CH$_3$CN (1.5 mL) was added via cannula to hydrido(triphenylphosphine)copper(I) hexamer (125 mg, 0.064 mmol) at −40° C. After 1 h at −40° C., the reaction was allowed to warm to rt. After 3 h at rt, the reaction was quenched by addition of a solution of NH$_4$OH and saturated aqueous NH$_4$Cl (1:1, 6 mL). The mixture was extracted with EtOAc (3×10 mL). The combined organic phase was washed with brine (20 mL), dried (Na$_2$SO$_4$), filtered and concentrated in vacuo. Purification of the residue by flash column chromatography on silica gel (20% →70% EtOAc/CH$_2$Cl$_2$, gradient) afforded 19.6 mg (79%) of the title compound.

EXAMPLE 63

{(Z)-4-[(R)-2-Oxo-6-(3-oxo-4-phenyl-butyl)-piperidin-1-yl]-but-2-enyloxy}-acetic Acid In accordance with the procedure of example 2, {(Z)-4-[(R)-2-oxo-6-(3-oxo-4-phenyl-butyl)-piperidin-1-yl]-but-2-enyloxy}-acetic acid methyl ester (6.1 mg, 0.016 mmol) was converted into 1.7 mg (29%) of the title compound.

EXAMPLE 64

{(Z)-4-[(R)-2-(3-Hydroxy-4-phenyl-butyl)-6-oxo-piperidin-1-yl]-but-2-enyloxy}-acetic Acid Methyl Ester Sodium borohydride (2 mg, 0.053 mmol), followed by MeOH (0.15 mL), was added to a solution of {(Z)-4-[(R)-2-oxo-6-(3-oxo-4-phenyl-butyl)-piperidin-1-yl]-but-2-enyloxy}-acetic acid methyl ester (11.5 mg, 0.030 mmol) in CH$_2$Cl$_2$ (0.5 mL) at 0° C. The mixture was allowed to warm to rt. After 30 min at rt, the reaction was quenched with aqueous HCl (0.5 M) and extracted with EtOAc (3×7 mL).

The combined organic phase was dried (Na$_2$SO$_4$), filtered and concentrated in vacuo to afford 10.1 mg (87%) of the title compound.

EXAMPLE 65

{(Z)-4-[(R)-2-(3-Hydroxy-4-phenyl-butyl)-6-oxo-piperidin-1-yl]-but-2-enyloxy}-acetic Acid In accordance with the procedure of example 2, {(Z)-4-[(R)-2-(3-hydroxy-4-phenyl-butyl)-6-oxo-piperidin-1-yl]-but-2-enyloxy}-acetic acid methyl ester (6.2 mg, 0.016 mmol) was converted into 1.6 mg (27%) of the title compound.

EXAMPLE 66

(4-{(R)-2-[(E)-4-(3-Chlorophenyl)-3-hydroxy-but-1-enyl]-6-oxo-piperidin-1-yl}-butoxy)-acetic Acid (FIG. 3)

Step 1. [(Z)-4-((R)-2-Hydroxymethyl-6-oxo-piperidin-1-yl)-but-2-enyloxy]-acetic Acid Ethyl Ester p-Toluenesulfonic acid hydrate (267 mg, 1.40 mmol) was added to a solution of {(Z)-4-[(R)-2-(1-ethoxyethoxymethyl)-6-oxo-piperidin-1-yl]-but-2-enyloxy}-acetic acid ethyl ester (from example 50, step 2, 477 mg, 1.33 mmol) in EtOH (6 mL). After 18 h at rt, the reaction was concentrated in vacuo and quenched with saturated aqueous NaHCO$_3$ (20 mL). The mixture was extracted with CH$_2$Cl$_2$ (3×15 mL). The combined organic phase was dried (Na$_2$SO$_4$), filtered and concentrated in vacuo. Purification of the residue by flash column chromatography on silica gel (CH$_2$Cl$_2$→3% MeOH/CH$_2$Cl$_2$, gradient) afforded 290 mg (76%) of [(Z)-4-((R)-2-hydroxymethyl-6-oxo-piperidin-1-yl)-but-2-enyloxy]-acetic acid ethyl ester.

Step 2. [4-((R)-2-Hydroxymethyl-6-oxo-piperidin-1-yl)-butoxy]-acetic Acid Ethyl Ester Palladium on carbon (10 wt. %, 15 mg) was added to a solution of [(Z)-4-((R)-2-hydroxymethyl-6-oxo-piperidin-1-yl)-but-2-enyloxy]-acetic acid ethyl ester (290 mg, 1.02 mmol) in EtOH (3.0 mL). A hydrogen atmosphere was established by evacuating and refilling with hydrogen (3×) and the reaction mixture was stirred under a balloon of hydrogen for 3 h. The reaction mixture was filtered through celite, washing with EtOH, and the filtrate was concentrated in vacuo to afford 295 mg (quant. crude) of [4-((R)-2-hydroxymethyl-6-oxo-piperidin-1-yl)-butoxy]-acetic acid ethyl ester.

Step 3. [4-((R)-2-Formyl-6-oxo-piperidin-1-yl)-butoxy]-acetic Acid Ethyl Ester 1-(3-(Dimethylaminopropyl)-3-ethylcarbodiimide hydrochloride (EDCI, 505 mg, 2.63 mmol) and DMSO (0.25 mL, 3.52 mmol) were added sequentially to a solution of [4-((R)-2-hydroxymethyl-6-oxo-piperidin-1-yl)-butoxy]-acetic acid ethyl ester (252 mg, 0.88 mmol) in benzene (5 mL). The mixture was cooled to 0° C. and pyridinium trifluoroacetate (187 mg, 0.97 mmol) was added. The reaction was allowed to warm to rt and then was stirred at rt for 4.25 h. The solution was decanted from the oily residue and the residue was washed with benzene (3×5 mL). The combined benzene phases were concentrated in vacuo to afford crude 4-((R)-2-formyl-6-oxo-piperidin-1-yl)-butoxy]-acetic acid ethyl ester that was used without further purification.

Step 4. (4-{(R)-2-[(E)-4-(3-Chlorophenyl)-3-oxo-but-1-enyl]-6-oxo-piperidin-1-yl}-butoxy)-acetic Acid Ethyl Ester Sodium hydride (60% dispersion in oil, 35 mg, 0.88 mmol) was added to a solution of [3-(3-chlorophenyl)-2-oxopropyl]-phosphonic acid dimethyl ester (221 mg, 0.80 mmol) in THF (2.0 mL) at 0° C. After 1 h at 0° C., [4-((R)-2-formyl-6-oxo-piperidin-1-yl)-butoxy]-acetic acid ethyl ester (0.88 mmol, crude) in THF (2 mL) was added via cannula. The reaction was allowed to warm to rt. After 18 h at rt, the reaction was quenched with aqueous acetic acid (50%, 10 mL) and extracted with EtOAc (3×20 mL). The combined organic phase was washed with brine (25 mL), dried (Na$_2$SO$_4$), filtered and concentrated in vacuo. Purification of the residue by flash column chromatography on silica gel (20% →40% EtOAc/CH$_2$Cl$_2$, gradient) afforded 117 mg (34%) of (4-{(R)-2-[(E)-4-(3-chlorophenyl)-3-oxo-but-1-enyl]-6-oxo-piperidin-1-yl}-butoxy)-acetic acid ethyl ester.

Step 5. (4-{(R)-2-[(E)-4-(3-Chlorophenyl)-3-hydroxy-but-1-enyl]-6-oxo-piperidin-1-yl}-butoxy)-acetic Acid Ethyl Ester Sodium borohydride (10 mg, 0.26 mmol) followed by EtOH (0.25 mL) was added to a solution of (4-{(R)-2-[(E)-4-(3-chlorophenyl)-3-oxo-but-1-enyl]-6-oxo-piperidin-1-yl}-butoxy)-acetic acid ethyl ester (110 mg, 0.25 mmol) in CH$_2$Cl$_2$ (1.0 mL) at 0° C. After 1 h at 0° C. the reaction was quenched with 1 N aqueous HCl. The reaction mixture was extracted with CH$_2$Cl$_2$ (3×10 mL), then the combined extracts were dried (Na$_2$SO$_4$), filtered and concentrated in vacuo. Purification of the residue by flash column chromatography on silica gel (CH$_2$Cl$_2$→2% MeOH/CH$_2$Cl$_2$) afforded 88 mg (80%) of (4-{(R)-2-[(E)-4-(3-chlorophenyl)-3-hydroxy-but-1-enyl]-6-oxo-piperidin-1-yl}-butoxy)-acetic acid ethyl ester.

Step 6. (4-{(R)-2-[(E)-4-(3-Chlorophenyl)-3-hydroxy-but-1-enyl]-6-oxo-piperidin-1-yl}-butoxy)-acetic Acid In accordance with the procedure of example 2, (4-{(R)-2-[(E)-4-(3-chlorophenyl)-3-hydroxy-but-1-enyl]-6-oxo-piperidin-1-yl}-butoxy)-acetic acid ethyl ester (88 mg, 0.20 mmol) was converted into 44 mg (54%) of the title compound.

EXAMPLE 67

2-(4-{(R)-2-[(E)-4-(3-Chlorophenyl)-3-hydroxy-but-1-enyl]-6-oxo-piperidin-1-yl}-butoxy)-acetamide Triethylamine (8.8 µL, 0.063 mmol) was added to a solution of (4-{(R)-2-[(E)-4-(3-chlorophenyl)-3-hydroxy-but-1-enyl]-6-oxo-piperidin-1-yl}-butoxy)-acetic acid (12.4 mg, 0.030 mmol) in CH$_2$Cl$_2$ (0.2 mL). After cooling to 0° C., the reaction mixture was treated with ethyl chloroformate (3.2 µL, 0.033 mmol). After 1 h at 0° C., ammonia (0.5 M in 1,4-dioxane, 0.32 mL, 0.16 mmol) was added and the reaction mixture was allowed to warm to rt. After 18 h at rt, the reaction mixture was treated with saturated aqueous NaHCO$_3$ (5 mL) and extracted with CH$_2$Cl$_2$ (3×5 mL). The combined extracts were dried (Na$_2$SO$_4$), filtered and concentrated in vacuo. Purification of the residue by flash column chromatography on silica gel (5% →20% MeOH/ CH$_2$Cl$_2$, gradient) afforded 1.3 mg (11%) of the title compound.

EXAMPLE 68

(4-{(R)-2-[(E)-4-(3-Chlorophenyl)-3-hydroxy-but-1-enyl]-6-oxo-piperidin-1-yl}-butoxy)-acetic Acid Isopropyl Ester 1,8-Diazabicyclo[5.4.0]undec-7-ene (DBU, 16 µL, 0.11 mmol) was added to a solution of (4-{(R)-2-[(E)-4-(3-chlorophenyl)-3-hydroxy-but-1-enyl]-6-oxo-piperidin-1-yl}-butoxy)-acetic acid (29 mg, 0.071 mmol) in acetone (0.5 mL). After 5 min, 2-iodopropane (35 µL, 0.35 mmol) was added. After 17 h, the reaction mixture was concentrated in vacuo, EtOAc (15 mL) was added and the resultant mixture was washed with 0.5 M aqueous HCl (5 mL), saturated aqueous NaHCO$_3$ (5 mL) and brine (5 mL). The organic phase was then dried (Na$_2$SO$_4$), filtered and concentrated in vacuo. Purification of the residue by flash column chromatography on silica gel (CH$_2$Cl$_2$→5% MeOH/CH$_2$Cl$_2$, gradient) afforded 16 mg (50%) of the title compound.

EXAMPLE 69

(4-{(R)-2-[(E)-4-(3-Chlorophenyl)-3-oxo-but-1-enyl]-6-oxo-piperidin-1-yl}-but-2-ynyloxy)-acetic Acid Methyl Ester Step 1. (4-Hydroxy-but-2-ynyloxy)-acetic Acid Methyl Ester Sodium hydride (60% dispersion in oil, 2.32 g, 58 mmol) was added to a solution of 2-butyne-1,4-diol (5.0 g, 58 mmol) in THF (60 mL) at 0° C. under nitrogen. After 1 h at 0° C., methyl bromomethylacetate (5.5 mL, 58 mmol) was added and the reaction was allowed to warm to rt. After 18 h at rt, the reaction was quenched with 1 N HCl (60 mL) and extracted with EtOAc (3×100 mL). The combined extracts were washed with brine (1×100 mL), dried (MgSO$_4$), filtered and concentrated in vacuo. Purification of the residue by flash column chromatography on silica gel (CH$_2$Cl$_2$→5% MeOH/CH$_2$Cl$_2$, gradient) afforded 3.2 g (35%) of (4-hydroxy-but-2-ynyloxy)-acetic acid methyl ester.

Step 2. (4-Iodo-but-2-ynyloxy)-acetic Acid Methyl Ester

Triphenylphosphine (6.23 g, 23.8 mmol), iodine (6.03 g, 23.8 mmol) and imidazole (1.57 g, 23.8 mmol) were added sequentially to a solution of (4-hydroxy-but-2-ynyloxy)-acetic acid methyl ester (3.13 g, 19.8 mmol) in CH$_2$Cl$_2$ (30 mL). After 1 h at rt, the reaction was filtered through activity I basic alumina, washing with 20% EtOAc/Hexane. The filtrate was concentrated in vacuo then purified by flash column chromatography on silica gel (Hexane→20% EtOAc/Hexane, gradient) to afford 2.05 g (39%) of (4-iodo-but-2-ynyloxy)-acetic acid methyl ester.

Step 3. {4-[(R)-2-(1-Ethoxy-ethoxymethyl)-6-oxo-piperidin-1-yl]-but-2-ynyloxy}-acetic Acid Methyl Ester Sodium hydride (60% dispersion in oil, 278 mg, 6.95 mmol) was added to a solution of (R)-6-(1-ethoxyethoxymethyl)-piperidin-2-one (from example 50, step 1, 1.40 g, 6.96 mmol) in DMF (10 mL) at 0° C. After 1 h at 0° C., (4-iodo-but-2-ynyloxy)-acetic acid methyl ester (2.05 g, 7.65 mmol) in DMF (10 mL) was added via cannula and the reaction was allowed to warm to rt. After 15 min at rt, the reaction mixture solidified, so more DMF (3 mL) was added. After 18 h at rt, the reaction was treated with saturated aqueous NaHCO$_3$ (50 mL) and extracted with EtOAc (3×70 mL). The combined extracts were washed with water (2×50 mL) and brine (2×50 mL) then dried (MgSO$_4$), filtered and concentrated in vacuo. Purification of the residue by flash column chromatography on silica gel (20% →50% EtOAc/ CH$_2$Cl$_2$, gradient) afforded 500 mg (21%) of {4-[(R)-2-(1-ethoxy-ethoxymethyl)-6-oxo-piperidin-1-yl]-but-2-ynyloxy}-acetic acid methyl ester.

Step 4. [4-((R)-2-Hydroxymethyl-6-oxo-piperidin-1-yl)-but-2-ynyloxy]-acetic Acid Methyl Ester p-Toluenesulfonic acid hydrate (289 mg, 1.52 mmol) was added to a solution of {4-[(R)-2-(1-ethoxy-ethoxymethyl)-6-oxo-piperidin-1-yl]-but-2-ynyloxy}-acetic acid methyl ester (494 mg, 1.45 mmol) in MeOH (5.0 mL) at rt. After 20 h at rt, the mixture was concentrated in vacuo, treated with saturated aqueous NaHCO$_3$ (20 mL) and extracted with CH$_2$Cl$_2$ (3×20 mL). The combined organic phase was dried (MgSO$_4$), filtered and concentrated in vacuo. Purification of the residue by flash column chromatography on silica gel (CH$_2$Cl$_2$→3% MeOH/CH$_2$Cl$_2$, gradient) afforded 100 mg (26%) of [4-((R)-2-hydroxymethyl-6-oxo-piperidin-1-yl)-but-2-ynyloxy)-acetic acid methyl ester.

Step 5. [4-((R)-2-Formyl-6-oxo-piperidin-1-yl)-but-2-ynyloxy]-acetic Acid Methyl Ester EDCI (214 mg, 1.12 mmol) was added to a solution of [4-((R)-2-hydroxymethyl-6-oxo-piperidin-1-yl)-but-2-ynyloxy]-acetic acid methyl ester (100 mg, 0.37 mmol) in benzene (3.5 mL). The reaction mixture was cooled to 0° C. and DMSO (0.11 mL, 1.55 mmol) was added. After 5 min at 0° C., pyridinium trifluoroacetate (79 mg, 0.41 mmol) was added. The reaction was allowed to warm to rt and then was stirred at rt for 3 h. The solution was decanted from the oily residue and the residue was washed with benzene (3×3 mL). The combined benzene phases were concentrated in vacuo to afford crude [4-((R)-2-formyl-6-oxo-piperidin-1-yl)-but-2-ynyloxy]-acetic acid methyl ester, which was used without further purification.

Step 6. (4-{(R)-2-[(E)-4-(3-Chlorophenyl)-3-oxo-but-1-enyl]-6-oxo-piperidin-1-yl}-but-2-ynyloxy)-acetic Acid Methyl Ester Sodium hydride (60% dispersion in oil, 15 mg, 0.39 mmol) was added to a solution of [3-(3-chlorophenyl)-2-oxopropyl]-phosphonic acid dimethyl ester (97 mg, 0.35 mmol) in THF (1.5 mL) at 0° C. After 1 h at 0° C., a solution of [4-((R)-2-formyl-6-oxo-piperidin-1-yl)-but-2-ynyloxy]-acetic acid methyl ester (0.37 mmol, crude) in THF (1.5 mL) was added via cannula. The reaction was allowed to warm to rt. After 18 h at rt, the reaction was quenched with aqueous acetic acid (50%, 15 mL) and extracted with EtOAc (3×15 mL). The combined organic phase was washed with brine (20 mL), dried (MgSO$_4$), filtered and concentrated in vacuo. Purification of the residue by flash column chromatography on silica gel (20% →30% EtOAc/CH$_2$Cl$_2$, gradient) afforded 100 mg (68%) of the title compound.

EXAMPLE 70

(4-{(R)-2-[(E)-4-(3-Chlorophenyl)-3-oxo-but-1-enyl]-6-oxo-piperidin-1-yl}-but-2-ynyloxy)-acetic Acid In accordance with the procedure of example 2, (4-{(R)-2-[(E)-4-(3-chlorophenyl)-3-oxo-but-1-enyl]-6-oxo-piperidin-1-yl}-but-2-ynyloxy)-acetic acid methyl ester (8.0 mg, 0.019 mmol) was converted into 7.0 mg (91%) of the title compound.

EXAMPLES 71 AND 72

(4-{(R)-2-[(E)-4-(3-Chlorophenyl)-3-hydroxy-but-1-enyl]-6-oxo-piperidin-1-yl}-but-2-ynyloxy)-acetic acid methyl ester and (R)-6-[(E)-4-(3-Chlorophenyl)-3-hydroxy-but-1-enyl]-1-[4-(2-hydroxyethoxy)-but-2-ynyl]-piperidin-2-one Sodium borohydride (5 mg, 0.13 mmol) followed by MeOH (0.5 mL) was added to a solution of (4-{(R)-2-[(E)-4-(3-chlorophenyl)-3-oxo-but-1-enyl]-6-oxo-piperidin-1-yl}-but-2-ynyloxy)-acetic acid methyl ester (48 mg, 0.11 mmol) in CH$_2$Cl$_2$ (1.0 mL) at 0° C. After 20 min at 0° C. the reaction was quenched with 0.5 N aqueous HCl. The reaction mixture was extracted with CH$_2$Cl$_2$ (3×10 mL), then the combined extracts were dried (MgSO$_4$), filtered and concentrated in vacuo. Purification of the residue by flash column chromatography on silica gel (CH$_2$Cl$_2$→2% MeOH/CH$_2$Cl$_2$) followed by preparative thin layer chromatography (5% MeOH/CH$_2$Cl$_2$) afforded 22 mg (46%) of (4-{(R)-2-[(E)-4-(3-chlorophenyl)-3-hydroxy-but-1-enyl]-6-oxo-piperidin-1-yl}-but-2-ynyloxy)-acetic acid methyl ester and 1.7 mg (4%) of (R)-6-[(E)-4-(3-chlorophenyl)-3-hydroxy-but-1-enyl]-1-[4-(2-hydroxyethoxy)-but-2-ynyl]-piperidin-2-one.

EXAMPLE 73

(4-{(R)-2-[(E)-4-(3-Chlorophenyl)-3-hydroxy-but-1-enyl]-6-oxo-piperidin-1-yl}-but-2-ynyloxy)-acetic Acid In accordance with the procedure of example 2, (4-{(R)-2-[(E)-4-(3-chlorophenyl)-3-hydroxy-but-1-enyl]-6-oxo-piperidin-1-yl}-but-2-ynyloxy)-acetic acid methyl ester (18 mg, 0.043 mmol) was converted into 15.6 mg (90%) of the title compound.

EXAMPLE 74

(4-{(R)-2-[(E)-4-(3-Chlorophenyl)-3-hydroxy-but-1-enyl]-6-oxo-piperidin-1-yl}-but-2-ynyloxy)-acetic Acid Isopropyl Ester DBU (6.6 μL, 0.044 mmol) was added to a solution of (4-{(R)-2-[(E)-4-(3-chlorophenyl)-3-hydroxy-but-1-enyl]-6-oxo-piperidin-1-yl}-but-2-ynyloxy)-acetic acid (12 mg, 0.030 mmol) in acetone (0.3 mL). After 5 min, 2-iodopropane (15 μL, 0.15 mmol) was added. After 19 h, the reaction mixture was concentrated in vacuo, 0.5 M aqueous HCl (5 mL) was added and the mixture was extracted with EtOAc (3×5 mL). The combine organic phase was washed with saturated aqueous NaHCO$_3$ (10 mL) and brine (10 mL) then dried (MgSO$_4$), filtered and concentrated in vacuo. Purification of the residue by flash column chromatography on silica gel (CH$_2$Cl$_2$→3% MeOH/CH$_2$Cl$_2$, gradient) afforded 7.9 mg (60%) of the title compound.

EXAMPLE 75

(4-{(R)-2-[4-(3-Chlorophenyl)-3-oxo-butyl]-6-oxo-piperidin-1-yl}-but-2-ynyloxy)-acetic Acid Methyl Ester A solution of (4-{(R)-2-[(E)-4-(3-chlorophenyl)-3-oxo-but-1-enyl]-6-oxo-piperidin-1-yl}-but-2-ynyloxy)-acetic acid methyl ester (35 mg, 0.084 mmol) in toluene (2 mL) was added via cannula to a round-bottomed flask containing hydrido(triphenylphosphine)copper(I) hexamer (164 mg, 0.084 mmol) at −40° C. under nitrogen. The reaction was allowed to warm to rt and stirred for 3 h. The reaction was quenched with NH$_4$OH/NH$_4$Cl (1:1, 5 mL) and extracted with EtOAc (3×7 mL). The combined extracts were dried (MgSO$_4$), filtered and concentrated in vacuo. Purification of the residue by flash column chromatography on silica gel (20% →50% EtOAc/CH$_2$Cl$_2$, gradient) followed by preparative thin layer chromatography (silica, 80% EtOAc/CH$_2$Cl$_2$) afforded 12 mg (34%) of the title compound.

EXAMPLE 76

(4-{(R)-2-[4-(3-Chlorophenyl)-3-oxo-butyl]-6-oxo-piperidin-1-yl}-but-2-ynyloxy)-acetic Acid In accordance with the procedure of example 2, (4-{(R)-2-[4-(3-chlorophenyl)-3-oxo-butyl]-6-oxo-piperidin-1-yl}-but-2-ynyloxy)-acetic acid methyl ester (4.7 mg, 0.011 mmol) was converted into 2.8 mg (62%) of the title compound.

EXAMPLE 77

(4-{(R)-2-[4-(3-Chlorophenyl)-3-hydroxy-butyl]-6-oxo-piperidin-1-yl}-but-2-ynyloxy)-acetic Acid Methyl Ester Sodium borohydride (2 mg, 0.053 mmol) followed by MeOH (0.1 mL) was added to a solution of (4-{(R)-2-[4-(3-chlorophenyl)-3-oxo-butyl]-6-oxo-piperidin-1-yl}-but-2-ynyloxy)-acetic acid methyl ester (5 mg, 0.012 mmol) in CH$_2$Cl$_2$ (0.3 mL) at 0° C. After 10 min at 0° C. the reaction was quenched with aqueous HCl (0.25 M, 3 mL). The reaction mixture was extracted with CH$_2$Cl$_2$ (3×4 mL), then the combined extracts were dried (MgSO$_4$), filtered and concentrated in vacuo. Purification of the residue by flash column chromatography on silica gel (CH$_2$Cl$_2$→2% MeOH/CH$_2$Cl$_2$) afforded 4.6 mg (92%) of the title compound.

EXAMPLE 78

(4-{(R)-2-[4-(3-Chlorophenyl)-3-hydroxy-butyl]-6-oxo-piperidin-1-yl}-but-2-ynyloxy)-acetic Acid In accordance with the procedure of example 2, (4-{(R)-2-[4-(3-chlorophenyl)-3-hydroxy-butyl]-6-oxo-piperidin-1- yl}-but-2-ynyloxy)-acetic acid methyl ester (3.5 mg, 0.0083 mmol) was converted into 1.5 mg (44%) of the title compound.

EXAMPLE 79

{4-[(R)-2-Oxo-6-((E)-3-oxo-4-phenyl-but-1-enyl)-piperidin-1-yl]-but-2-ynyloxy}-acetic Acid Methyl Ester Sodium hydride (60% dispersion in oil, 41 mg, 1.03 mmol) was added to a solution of dimethyl 2-oxo-3-phenylpropylphosphonate (247 mg, 1.02 mmol) in THF (4 mL) at 0° C. After 1 h at 0° C., a solution of [4-((R)-2-formyl-6-oxo-piperidin-1-yl)-but-2-ynyloxy]-acetic acid methyl ester (1.23 mmol, crude, prepared as in Example 69, step 4) in THF (3 mL) was added via cannula. The reaction was allowed to warm to rt. After 18 h at rt, the reaction was quenched with aqueous acetic acid (50%, 30 mL) and extracted with EtOAc (3×40 mL). The combined organic phase was washed with brine (50 mL), dried (Na$_2$SO$_4$), filtered and concentrated in vacuo. Purification of the residue by flash column chromatography on silica gel (30% →50% EtOAc/CH$_2$Cl$_2$, gradient) afforded 122 mg (31%) of the title compound.

EXAMPLE 80

{4-[(R)-2-Oxo-6-((E)-3-oxo-4-phenyl-but-1-enyl)-piperidin-1-yl]-but-2-ynyloxy}-acetic Acid In accordance with the procedure of example 2, {4-[(R)-2-oxo-6-((E)-3-oxo-4-phenyl-but-1-enyl)-piperidin-1-yl]-but-2-ynyloxy}-acetic acid methyl ester (6.8 mg, 0.018 mmol) was converted into 1.1 mg (17%) of the title compound.

EXAMPLES 81 AND 82

{4-[(R)-2-((E)-3-Hydroxy-4-phenyl-but-1-enyl)-6-oxo-piperidin-1-yl]-but-2-ynyloxy}-acetic Acid Methyl Ester and (R)-1-[4-(2-hydroxy-ethoxy)-but-2-ynyl]-6-((E)-3-hydroxy-4-phenyl-but-1-enyl)-piperidin-2-one Sodium borohydride (24 mg, 0.63 mmol) followed by MeOH (1 mL) was added to a solution of {4-[(R)-2-oxo-6-((E)-3-oxo-4-phenyl-but-1-enyl)-piperidin-1-yl]-but-2-ynyloxy}-acetic acid methyl ester (82 mg, 0.21 mmol) in CH$_2$Cl$_2$ (2 mL) at 0° C. After 5 min at 0° C. the reaction was quenched with aqueous HCl (0.2 M, 10 mL). The reaction mixture was extracted with CH$_2$Cl$_2$ (3×10 mL), then the combined extracts were dried (Na$_2$SO$_4$), filtered and concentrated in vacuo. Purification of the residue by flash column chromatography on silica gel (CH$_2$Cl$_2$→3% MeOH/CH$_2$Cl$_2$) afforded 56.5 mg (69%) of {4-[(R)-2-((E)-3-hydroxy-4-phenyl-but-1-enyl)-6-oxo-piperidin-1-yl]-but-2-ynyloxy}-acetic acid methyl ester and 11 mg (14%) of (R)-1-[4-(2-hydroxy-ethoxy)-but-2-ynyl]-6-((E)-3-hydroxy-4-phenyl-but-1-enyl)-piperidin-2-one.

EXAMPLE 83

{4-[(R)-2-((E)-3-Hydroxy-4-phenyl-but-1-enyl)-6-oxo-piperidin-1-yl]-but-2-ynyloxy}-acetic Acid In accordance with the procedure of example 2, {4-[(R)-2-((E)-3-hydroxy-4-phenyl-but-1-enyl)-6-oxo-piperidin-1-yl]-but-2-ynyloxy}-acetic acid methyl ester (54.4 mg, 0.14 mmol) was converted into 31 mg (59%) of the title compound

EXAMPLE 84

{4-[(R)-2-((E)-3-Hydroxy-4-phenyl-but-1-enyl)-6-oxo-piperidin-1-yl]-but-2-ynyloxy}-acetic Acid Isopropyl Ester DBU (10 µL, 0.067 mmol) was added to a solution of {4-[(R)-2-((E)-3-hydroxy-4-phenyl-but-1-enyl)-6-oxo-piperidin-1-yl]-but-2-ynyloxy}-acetic acid (16.6 mg, 0.045 mmol) in acetone (0.5 mL). After 5 min, 2-iodopropane (22.5 µL, 0.225 mmol) was added. After 18 h, the reaction mixture was diluted with EtOAc (25 mL) and washed sequentially with aqueous HCl (0.1 M, 10 mL), saturated aqueous NaHCO$_3$ (10 mL) and brine (10 mL). The organic phase was dried (Na$_2$SO$_4$), filtered and concentrated in vacuo to afford 10.6 mg (57%) of the title compound.

EXAMPLE 85

2-{4-[(R)-2-((E)-3-Hydroxy-4-phenyl-but-1-enyl)-6-oxo-piperidin-1-yl]-but-2-ynyloxy}-acetamide Triethylamine (9.4 µL, 0.067 mmol) and ethyl chloroformate (3.1 µL, 0.032 mmol) were added sequentially to a solution of {4-[(R)-2-((E)-3-hydroxy-4-phenyl-but-1-enyl)-6-oxo-piperidin-1-yl]-but-2-ynyloxy}-acetic acid (11.8 mg, 0.032 mmol) in CH$_2$Cl$_2$ (0.2 mL) at 0° C. After 1 h at 0° C., ammonia (0.5 M in 1,4-dioxane, 0.32 mL, 0.16 mmol) was added and the reaction mixture was allowed to warm to rt. After 17 h at rt, the reaction mixture was treated with saturated aqueous NaHCO$_3$ (10 mL) and extracted with CH$_2$Cl$_2$ (3×10 mL). The combined extracts were dried (Na$_2$SO$_4$), filtered and concentrated in vacuo to afford 11 mg (93%) of the title compound.

EXAMPLE 86

{4-[(R)-2-Oxo-6-(3-oxo-4-phenyl-butyl)-piperidin-1-yl]-but-2-ynyloxy}-acetic Acid Methyl Ester A solution of {4-[(R)-2-Oxo-6-((E)-3-oxo-4-phenyl-but-1-enyl)-piperidin-1-yl]-but-2-ynyloxy}-acetic acid methyl ester (30 mg, 0.078 mmol) in toluene (2 mL) was added via cannula to a round-bottomed flask containing hydrido(triphenylphosphine)copper(I) hexamer (154 mg, 0.078 mmol) at −40° C. under nitrogen. The reaction was allowed to warm to rt and stirred for 2.5 h. The reaction was quenched with NH$_4$OH/NH$_4$Cl (1:1, 8 mL) and extracted with EtOAc (3×10 mL). The combined extracts were dried washed with brine (10 mL) then dried (Na$_2$SO$_4$), filtered and concentrated in vacuo. Purification of the residue by flash column chromatography on silica gel (20% →40% EtOAc/CH$_2$Cl$_2$, gradient) afforded 23.4 mg (78%) of the title compound.

EXAMPLE 87

{4-[(R)-2-Oxo-6-(3-oxo-4-phenyl-butyl)-piperidin-1-yl]-but-2-ynyloxy}-acetic Acid In accordance with the procedure of example 2, {4-[(R)-2-oxo-6-(3-oxo-4-phenyl-butyl)-piperidin-1-yl]-but-2-ynyloxy}-acetic acid methyl ester (6.5 mg, 0.017 mmol) was converted into 5.2 mg (83%) of the title compound.

EXAMPLES 88 AND 89

{4-[(R)-2-(3-Hydroxy-4-phenyl-butyl)-6-oxo-piperidin-1-yl]-but-2-ynyloxy}-acetic Acid Methyl Ester and (R)-1-[4-(2-hydroxy-ethoxy)-but-2-ynyl]-6-(3-hydroxy-4-phenyl-butyl)-piperidin-2-one Sodium borohydride (4.4 mg, 0.12 mmol) followed by MeOH (0.2 mL) was added to a solution of {4-[(R)-2-oxo-6-(3-oxo-4-phenyl-butyl)-piperidin-1-yl]-but-2-ynyloxy}-acetic acid methyl ester (15 mg, 0.039 mmol) in $CH_2Cl_2$ (0.6 mL) at 0° C. After 5 min at 0° C. the reaction was quenched with aqueous HCl (0.2 M, 5 mL). The reaction mixture was extracted with $CH_2Cl_2$ (3×5 mL), then the combined extracts were dried ($Na_2SO_4$), filtered and concentrated in vacuo. Purification of the residue by flash column chromatography on silica gel ($CH_2Cl_2 \rightarrow 5\%$ MeOH/$CH_2Cl_2$) afforded 13 mg (86%) of {4-[(R)-2-(3-hydroxy-4-phenyl-butyl)-6-oxo-piperidin-1-yl]-but-2-ynyloxy}-acetic acid methyl ester and 2 mg (14%) of (R)-1-[4-(2-hydroxy-ethoxy)-but-2-ynyl]-6-(3-hydroxy-4-phenyl-butyl)-piperidin-2-one.

EXAMPLE 90

{4-[(R)-2-(3-Hydroxy-4-phenyl-butyl)-6-oxo-piperidin-1-yl]-but-2-ynyloxy}-acetic Acid In accordance with the procedure of example 2, {4-[(R)-2-(3-hydroxy-4-phenyl-butyl)-6-oxo-piperidin-1-yl]-but-2-ynyloxy}-acetic acid methyl ester (11 mg, 0.028 mmol) was converted into 3.8 mg (36%) of the title compound.

EXAMPLE 91

{4-[(R)-2-Oxo-6-((E)-3-oxo-4-phenyl-but-1-enyl)-piperidin-1-yl]-but-2-ynyloxy}-acetonitrile

Step 1. (4-Hydroxy-but-2-ynyloxy)-acetonitrile

Sodium hydride (60% dispersion in oil, 7.5 g, 188 mmol) was added to a solution of 2-butyne-1,4-diol (16.1 g, 187 mmol) in THF (150 mL) at 0° C. under nitrogen. After 1 h at 0° C., bromoacetonitrile (8.33 mL, 120 mmol) was added slowly and the reaction was allowed to warm to rt. After 22 h at rt, the reaction was quenched with 1 N HCl (150 mL) and extracted with EtOAc (3×150 mL). The combined extracts were washed with brine (150 mL), dried ($Na_2SO_4$), filtered and concentrated in vacuo. Purification of the residue by flash column chromatography on silica gel ($CH_2Cl_2 \rightarrow 2\%$ MeOH/$CH_2Cl_2$, gradient) afforded 4.35 g (29%) of (4-hydroxy-but-2-ynyloxy)-acetonitrile.

Step 2. (4-Iodo-but-2-ynyloxy)-acetonitrile

Triphenylphosphine (10.94 g, 41.7 mmol) and iodine (10.55 g, 41.6 mmol were added sequentially to a solution of (4-hydroxy-but-2-ynyloxy)-acetonitrile (4.35 g, 34.8 mmol) in $CH_2Cl_2$ (100 mL). The reaction mixture became homogeneous after 5 min at rt and imidazole (2.76 g, 40.5 mmol) was added slowly in small portions. After 1.5 h at rt, the reaction was filtered through activity I basic alumina, washing with 20% EtOAc/Hexane. The filtrate was concentrated in vacuo then purified by flash column chromatography on silica gel (hexane$\rightarrow$10% EtOAc/hexane, gradient) to afford 7.51 g (92%) of (4-iodo-but-2-ynyloxy)-acetonitrile.

Step 3. {4-[(R)-2-(1-Ethoxy-ethoxymethyl)-6-oxo-piperidin-1-yl]-but-2-ynyloxy}-acetonitrile Sodium hydride (60% dispersion in oil, 600 mg, 15.0 mmol) was added to a solution of (R)-6-(1-ethoxyethoxymethyl)-piperidin-2-one (from example 50, step 1, 3.00 g, 14.9 mmol) in DMF (20 mL) at 0° C. After 1 h at 0° C., (4-iodo-but-2-ynyloxy)-acetonitrile (3.50 g, 14.9 mmol) in DMF (10 mL) was added via cannula and the reaction was allowed to warm to rt. After 16.5 h at rt, the reaction was treated with saturated aqueous $NH_4Cl$ (100 mL) and extracted with EtOAc (3×100 mL). The combined extracts were washed with water (2×100 mL) and brine (2×100 mL) then dried ($Na_2SO_4$), filtered and concentrated in vacuo. Purification of the residue by flash column chromatography on silica gel ($CH_2Cl_2 \rightarrow 50\%$ EtOAc/$CH_2Cl_2$, gradient) afforded 1.83 g (40%) of {4-[(R)-2-(1-ethoxy-ethoxymethyl)-6-oxo-piperidin-1-yl]-but-2-ynyloxy}-acetonitrile.

Step 4. [4-((R)-2-Hydroxymethyl-6-oxo-piperidin-1-yl)-but-2-ynyloxy]-acetonitrile Trifluoroacetic acid (0.5 mL, 6.5 mmol) was added to a solution of {4-[(R)-2-(1-ethoxy-ethoxymethyl)-6-oxo-piperidin-1-yl]-but-2-ynyloxy}-acetonitrile (290 mg, 0.94 mmol) in $CH_2Cl_2$ (3 mL). After 1 h at rt, the reaction mixture was quenched with saturated aqueous $NaHCO_3$ (20 mL) and extracted with $CH_2Cl_2$ (3×20 mL). Combined extracts were dried ($Na_2SO_4$), filtered and concentrated in vacuo. Purification of the residue by flash column chromatography on silica gel ($CH_2Cl_2 \rightarrow 3\%$ MeOH/$CH_2Cl_2$, gradient) afforded 118 mg (53%) of [4-((R)-2-hydroxymethyl-6-oxo-piperidin-1-yl)-but-2-ynyloxy]-acetonitrile.

Step 5. [4-((R)-2-Formyl-6-oxo-piperidin-1-yl)-but-2-ynyloxy]-acetonitrile

EDCI (288 mg, 1.50 mmol) was added to a solution of [4-((R)-2-hydroxymethyl-6-oxo-piperidin-1-yl)-but-2-ynyloxy]-acetonitrile (118 mg, 0.50 mmol) in benzene (4 mL). The reaction mixture was cooled to 0° C. and DMSO (0.14 mL, 2.0 mmol) was added. After 5 min at 0° C., pyridinium trifluoroacetate (106 mg, 0.55 mmol) was added. The reaction was allowed to warm to rt and then was stirred at rt for 3 h. The solution was decanted from the oily residue and the residue was washed with benzene (3×5 mL). The combined benzene phases were concentrated in vacuo to afford crude [4-((R)-2-formyl-6-oxo-piperidin-1-yl)-but-2-ynyloxy]-acetonitrile, which was used without further purification.

Step 6. {4-[(R)-2-Oxo-6-((E)-3-oxo-4-phenyl-but-1-enyl)-piperidin-1-yl]-but-2-ynyloxy}-acetonitrile Sodium hydride (60% dispersion in oil, 18 mg, 0.45 mmol) was added to a solution of dimethyl 2-oxo-3-phenylpropylphosphonate (110 mg, 0.45 mmol) in THF (1.5 mL) at 0° C. After 1 h at 0° C., a solution of [4-((R)-2-formyl-6-oxo-piperidin-1-yl)-but-2-ynyloxy]-acetonitrile (0.50 mmol, crude from step 5) in THF (1.5 mL) was added via cannula. The reaction was allowed to warm to rt. After 18 h at rt, the reaction was quenched with aqueous acetic acid (50%, 10 mL) and extracted with EtOAc (3×20 mL). The combined organic phase was washed with brine (25 mL), dried ($Na_2SO_4$), filtered and concentrated in vacuo. Purification of the residue by flash column chromatography on silica gel (10% $\rightarrow$40% EtOAc/$CH_2Cl_2$, gradient) afforded 75 mg (48%) of the title compound.

EXAMPLE 92

{4-[(R)-2-Oxo-6-(3-oxo-4-phenyl-butyl)-piperidin-1-yl]-butoxy}-acetonitrile

Palladium on carbon (10 wt. %, 7 mg) was added to a solution of {4-[(R)-2-oxo-6-((E)-3-oxo-4-phenyl-but-1-enyl)-piperidin-1-yl]-but-2-ynyloxy}-acetonitrile (35 mg, 0.10 mmol) in MeOH (3.0 mL). A hydrogen atmosphere was established by evacuating and refilling with hydrogen (3×) and the reaction mixture was stirred under a balloon of hydrogen for 19 h. The reaction mixture was filtered through celite, washing with MeOH, and the filtrate was concentrated in vacuo. Purification of the residue by flash column chromatography on silica gel ($CH_2Cl_2 \rightarrow 2\%$ MeOH/$CH_2Cl_2$, gradient) afforded 20 mg (56%) of the title compound.

EXAMPLE 93

{4-[(R)-2-(3-Hydroxy-4-phenyl-butyl)-6-oxo-piperidin-1-yl]-butoxy}-acetonitrile

Lithium aluminum hydride (1.0 M in THF, 0.02 mL, 0.02 mmol) was added to a solution of {4-[(R)-2-oxo-6-(3-oxo-4-phenyl-butyl)-piperidin-1-yl]-butoxy}-acetonitrile (15.7 mg, 0.044 mmol) in THF (0.75 mL) at 0° C. After 2 h at 0° C. the reaction was quenched with saturated aqueous $NH_4Cl$ (5 mL) and extracted with (3×5 mL). The combined organic phase was dried ($Na_2SO_4$), filtered and concentrated in vacuo to afford 12.3 mg (78%) of the title compound.

EXAMPLE 94

(R)-1-[4-(2-Amino-ethoxy)-butyl]-6-(3-hydroxy-4-phenyl-butyl)-piperidin-2-one

Raney nickel (5 mg) was added to a solution of {4-[(R)-2-(3-hydroxy-4-phenyl-butyl)-6-oxo-piperidin-1-yl]-butoxy}-acetonitrile (10.5 mg, 0.029 mmol) in MeOH (1.5 mL). A hydrogen atmosphere was established by evacuating and refilling with hydrogen (3×) and the reaction mixture was stirred under a balloon of hydrogen for 19 h. The reaction mixture was filtered through celite, washing with MeOH, and the filtrate was concentrated in vacuo to afford 6.9 mg (65%) of the title compound.

These compounds are tested for in vitro activity as described below and the results given in the Table.

Human Recombinant $EP_1$, $EP_2$, $EP_3$, $EP_4$, FP, TP, IP and DP Receptors: Stable Transfectants.

Plasmids encoding the human $EP_1$, $EP_2$, $EP_3$, $EP_4$, FP, TP, IP and DP receptors were prepared by cloning the respective coding sequences into the eukaryotic expression vector pCEP4 (Invitrogen). The pCEP4 vector contains an Epstein Barr virus (EBV) origin of replication, which permits episomal replication in primate cell lines expressing EBV nuclear antigen (EBNA-1). It also contains a hygromycin resistance gene that is used for eukaryotic selection. The cells employed for stable transfection were human embryonic kidney cells (HEK-293) that were transfected with and express the EBNA-1 protein. These HEK-293-EBNA cells (Invitrogen) were grown in medium containing Geneticin (G418) to maintain expression of the EBNA-1 protein. HEK-293 cells were grown in DMEM with 10% fetal bovine serum (FBS), 250 µg $ml^{-1}$ G418 (Life Technologies) and 200 µg $ml^{-1}$ gentamicin or penicillin/streptomycin. Selection of stable transfectants was achieved with 200 µg $ml^{-1}$ hygromycin, the optimal concentration being determined by previous hygromycin kill curve studies.

For transfection, the cells were grown to 50–60% confluency on 10 cm plates. The plasmid pCEP4 incorporating cDNA inserts for the respective human prostanoid receptor (20 µg) was added to 500 µl of 250 mM $CaCl_2$. HEPES buffered saline×2 (2×HBS, 280 mM NaCl, 20 mM HEPES acid, 1.5 mM $Na_2HPO_4$, pH 7.05–7.12) was then added dropwise to a total of 500 µl, with continuous vortexing at room temperature. After 30 min, 9 ml DMEM were added to the mixture. The DNA/DMEM/calcium phosphate mixture was then added to the cells, which had been previously rinsed with 10 ml PBS. The cells were then incubated for 5 hr at 37° C. in humidified 95% air/5% $CO_2$. The calcium phosphate solution was then removed and the cells were treated with 10% glycerol in DMEM for 2 min. The glycerol solution was then replaced by DMEM with 10% FBS. The cells were incubated overnight and the medium was replaced by DMEM/10% FBS containing 250 µg $ml^{-1}$ G418 and penicillin/streptomycin. The following day hygromycin B was added to a final concentration of 200 µg $ml^{-1}$.

Ten days after transfection, hygromycin B resistant clones were individually selected and transferred to a separate well on a 24 well plate. At confluence each clone was transferred to one well of a 6 well plate, and then expanded in a 10 cm dish. Cells were maintained under continuous hygromycin selection until use.

Radioligand Binding

Radioligand binding studies on plasma membrane fractions prepared for cells stably transfected with the cat or human receptor were performed as follows. Cells washed with TME buffer were scraped from the bottom of the flasks and homogenized for 30 sec using a Brinkman PT 10/35 polytron. TME buffer was added as necessary to achieve a 40 ml volume in the centrifuge tubes. TME is comprised of 50 mM TRIS base, 10 mM $MgCl_2$, 1 mM EDTA; pH 7.4 is achieved by adding 1 N HCl. The cell homogenate was centrifuged at 19,000 rpm for 20–25 min at 4° C. using a Beckman Ti-60 or Ti-70 rotor. The pellet was then resuspended in TME buffer to provide a final protein concentration of 1 mg/ml, as determined by Bio-Rad assay. Radioligand binding assays were performed in a 100 µl or 200 µl volume.

The binding of [$^3$H](N) $PGE_2$ (specific activity 165 Ci/mmol) was determined in duplicate and in at least 3 separate experiments. Incubations were for 60 min at 25° C. and were terminated by the addition of 4 ml of ice-cold 50 mM TRIS-HCl followed by rapid filtration through Whatman GF/B filters and three additional 4 ml washes in a cell harvester (Brandel). Competition studies were performed using a final concentration of 2.5 or 5 nM [$^3$H](N) $PGE_2$ and non-specific binding was determined with $10^{-5}$ M unlabelled $PGE_2$.

For radioligand binding on the transient transfectants, plasma membrane fraction preparation was as follows. COS-7 cells were washed with TME buffer, scraped from the bottom of the flasks, and homogenized for 30 sec using a Brinkman PT 10/35 polytron. TME buffer was added to achieve a final 40 ml volume in the centrifuge tubes. The composition of TME is 100 mM TRIS base, 20 mM $MgCl_2$, 2M EDTA; ION HCl is added to achieve a pH of 7.4.

The cell homogenate was centrifuged at 19000 rpm for 20 min at 4° C. using a Beckman Ti-60 rotor. The resultant pellet was resuspended in TME buffer to give a final 1 mg/ml protein concentration, as determined by Biorad assay. Radioligand binding assays were performed in a 200 µl volume.

The binding of [$^3$H] $PGE_2$ (specific activity 165 Ci or $mmol^{-1}$) at $EP_{3D'}$ receptors and [$^3$H]-SQ29548 (specific activity 41.5 Ci mmol$^{-1}$) at TP receptors were determined in duplicate in at least three separate experiments. Radiolabeled PGE$_2$ was purchased from Amersham, radiolabeled SQ29548 was purchased from New England Nuclear. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 2.5 or 5 nM [$^3$H]-PGE$_2$, or 10 nM [$^3$H]-SQ 29548 and non-specific binding determined with 10 μM of the respective unlabeled prostanoid. For all radioligand binding studies, the criteria for inclusion were >50% specific binding and between 500 and 1000 displaceable counts or better.

In Vivo Experimental Data for Certain Compounds Disclosed Herein

The effects of the compounds disclosed herein on intraocular pressure were measured as follows. The compounds were prepared at the desired concentrations in a vehicle comprising 0.1% polysorbate 80 and 10 mM TRIS base. Dogs were treated by administering 25 μl to the ocular surface, the contralateral eye received vehicle as a control. Intraocular pressure was measured by applanation pneumatonometry.

7-[(R)-2-((E)-3-Hydroxy-4-phenyl-but-1-enyl)-6-oxo-piperidin-1-yl]-hept-5-ynoic acid was tested in normotensive dogs at 0.1%, dosing once daily for 5 days. The maximum intraocular pressure (IOP) decrease from baseline was 5.7 mmHg (30%) at 102 h; the maximum ocular surface hyperemia (OSH) score was 1.2 at 52 h.

7-[(R)-2-((E)-3-Hydroxy-4-phenyl-but-1-enyl)-6-oxo-piperidin-1-yl]-heptanoic acid amide was tested in normotensive dogs at 0.01%, dosing once daily for 5 days. The maximum IOP decrease from baseline was 9.8 mmHg (50%) at 102 h; the maximum OSH score was 1.8 at 76 h.

7-[(R)-2-((E)-3-Hydroxy-4-phenyl-but-1-enyl)-6-oxo-piperidin-1-yl]-heptanoic acid isopropyl ester (faster eluting diastereomer by HPLC) was tested in normotensive dogs at 0.01%, dosing once daily for 5 days. The maximum IOP decrease from baseline was 9.0 mmHg (50%) at 76 h; the maximum OSH score was 2.6 at 26, 50, 74 and 98 h.

7-[(R)-2-((E)-3-Hydroxy-4-phenyl-but-1-enyl)-6-oxo-piperidin-1-yl]-heptanoic acid isopropyl ester (slower eluting disastereomer by HPLC) was tested at multiple concentrations in normotensive dogs, dosing once daily for 5 days. At 0.01%, the maximum IOP decrease from baseline was 8.7 mmHg (51%) at 100 h; the maximum OSH score was 1.9 at 52 h. At 0.03%, the maximum IOP decrease from baseline was 7.2 mmHg (36%) at 54 h; the maximum OSH score was 1.3 at 52 h. At 0.001%, the maximum IOP decrease from baseline was 5.5 mmHg (29%) at 100 h; the maximum OSH score was 0.7 at 98 h.

Thus, the compounds of this invention are useful in lowering elevated intraocular pressure in mammals, e.g. humans.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

The invention claimed is:

1. A compound having the formula

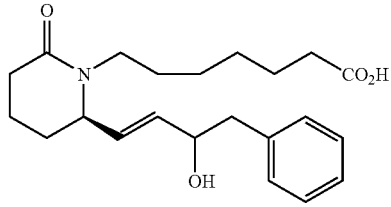

or a pharmaceutically acceptable salt or a prodrug thereof.

2. A method comprising administering a compound to a mammal for the treatment or prevention of glaucoma or ocular hypertension in said mammal, wherein said compound has a formula

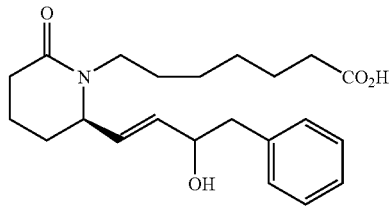

or a is a pharmaceutically acceptable salt or a prodrug thereof.

3. A composition which is a liquid intended for topical administration to an eye of a mammal, said composition comprising a compound of the formula

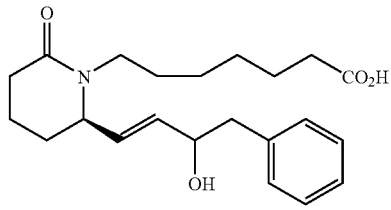

or a pharmaceutically acceptable salt of said compound and ophthalmically acceptable pharmaceutical excipents.

* * * * *